(12) United States Patent
Peckham et al.

(10) Patent No.: US 7,569,579 B2
(45) Date of Patent: Aug. 4, 2009

(54) CYCLOPROPYL COMPOUNDS AS CCR5 ANTAGONISTS

(75) Inventors: Jennifer Poole Peckham, Durham, NC (US); Christopher Joseph Aquino, Durham, NC (US); Wieslaw Mieczyslaw Kazmierski, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 679 days.

(21) Appl. No.: 10/538,196

(22) PCT Filed: Dec. 12, 2003

(86) PCT No.: PCT/US03/39619

§ 371 (c)(1),
(2), (4) Date: Jun. 9, 2005

(87) PCT Pub. No.: WO2004/055010

PCT Pub. Date: Jul. 1, 2004

(65) Prior Publication Data

US 2006/0052408 A1    Mar. 9, 2006

Related U.S. Application Data

(60) Provisional application No. 60/433,626, filed on Dec. 13, 2002.

(51) Int. Cl.
*A61K 31/438* (2006.01)
(52) U.S. Cl. .................. 514/278; 514/304; 514/329; 546/20; 546/126; 546/224; 546/234
(58) Field of Classification Search .......... 546/192, 546/193, 207, 208, 212, 214, 216, 217, 218, 546/219, 220, 221, 225, 236, 237, 238, 126, 546/226, 233, 20, 224, 234; 514/304, 318, 514/319, 320, 322, 323, 396, 278, 329; 548/304.4
See application file for complete search history.

(56) References Cited

U.S. PATENT DOCUMENTS 6,331,541 B1 * 12/2001 Ko et al. ................. 514/237.2

FOREIGN PATENT DOCUMENTS

WO    WO00/39125    7/2000
WO    WO0038680    7/2000

OTHER PUBLICATIONS

Finke et al., Antagonists of the human CCR5 receptor as anti-HIV-1 agents. Part 2: structure-activity relationships for substituted 2-aryl-1-'N-(methyl)-N-(phenylsulfonyl)amino)-4-(piperidin-1-y1) butanes, Bioorganic and Medicinal Chemistry Letters 11(2):265-270 (2001).

Finke et al., Antagonists of the human CCR5 receptor as anti-HIV-1 agents. Part 3: a proposed pharmacophore model for 1-(N-(methyl)-N-(phenylsulfonyl)amino)-2-(phenyl)-4-(4-(substituted)piperidin-1-yl)butanes, Bioorganic and Medicinal Chemistry Letters 11(18):2469-2473(2001).

Finke et al., Antagonists of the human CCR5 receptor as anti-HIV-1 agents. Part 4: synthesis and structure-activity relationships for 1-[*N*-(methyl)-*N*-(phenylsulfonyl)amino]-2-(phenyl)-4-(4-(*N*-(alkyl)-*N*-benzyloxycarbonyl)amino)piperidin-1-yl)butanes, Bioorganic and Medicinal Chemistry Letters 11:2475-2479 (2001).

Dorn et al., Antagonists of the human CCR5 receptor as anti-HIV-1 agents. Part 1: Discovery and initial structure-activity relationships for 1-amino-2-phenyl-4-(piperidin-1-yl)butanes, Bioorganic and Medicinal Chemistry Letter 11(2):259-264 (2001).

Maeda et al., The current status of the challenges in, the development of CCR5 inhibitors as therapeutics for HI infection, Current Opinion in Pharmacology 4(5):447-452 (2004).

Kumar et al., Pharmacokinetics and Interactions of a Novel Antagonist of Chemokine Receptor 5 (CCR5) with Ritonavir in Rats and Monkeys: Role of CYP3A and P-glycoprotein, J. of Pharmacology and Experimental therapeutics 304(3):1161-1171(2003).

Bonnaud et al., 1-Aryl-2-(aminomethyl))cyclopropanecarboxylic Acid Derivatives. A New Series of Potential Antidepressants, J. Med. Chem 30:318-325 (1987).

* cited by examiner

*Primary Examiner*—Bernard Dentz
*Assistant Examiner*—David E Gallis
(74) *Attorney, Agent, or Firm*—Bonnie L. Deppenbrock

(57) ABSTRACT

The present invention relates to compounds of formula (I), or pharmaceutically acceptable derivatives thereof, useful in the treatment of CCR5-related diseases and disorders, for example, useful in the inhibition of HIV replication, the prevention or treatment of an HIV infection, and in the treatment of the resulting acquired immune deficiency syndrome (AIDS).

4 Claims, No Drawings

CYCLOPROPYL COMPOUNDS AS CCR5 ANTAGONISTS

CROSS-REFERENCE TO RELATED APPLICATIONS

This application is filed pursuant to 35 U.S.C. § 371 United States National Phase Application of International Application No. PCT/US2003/039619 filed Dec. 12, 2003, which claims priority from U.S. Provisional Application No. 60/433,626 filed Dec. 13, 2002.

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss.

In addition to CD4, HIV requires a co-receptor for entry into target cells. The chemokine receptors function together with CD4 as co-receptors for HIV. The chemokine receptors CXCR4 and CCR5 have been identified as the main co-receptors for HIV-1. CCR5 acts as a major co-receptor for fusion and entry of macrophage-tropic HIV into host cells. These chemokine receptors are thought to play an essential role in the establishment and dissemination of an HIV infection. Therefore, CCR5 antagonists are thought to be useful as therapeutic agents active against HIV.

We have now discovered a series of small molecule nonpeptide compounds that are useful as inhibitors of HIV replication.

BRIEF DESCRIPTION OF THE INVENTION

The present invention features compounds that are useful in the inhibition of HIV replication, the prevention of infection by HIV, the treatment of infection by HIV and in the treatment of AIDS and/or ARC, either as pharmaceutically acceptable salts or pharmaceutical composition ingredients. The present invention further features methods of treating AIDS, methods of preventing infection by HIV, and methods of treating infection by HIV as monotherapy or in combination with other antivirals, anti-infectives, immunomodulators, antibiotics or vaccines. The present invention also features pharmaceutical compositions, comprising the above-mentioned compounds that are suitable for the prevention or treatment of CCR5-related diseases and conditions. The present invention further features processes for making the above-mentioned compounds.

SUMMARY OF THE PRESENT INVENTION

The present invention includes compounds of formula (I):

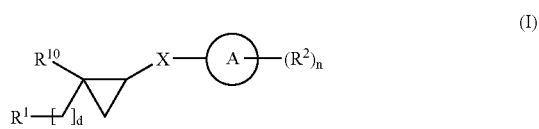

(I)

or pharmaceutically acceptable derivatives thereof, wherein:

X is a $C_{1-5}$ alkylene chain, wherein said X is optionally substituted by one or more =O, =S, alkyl, or halogen and wherein said $C_{1-5}$ alkylene chain may optionally have 0-3 heteroatoms selected from oxygen, phosphorus, sulfur, or nitrogen;

Ring A is a saturated, partially saturated or aromatic 3-7 monocyclic or 8-10 membered bicyclic ring having one ring nitrogen and 0-4 additional heteroatoms selected from oxygen, phosphorus, sulfur, or nitrogen;

$R^1$ is selected from the group consisting of (a) a saturated, partially saturated, or aromatic 4-7 monocyclic or 8-10 membered bicyclic ring having one ring nitrogen and 0-4 additional heteroatoms selected from oxygen, phosphorus, sulfur, or nitrogen, optionally attached through a $C_{1-6}$ alkylene chain, and optionally substituted by one or more $R^8$;

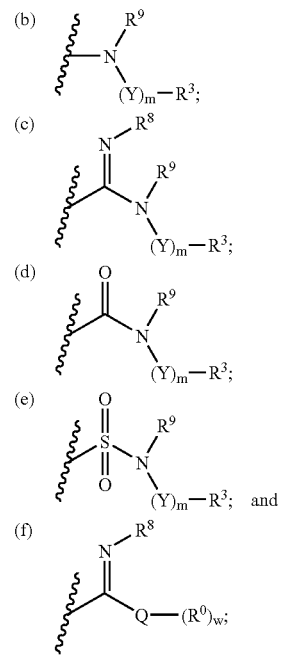

Q is carbon, oxygen, or $S(O)_t$;

w is 1 or 2;

each $R^2$ is independently selected from the group consisting of —$OR^0$, —C(O)—$R^0$, —$S(O)_2$—$R^0$, —C(O)—N($R^0$)$_2$, —$S(O)_2$—N($R^0$)$_2$, —(CH$_2$)$_a$—N($R^0$)(—$V_b$—$R^+$), —(CH$_2$)$_a$—(—$V_b$—$R^+$), halogen, alkyl optionally substituted by one or more $R^7$, alkenyl optionally substituted by one or more $R^7$, alkynyl optionally substituted by one or more $R^7$, aryl optionally substituted by one or more $R^6$, heteroaryl optionally substituted by one or more $R^6$, cycloalkyl optionally substituted by one or more $R^8$, and heterocyclyl optionally substituted by one or more $R^8$; and two adjacent $R^2$s on Ring A are optionally taken together to form a fused, saturated, partially saturated or aromatic 5-6 membered ring having 0-3 heteroatoms selected from oxygen, phosphorus, sulfur, or nitrogen; or two geminal $R^2$s are optionally taken together to form a spiro, saturated, partially saturated or aromatic 5-6 membered ring having 0-3 heteroatoms selected from oxygen, phosphorus, sulfur, or nitrogen, said fused or spiro ring being optionally substituted by one or more $R^8$;

each a independently is 0-3;

each b independently is 0 or 1;

V is —C(O)—, —C(O)O—, —$S(O)_2$—, or —C(O)—N($R^0$)—;

$R^+$ is alkyl, cycloalkyl, aralkyl, aryl, heteroaryl, heteroaralkyl, or heterocyclyl, wherein said $R^+$ is optionally substituted by one or more $R^8$;

d is 0-3;

m is 0 or 1;

n is 0-5;

$R^3$ is H, $-N(R^0)_2$, $-N(R^0)C(O)R^0$, $-CN$, halogen, $CF_3$, alkyl optionally substituted by one or more groups selected from $R^7$ or $-S$-aryl optionally substituted by $-(CH_2)_{1-6}-N(R^0)SO_2(R^0)$, alkenyl optionally substituted by one or more groups selected from $R^7$ or $-S$-aryl optionally substituted by $-(CH_2)_{1-6}-N(R^0)SO_2(R^0)$, alkynyl optionally substituted by one or more groups selected from $R^7$ or $-S$-aryl optionally substituted by $-(CH_2)_{1-6}-N(R)SO_2(R^0)$, cycloalkyl or carbocyclyl optionally substituted by one or more $R^8$, aryl optionally substituted by one or more $R^6$, heteroaryl optionally substituted by one or more $R^6$, or heterocyclyl optionally substituted by one or more $R^8$;

Y is alkyl, alkenyl, alkynyl, $-(CR^4R^5)_p-$, $-C(O)-$, $-C(O)C(O)-$, $-C(S)-$, $-O-(CH_2)_{0-4}-C(O)$, $-(CH_2)_{0-4}-C(O)-O-$, $-N(R^0)-C(O)-$, $-C(O)-N(R^0)-$, $-N(R^0)-C(S)-$, $-S(O)_t-$, $-O-C(=N-CN)-$, $-O-C(=N-R^0)-$, $-C(=N-CN)-O-$, $-C(=N-CN)-S-$, $-S-C(=N-R^0)-O-$, $-S-C(=N-CN)-$, $-N(R^0)-C(=N-CN)-$, $-C(=N-CN)-$, $-N(R^0)-C[=N-C(O)-R^0]$, $-N(R^0)-C[=N-S(O)_t-R^0]$, $-N(R^0)-C(=N-OR^0)-$, $-N(R^0)-C(=N-R^0)-$, or $-C(=N-R^0)-$;

each $R^4$ is independently H or alkyl optionally substituted by $R^7$, alkenyl optionally substituted by $R^7$, or alkynyl optionally substituted by $R^7$;

each $R^5$ is independently selected from the group consisting of H, $-C(O)-OR^6$, $-C(O)-N(R^0)_2$, $-S(O)_t-N(R^0)_2$, $-S(O)_t-R^0$, aryl optionally substituted by $R^6$, and heteroaryl optionally substituted by $R^6$;

p is 1-5;

each t independently is 1 or 2;

each $R^6$ is independently selected from the group consisting of halogen, $-CF_3$, $-OCF_3$, $-OR^0$, $-(CH_2)_{1-6}-OR^0$, $-SR^0$, $-(CH_2)_{1-6}-SR^0$, $-SCF_3$, $-R^0$, methylenedioxy, ethylenedioxy, $-NO_2$, $-CN$, $-(CH_2)_{1-6}-CN$, $-N(R^0)_2$, $-(CH_2)_{1-6}-N(R^0)_2$, $-NR^0C(O)R^0$, $-NR^0(CN)$, $-NR^0C(O)N(R^0)_2$, $-NR^0C(S)N(R^0)_2$, $-NR^0CO_2R^0$, $-NR^0NR^0C(O)R^0$, $-NR^0NR^0CO_2R^0$, $-NR^0NR^0C(O)N(R^0)_2$, $-NR^0NR^0CO_2R^0$, $-C(O)C(O)R^0$, $-C(O)CH_2C(O)R^0$, $-(CH_2)_{0-6}CO_2R^0$, $-O-C(O)R^0$, $-C(O)R^0$, $-C(O)N(R^0)N(R^0)_2$, $-C(O)N(R^0)_2$, $-C(O)N(R^0)OH$, $-C(O)N(R^0)SO_2R^0$, $-OC(O)N(R^0)_2$, $-S(O)_tR^0$, $-S(O)_t-OR^0$, $-S(O)_tN(R^0)C(O)R^0$, $-S(O)_tN(R^0)OR^0$, $-NR^0SO_2N(R^0)_2$, $-NR^0SO_2R^0$, $-C(=S)N(R^0)_2$, $-C(=NH)-N(R^0)_2$, $-(CH_2)_{1-6}-C(O)R^0$, $-C(=N-OR^0)-N(R^0)_2$, $-O-(CH_2)_{0-6}-SO_2N(R^0)_2$, $-(CH_2)_{1-6}NHC(O)R^0$, and $-SO_2N(R^0)_2$ wherein the two $R^0$s on the same nitrogen are optionally taken together to form a 5-8 membered saturated, partially saturated, or aromatic ring having additional 0-4 heteroatoms selected from oxygen, phosphorus, nitrogen, or sulfur;

each $R^7$ is independently selected from the group consisting of halogen, $-CF_3$, $-R^0$, $-OR^0$, $-OCF_3$, $-(CH_2)_{1-6}-OR^0$, $-SR^0$, $-SCF_3$, $-(CH_2)_{1-6}-SR^0$, aryl optionally substituted by $R^6$, methylenedioxy, ethylenedioxy, $-NO_2$, $-CN$, $-(CH_2)_{1-6}-CN$, $-N(R^0)_2$, $-(CH_2)_{1-6}-N(R^0)_2$, $-NR^0C(O)R^0$, $-NR^0(CN)$, $-NR^0C(O)N(R^0)_2$, $-N(R^0)C(S)N(R^0)_2$, $-NR^0CO_2R^0$, $-NR^0NR^0C(O)R^0$, $-NR^0NR^0C(O)N(R^0)_2$, $-NR^0NR^0CO_2R^0$, $-C(O)C(O)R^0$, $-C(O)CH_2C(O)R^0$, $-(CH_2)_{0-6}-CO_2R^0$, $-C(O)R^0$, $-C(O)N(R^0)N(R^0)_2$, $-C(O)N(R^0)_2$, $-C(O)N(R^0)OH$, $-OC(O)R^0$, $-C(O)N(R^0)SO_2R^0$, $-OC(O)N(R^0)_2$, $-S(O)_tR^0$, $-S(O)_t-OR^0$, $-S(O)_tN(R^0)C(O)R^0$, $-S(O)_tN(R^0)OR^0$, $-NR^0SO_2N(R^0)_2$, $-NR^0SO_2R^0$, $-C(=S)N(R^0)_2$, $-C(=NH)-N(R^0)_2$, $-(CH_2)_{1-6}-C(O)R^0$, $-C(=N-OR^0)-N(R^0)_2$, $-O-(CH_2)_{0-6}-SO_2N(R^0)_2$, $-(CH_2)_{1-6}-NHC(O)R^0$, and $-SO_2N(R^0)_2$ wherein the two $R^0$s on the same nitrogen are optionally taken together to form a 5-8 membered saturated, partially saturated, or aromatic ring having additional 0-4 heteroatoms selected from oxygen, phosphorus, nitrogen, or sulfur;

each $R^8$ independently is selected from the group consisting of $R^7$, =O, =S, =N($R^0$), and =N(CN);

$R^9$ is hydrogen, alkyl optionally substituted by one or more $R^7$, alkenyl optionally substituted by one or more $R^7$, alkynyl optionally substituted by one or more $R^7$, cycloalkyl optionally substituted by one or more $R^8$, heterocyclyl optionally substituted by one or more $R^8$, heteroaryl optionally substituted by one or more $R^6$, or aryl optionally substituted by one or more $R^6$; or $-(Y)_m-R^3$ and $R^9$ may combine with the nitrogen atom with which they are attached to form a saturated, partially saturated, or aromatic 5-7 membered monocyclic or 8-10 membered bicyclic ring that optionally contains 1 to 3 additional heteroatoms selected oxygen, phosphorus, sulfur, or nitrogen, wherein said ring may be optionally substituted with one or more $R^8$;

$R^{10}$ is hydrogen, alkyl optionally substituted by one or more $R^7$, alkenyl optionally substituted by one or more $R^7$, alkynyl optionally substituted by one or more $R^7$, cycloalkyl optionally substituted by one or more $R^8$, heterocyclyl optionally substituted by one or more $R^8$, heteroaryl optionally substituted by one or more $R^6$, or aryl optionally substituted by one or more $R^6$;

each $R^0$ is independently selected from the group consisting of hydrogen, alkyl, alkenyl, alkynyl, cycloalkyl, carbocyclylalkyl, aryl, heteroaryl, aralkyl, heteroaralkyl, heterocyclyl, and heterocyclylalkyl, wherein each member of $R^0$ except H is optionally substituted by one or more $R^*$, $OR^*$, $N(R^*)_2$, =O, =S, halogen, $CF_3$, $NO_2$, $CN$, $-C(O)R^*$, $-CO_2R^*$, $-C(O)$-aryl, $-C(O)$-heteroaryl, $-C(O)$aralkyl, $-S(O)_t$-aryl, $-S(O)_t$-heteroaryl, $-NR^*SO_2R^*$, $-NR^*C(O)R^*$, $-NR^*C(O)N(R^*)_2$, $-N(R^*)C(S)N(R^*)_2$, $-NR^*CO_2R^*$, $-NR^*NR^*C(O)R^*$, $-NR^*NR^*C(O)N(R^*)_2$, $-NR^*NR^*CO_2R^*$, $-C(O)C(O)R^*$, $-C(O)CH_2C(O)R^*$, $-C(O)N(R^*)N(R^*)_2$, $-C(O)N(R^*)_2$, $-C(O)NR^*SO_2R^*$, $-OC(O)N(R^*)_2$, $-S(O)_tR^*$, $-NR^*SO_2N(R^*)_2$, $-SO_2N(R^*)_2$ wherein the two $R^*$s on the same nitrogen are optionally taken together to form a 5-8 membered saturated, partially saturated, or aromatic ring having additional 0-4 heteroatoms selected from oxygen, phosphorus, nitrogen, or sulfur; and each $R^*$ is independently H, alkyl, alkenyl, alkynyl, cycloalkyl, aryl, or heteroaryl.

In one embodiment, suitably $R^{10}$ is optionally substituted aryl, such as optionally substituted phenyl.

In one embodiment, $R^1$ is

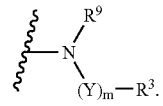

In one embodiment $R^9$ is alkyl and preferably $R^9$ is methyl.
In one embodiment $-(Y)_m-R^3$ suitably is
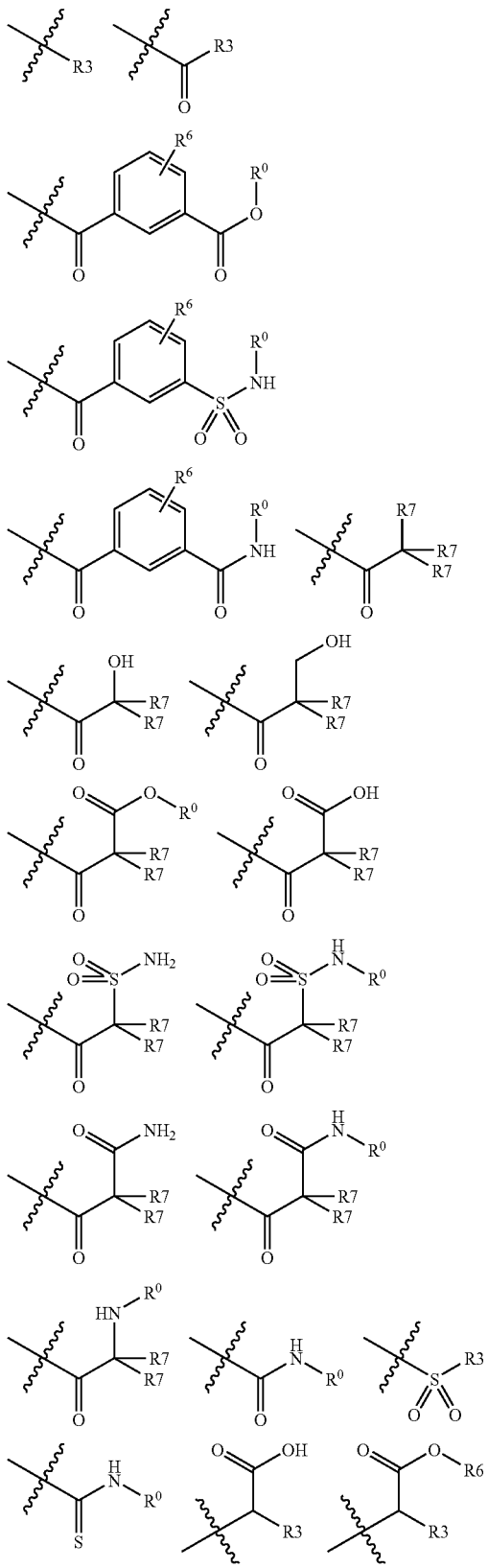
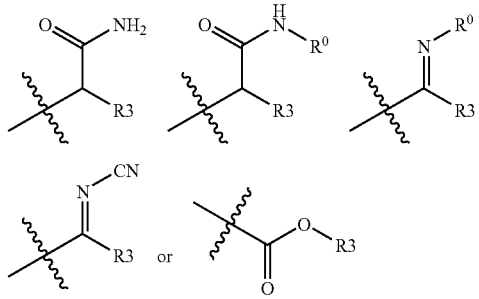
-continued
More suitably $-(Y)_m-R^3$ is
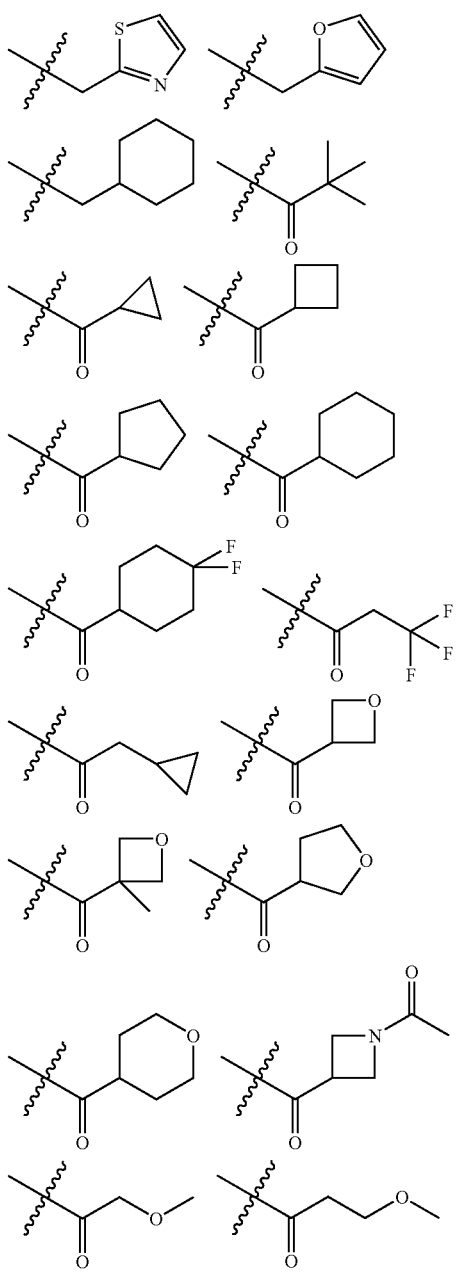

-continued
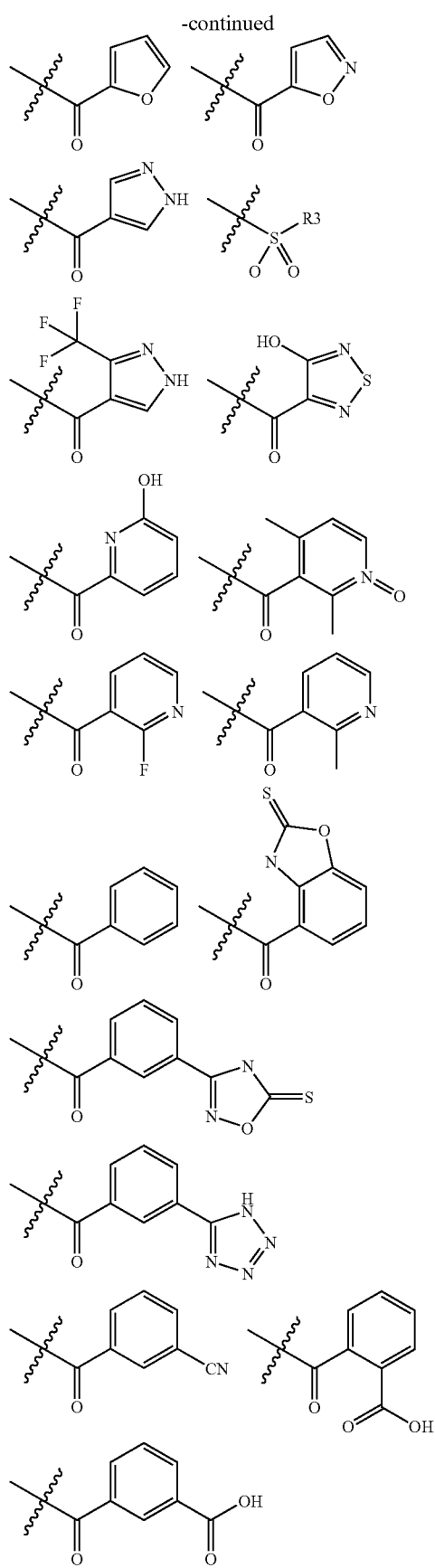
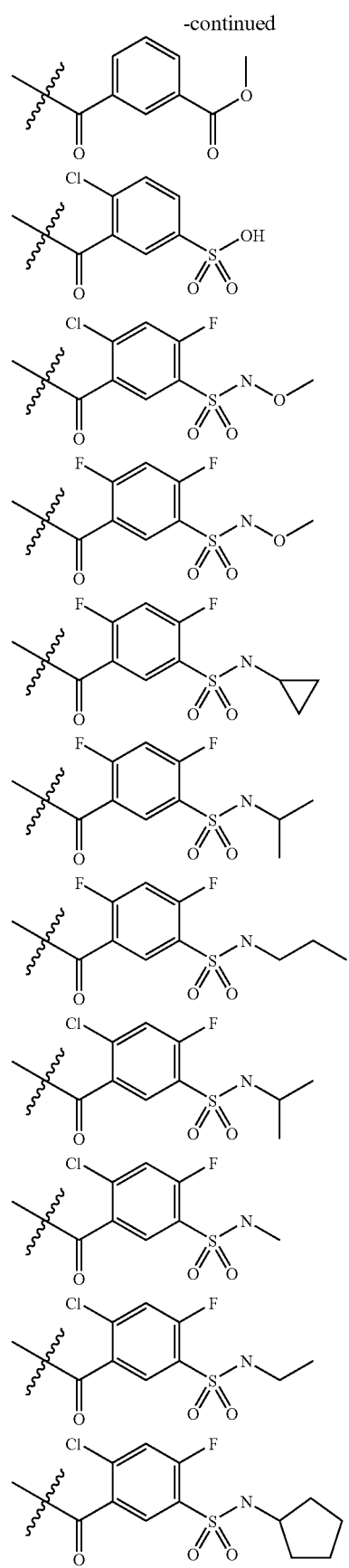

-continued
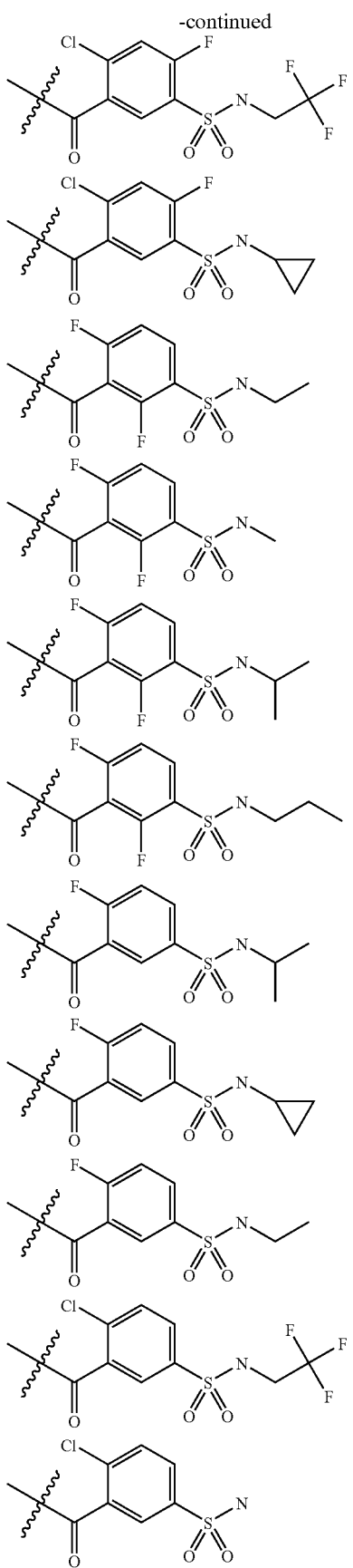
-continued
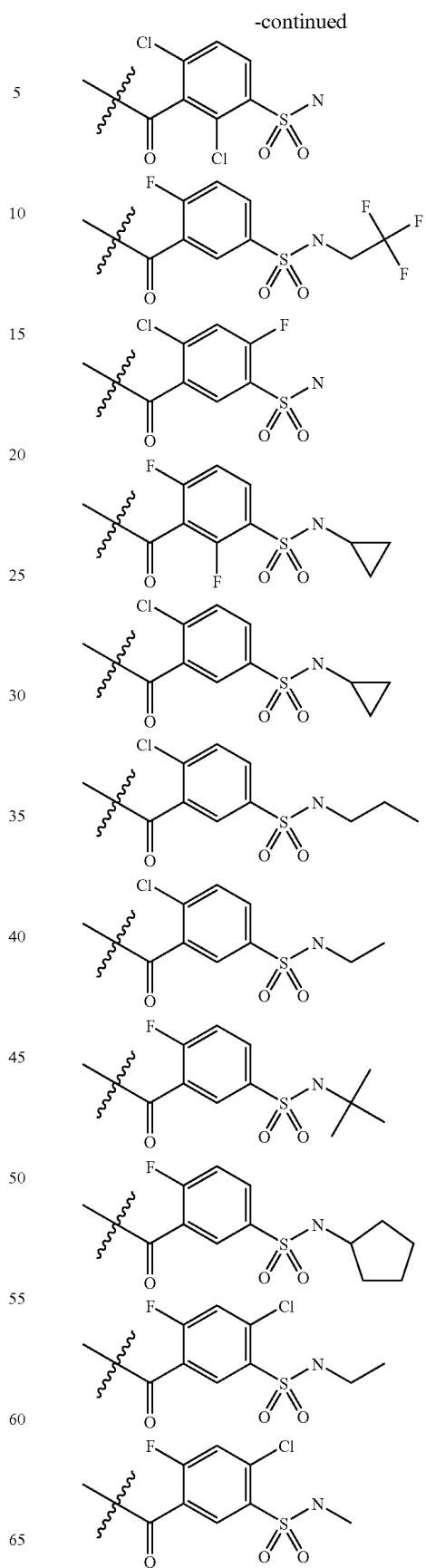

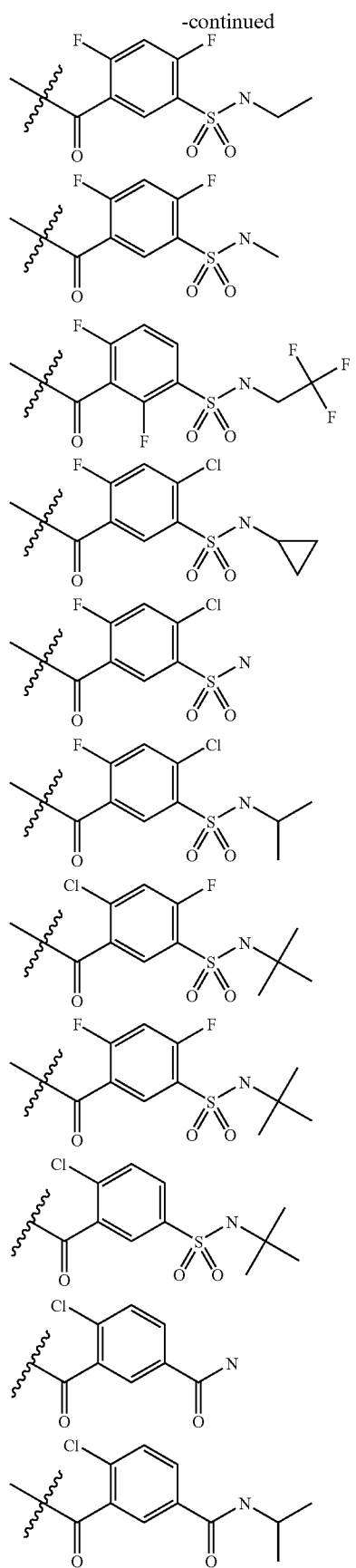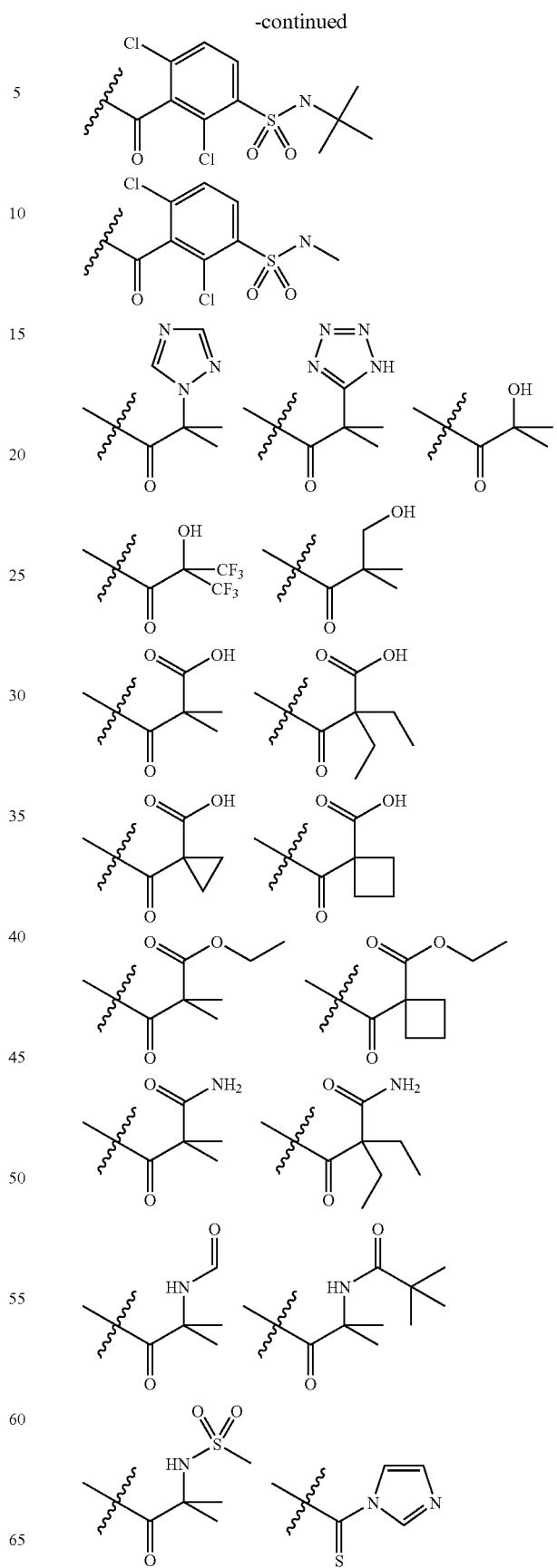

-continued
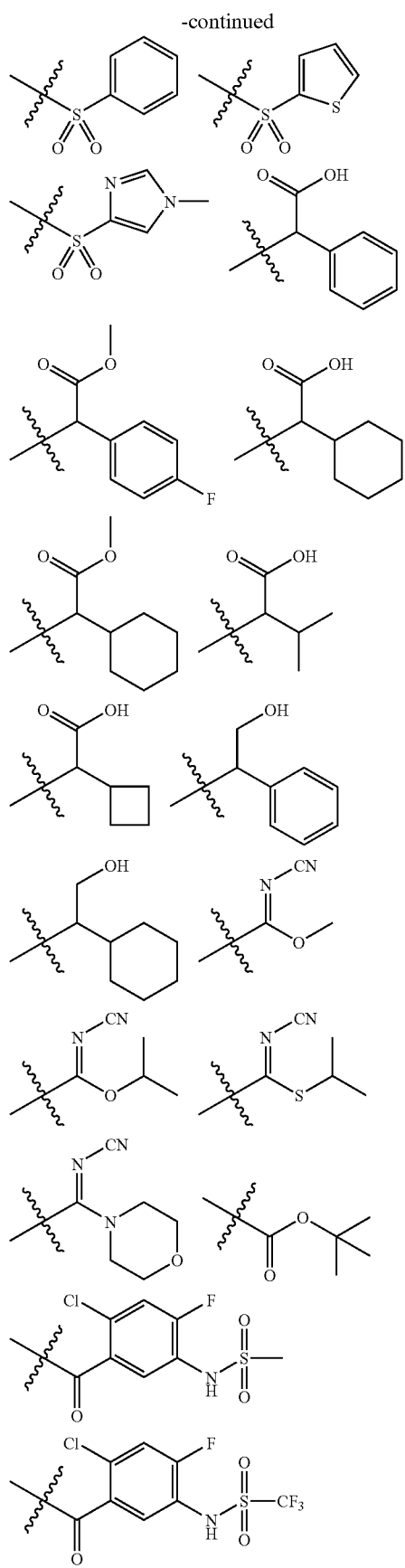
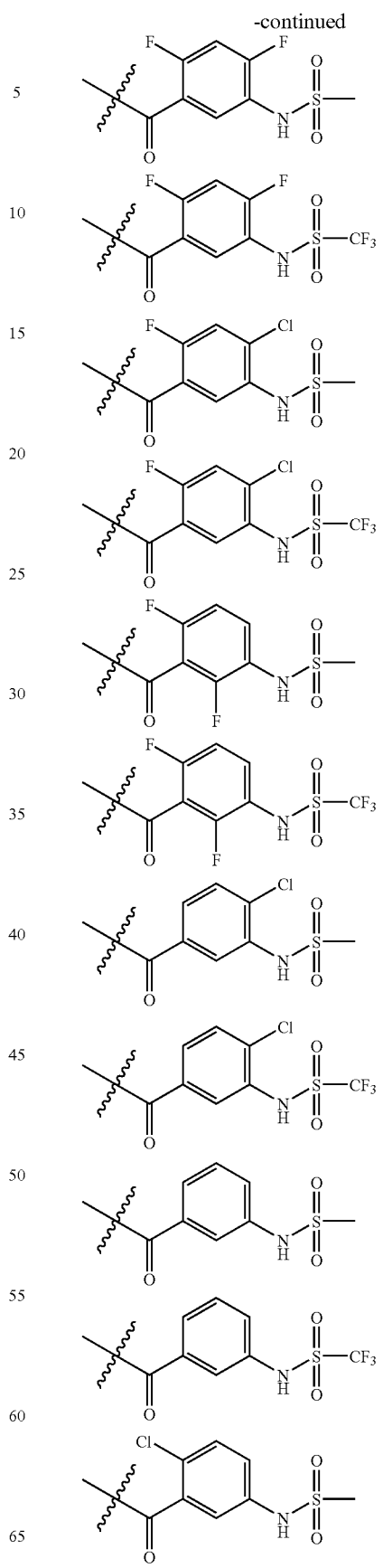

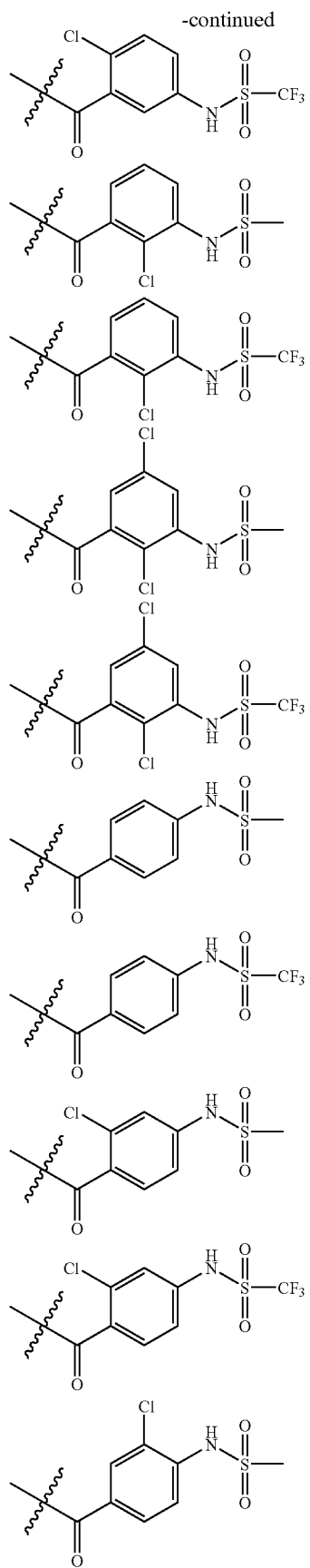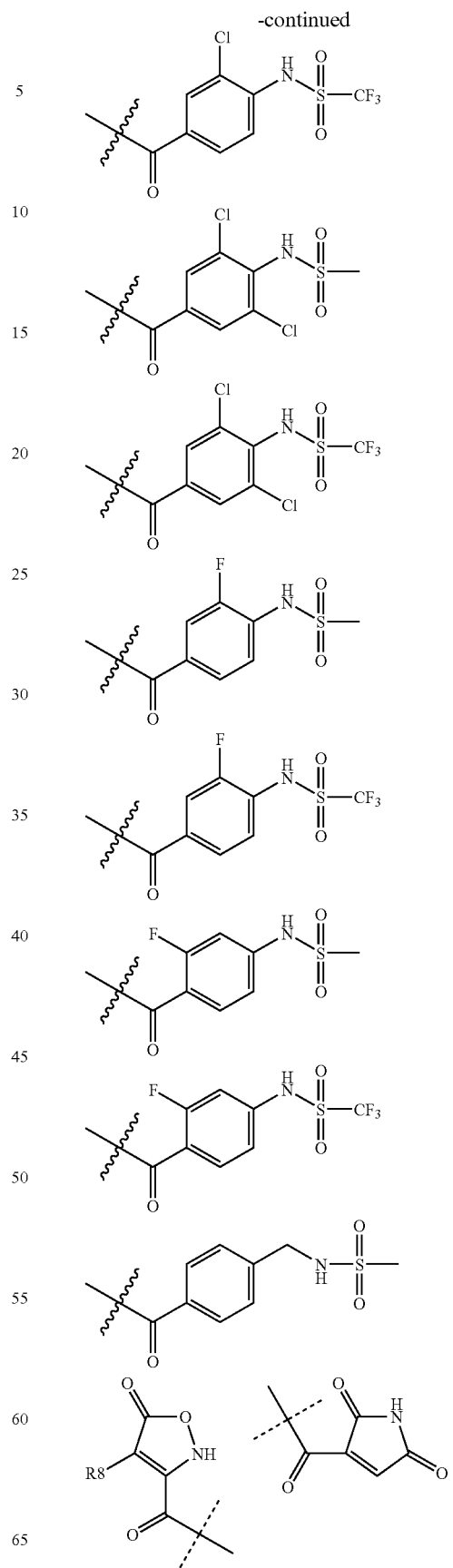

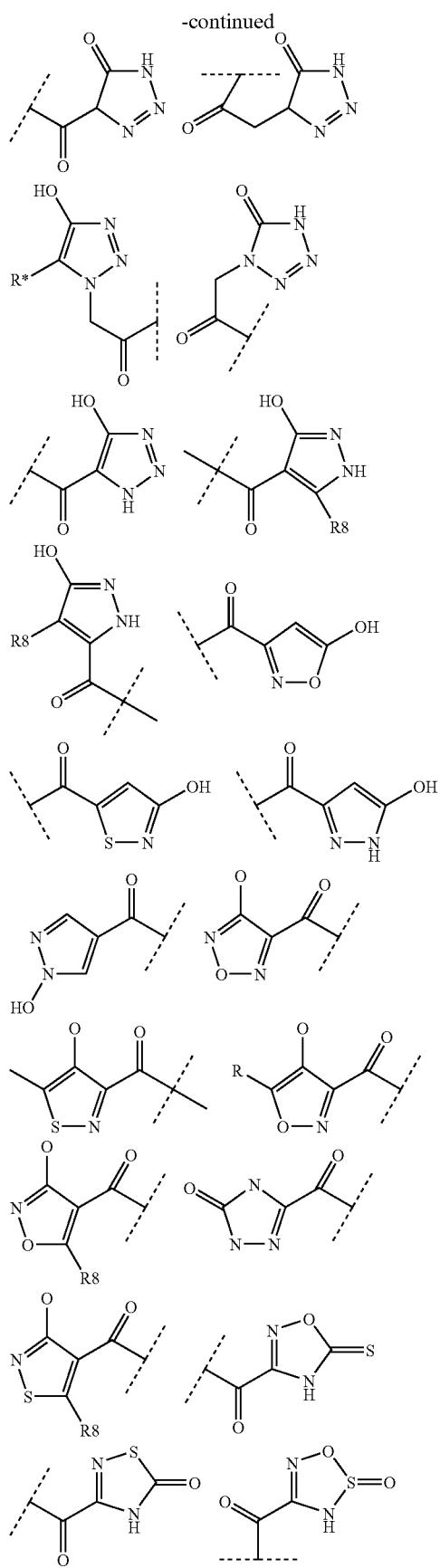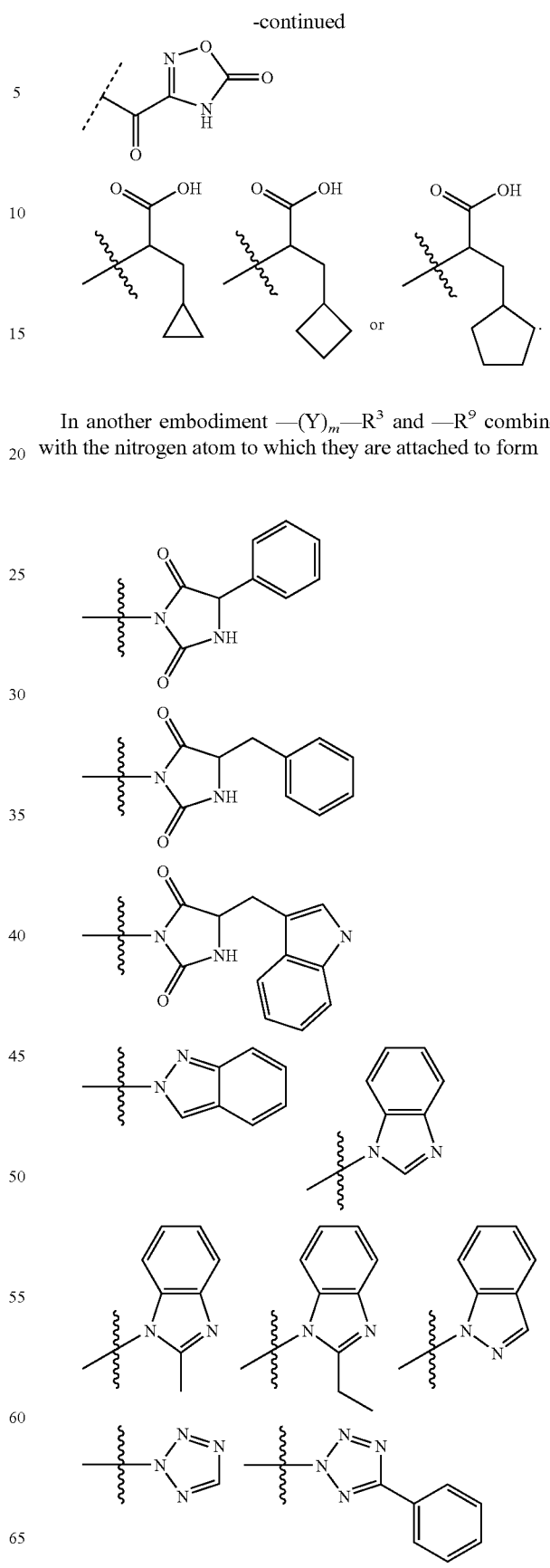
In another embodiment —(Y)$_m$—R$^3$ and —R$^9$ combine with the nitrogen atom to which they are attached to form -continued

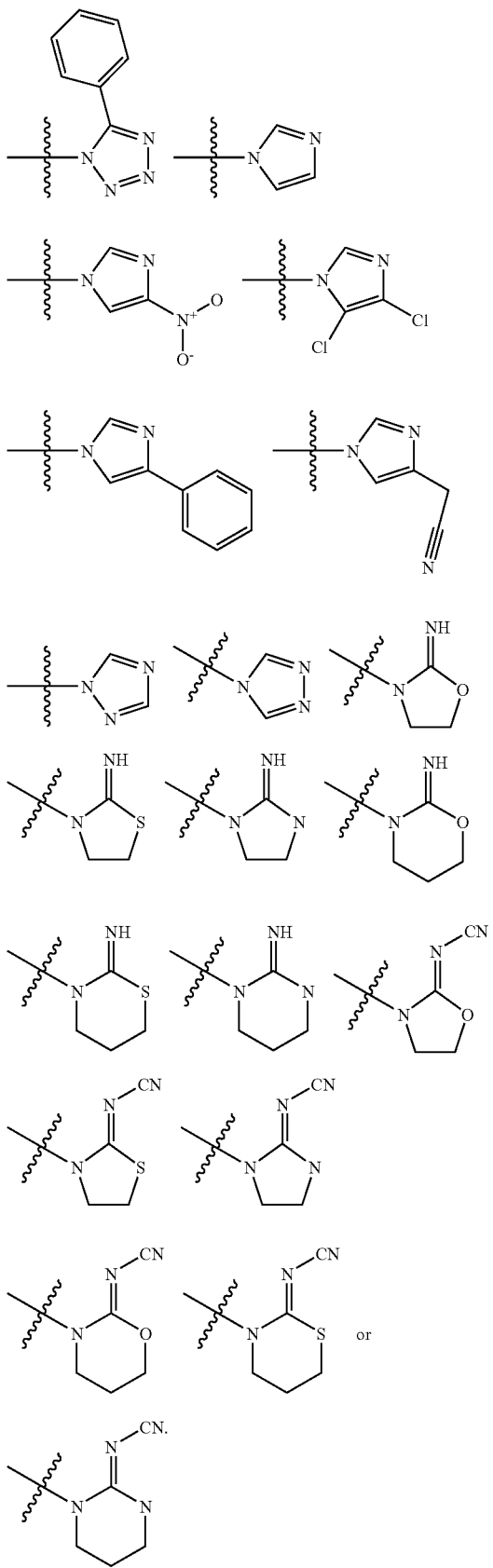

In one embodiment $R^1$ is selected from

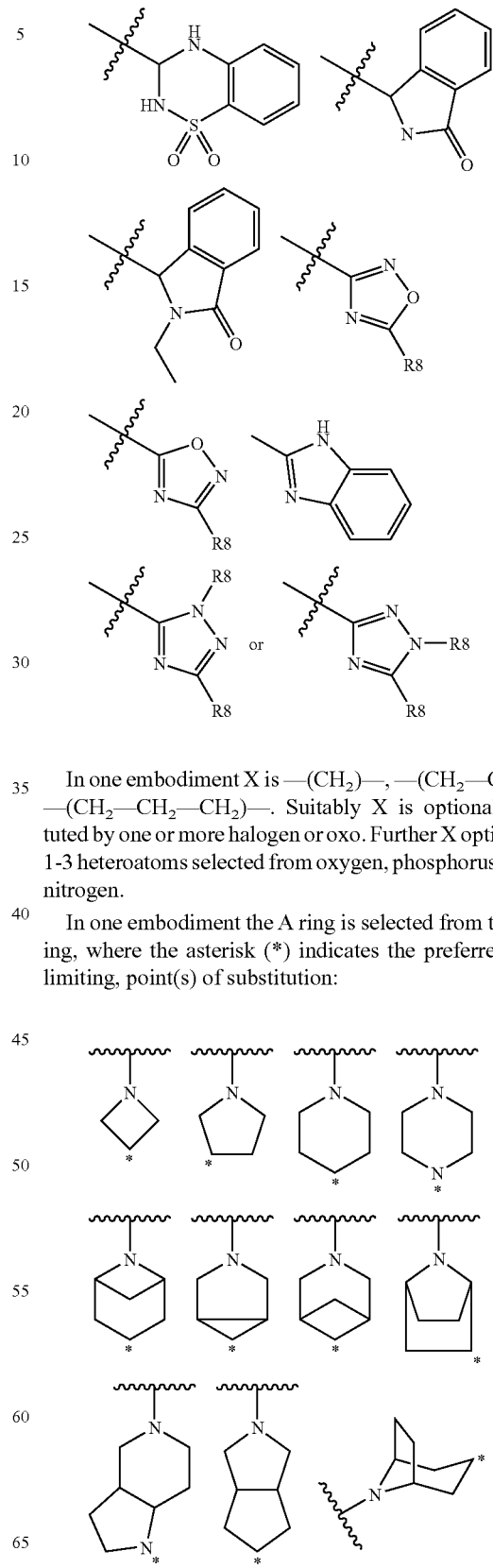

In one embodiment X is —(CH$_2$)—, —(CH$_2$—CH$_2$)—, or —(CH$_2$—CH$_2$—CH$_2$)—. Suitably X is optionally substituted by one or more halogen or oxo. Further X optionally has 1-3 heteroatoms selected from oxygen, phosphorus, sulfur, or nitrogen.

In one embodiment the A ring is selected from the following, where the asterisk (*) indicates the preferred, but not limiting, point(s) of substitution:

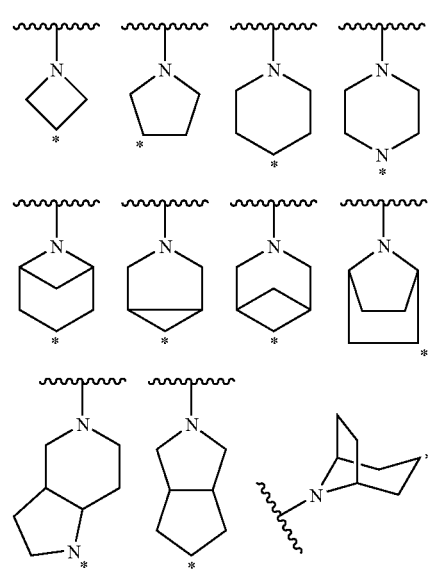

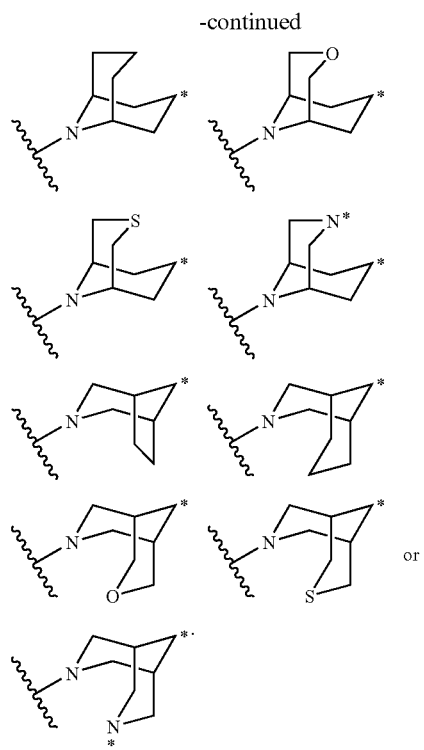
Suitably each R², with the asterisk (*) indicating a preferred, but not limiting, point of substitution from Ring A, independently is selected from
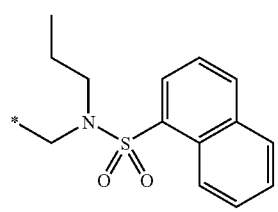
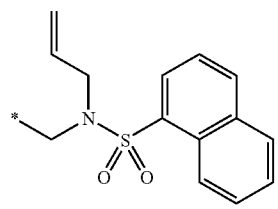
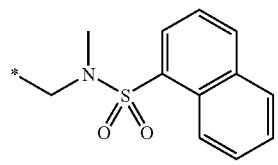
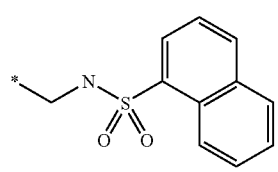
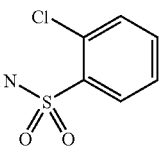
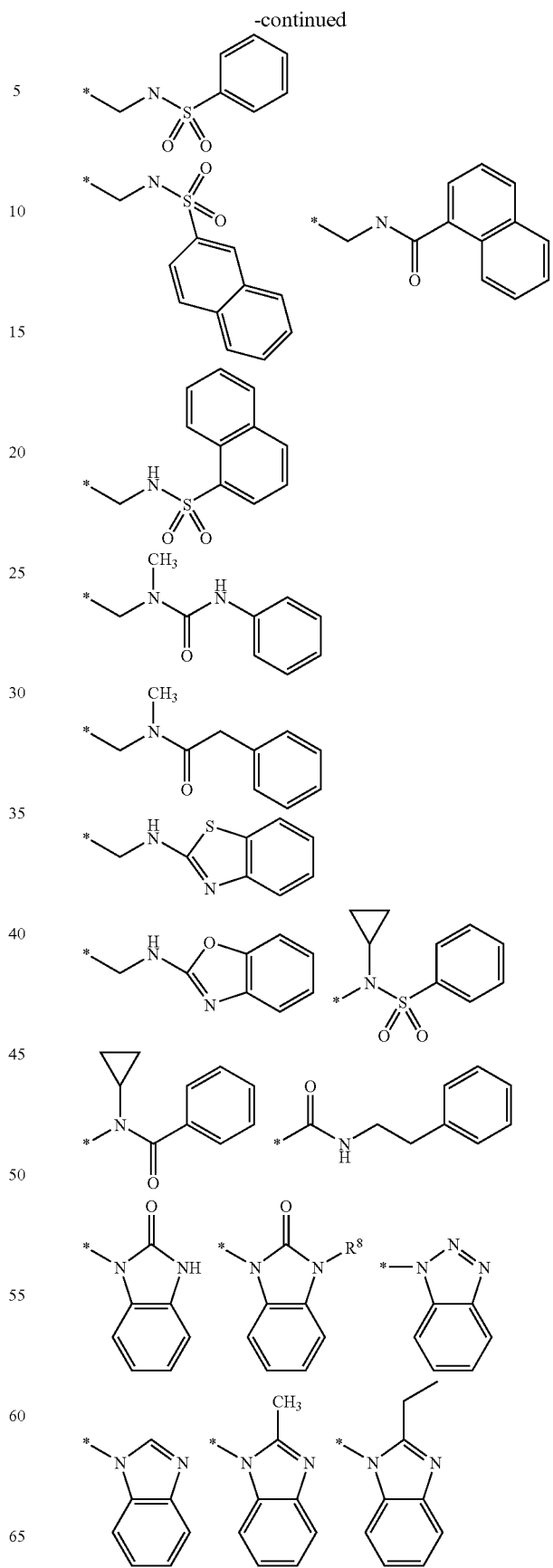

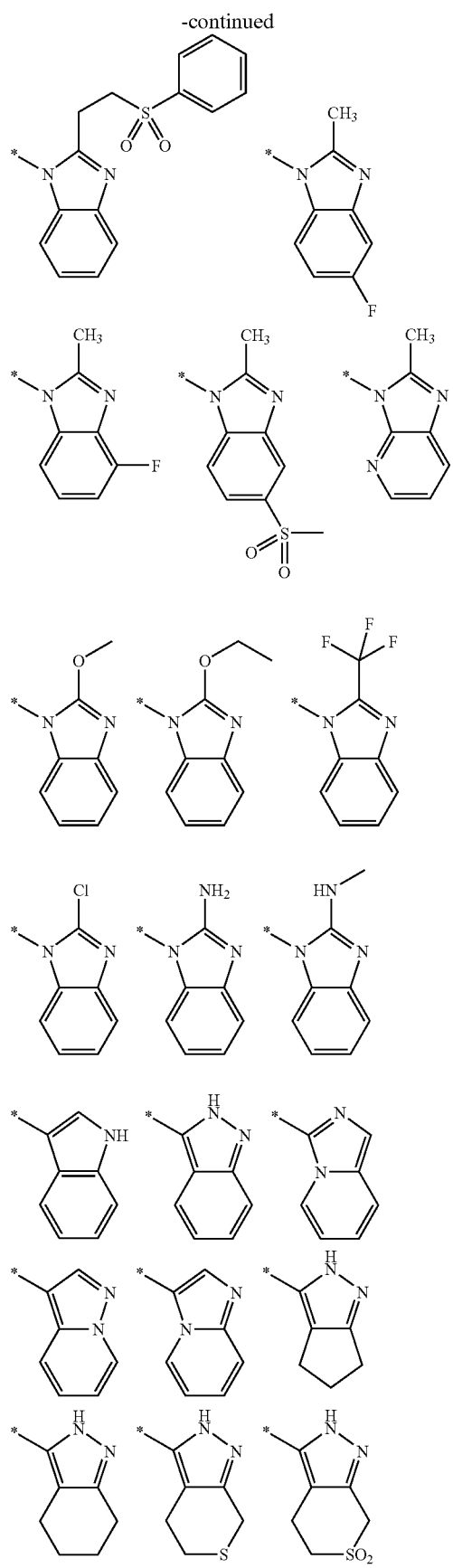
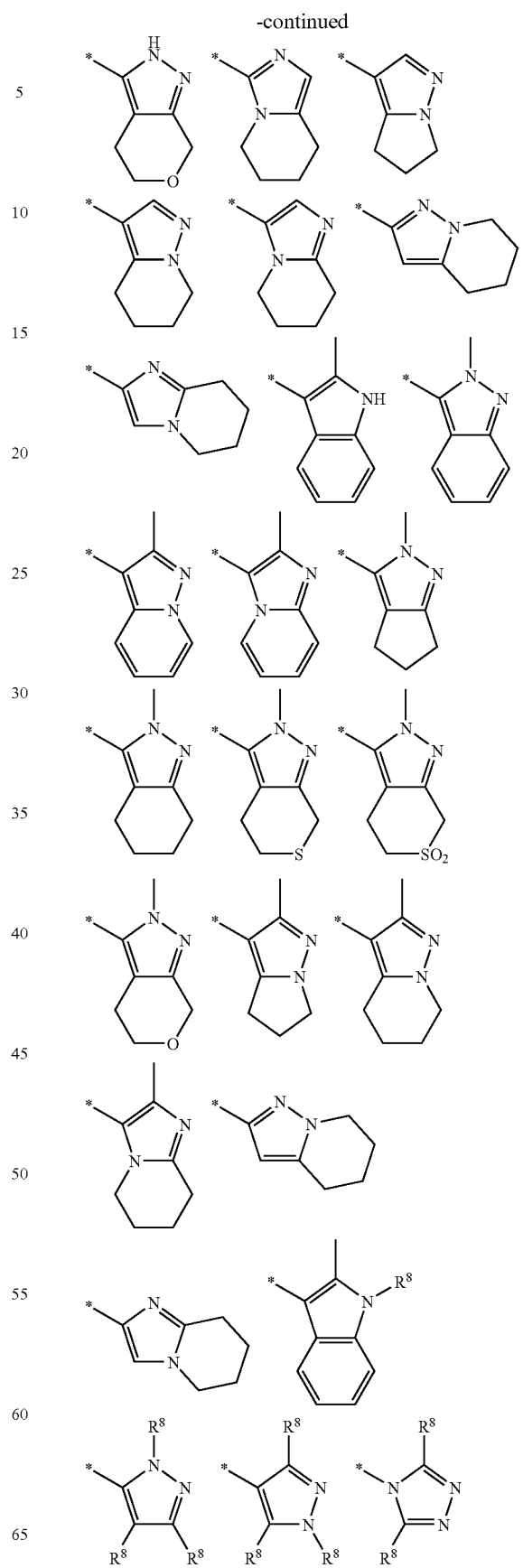

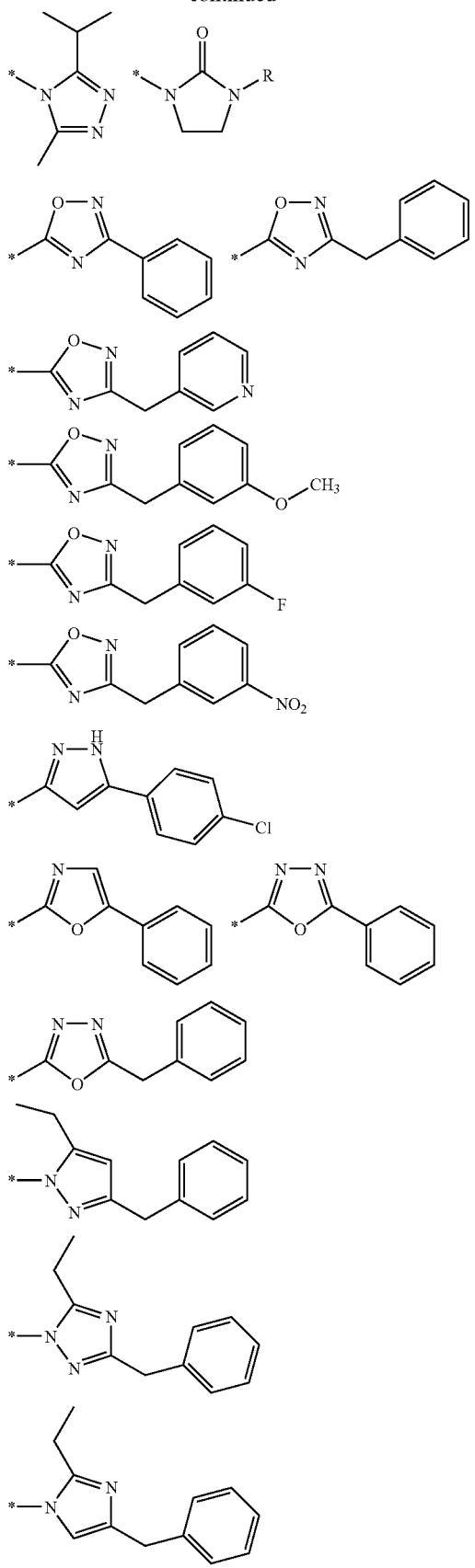
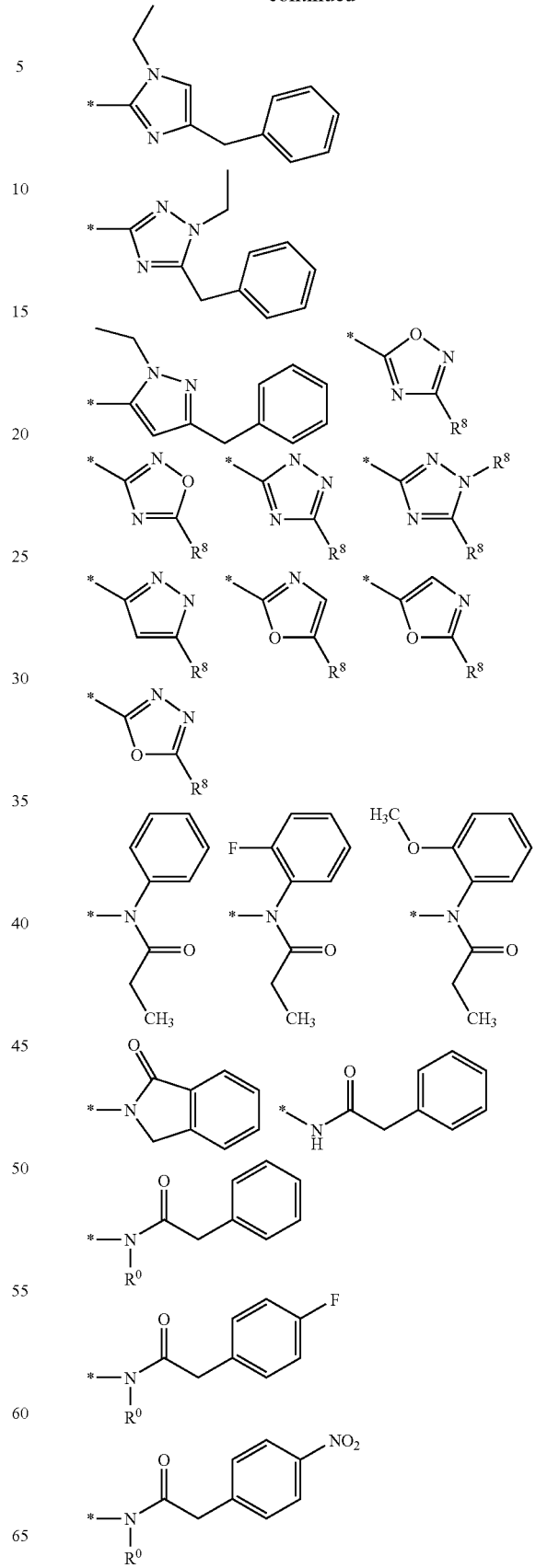

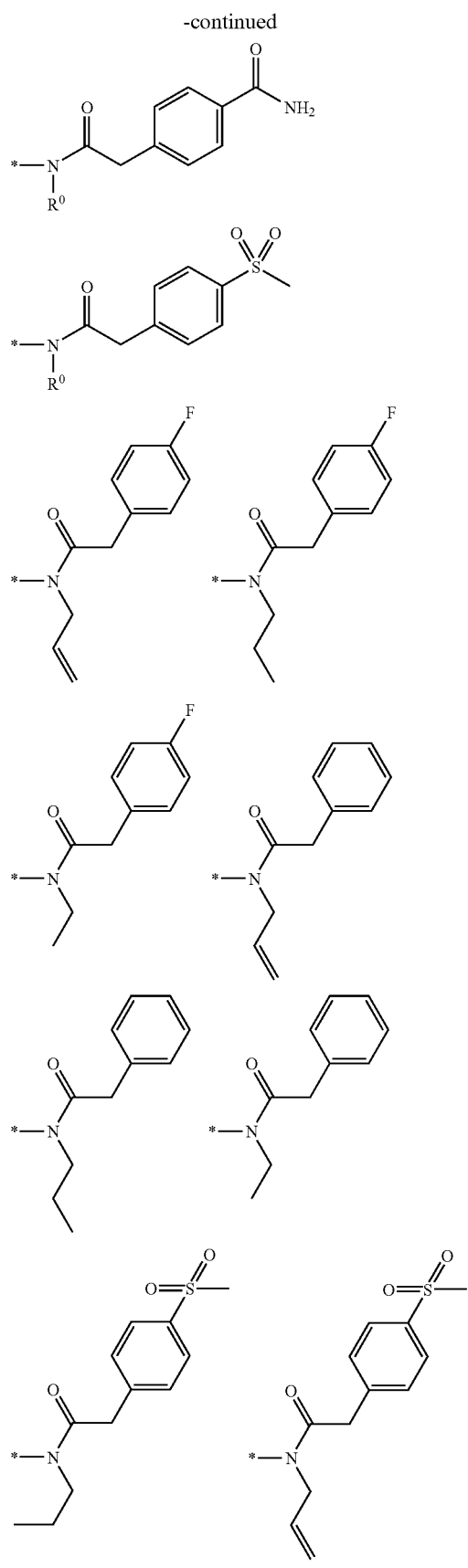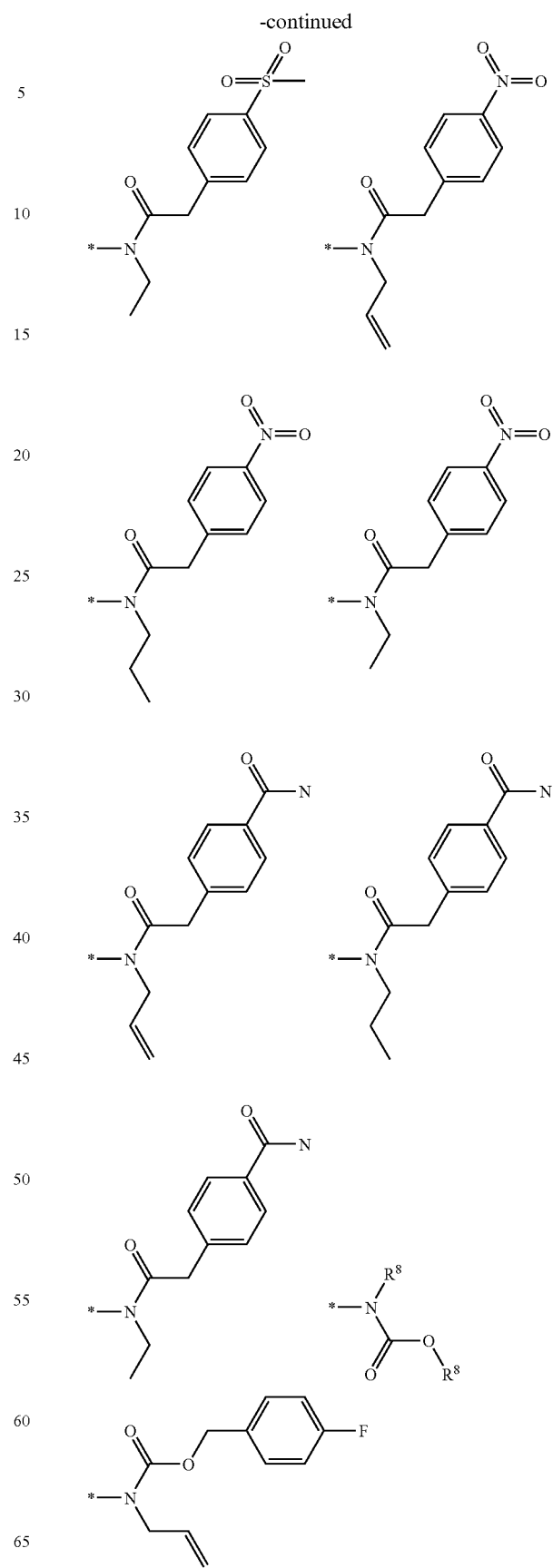

-continued
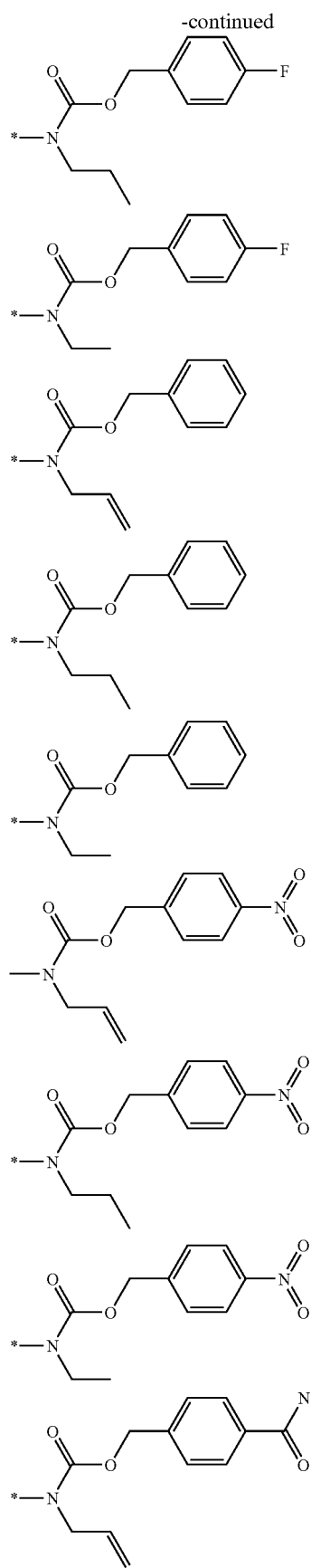
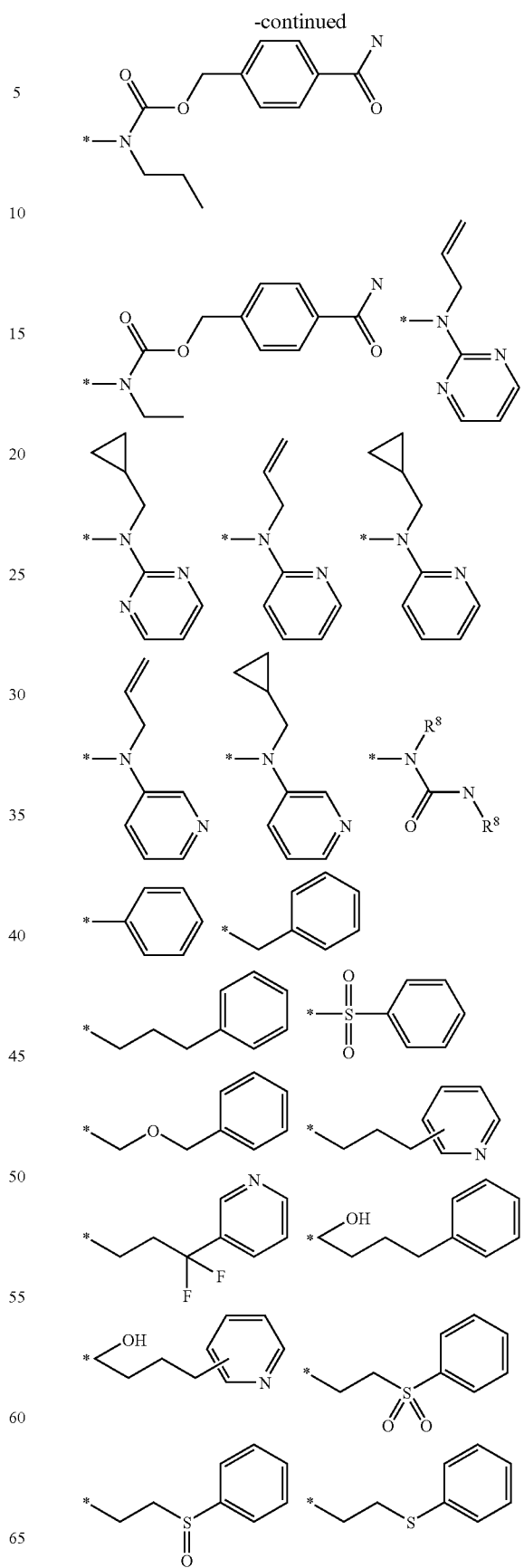

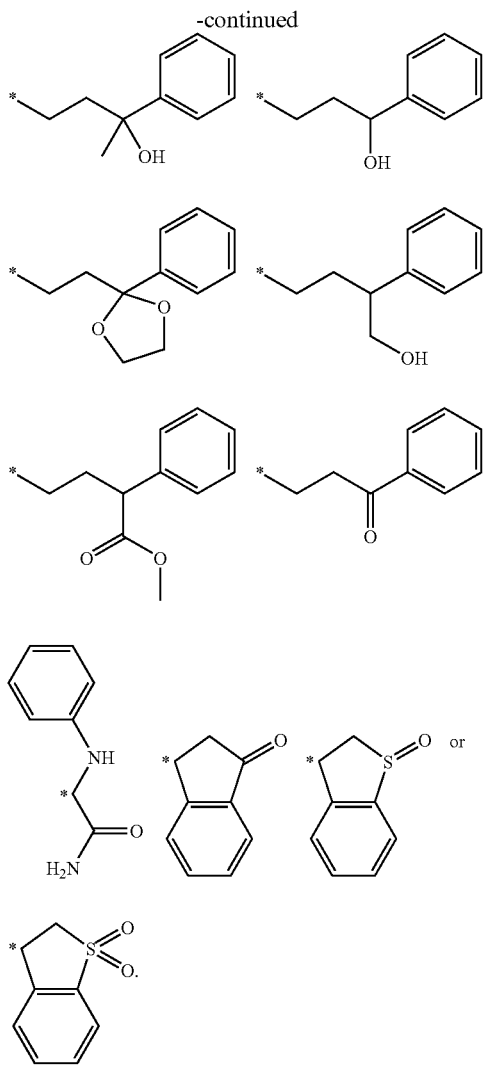
In one embodiment the ring A, with two geminal R²s, is selected from:
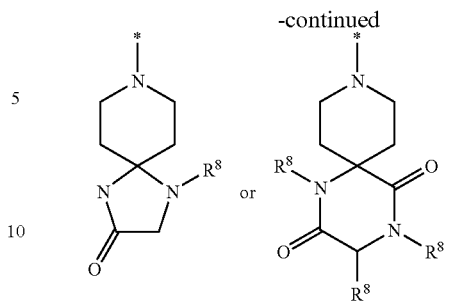
Suitably the A ring is tropane or piperidine, either optionally substituted with one or more R². Preferably, A-R² is comprised of one of the following:
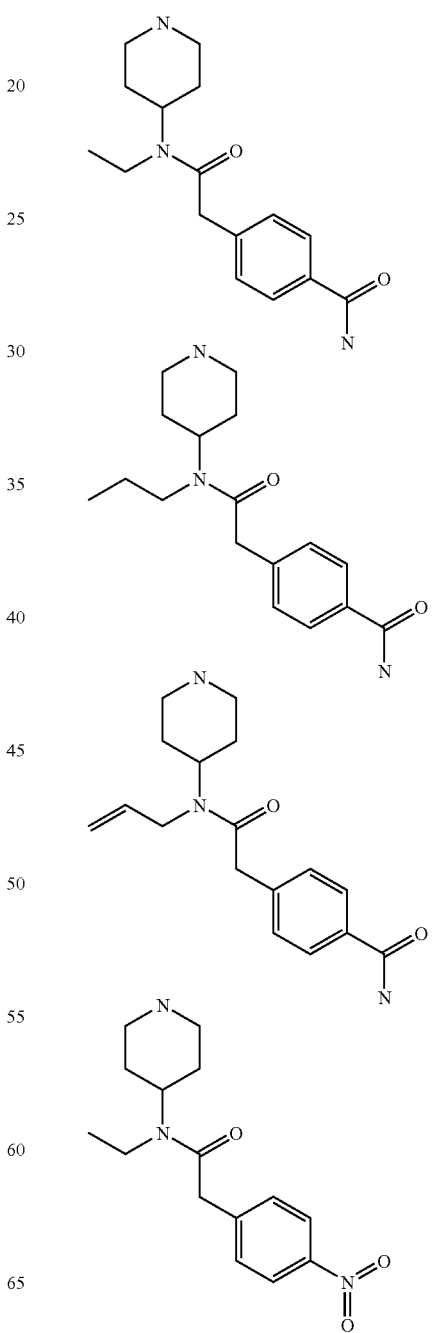

33
-continued
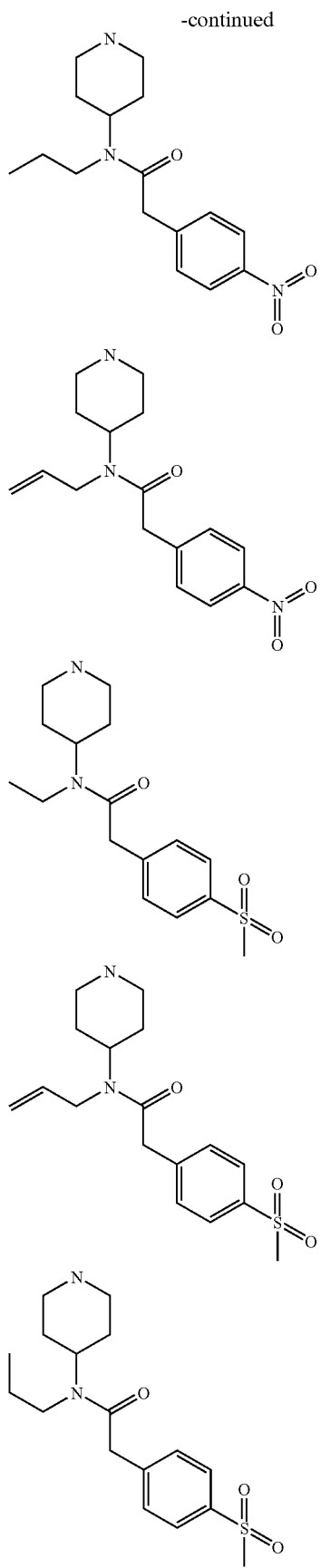
34
-continued
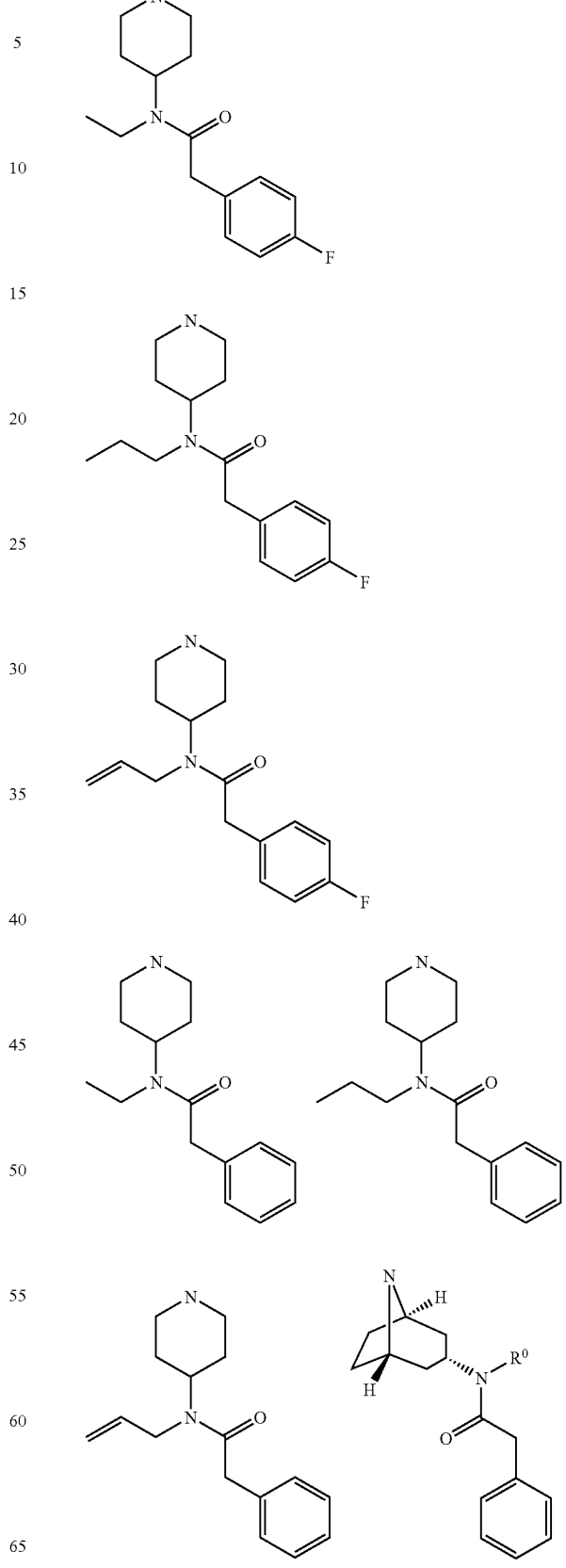

-continued
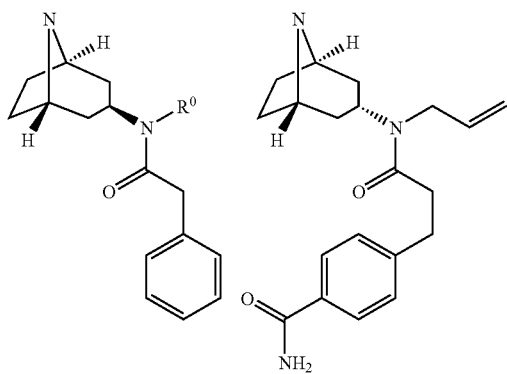
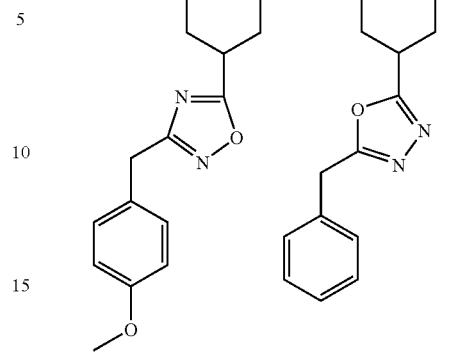
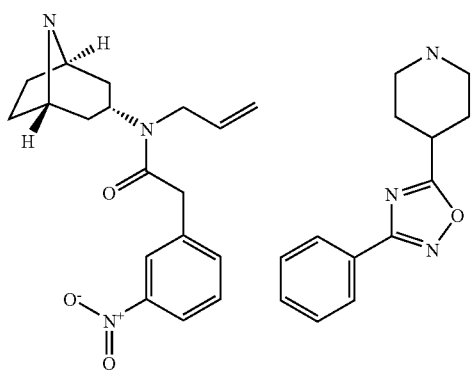
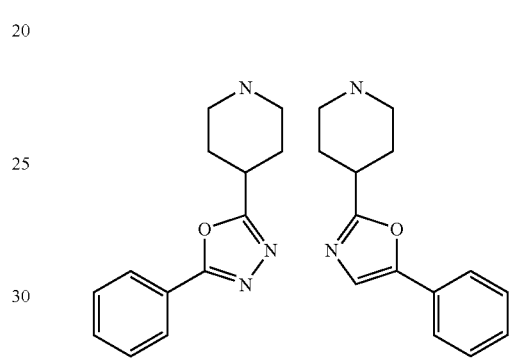
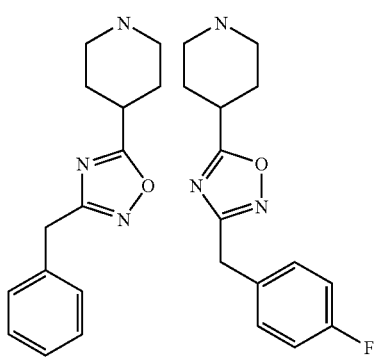
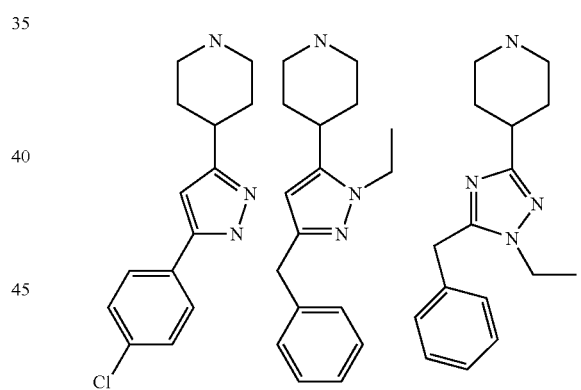
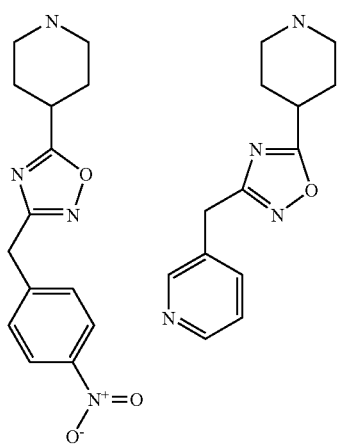
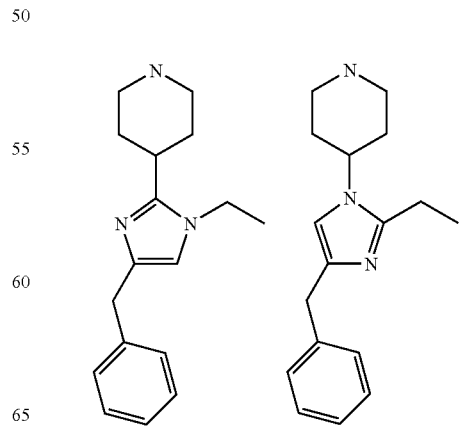

37
-continued
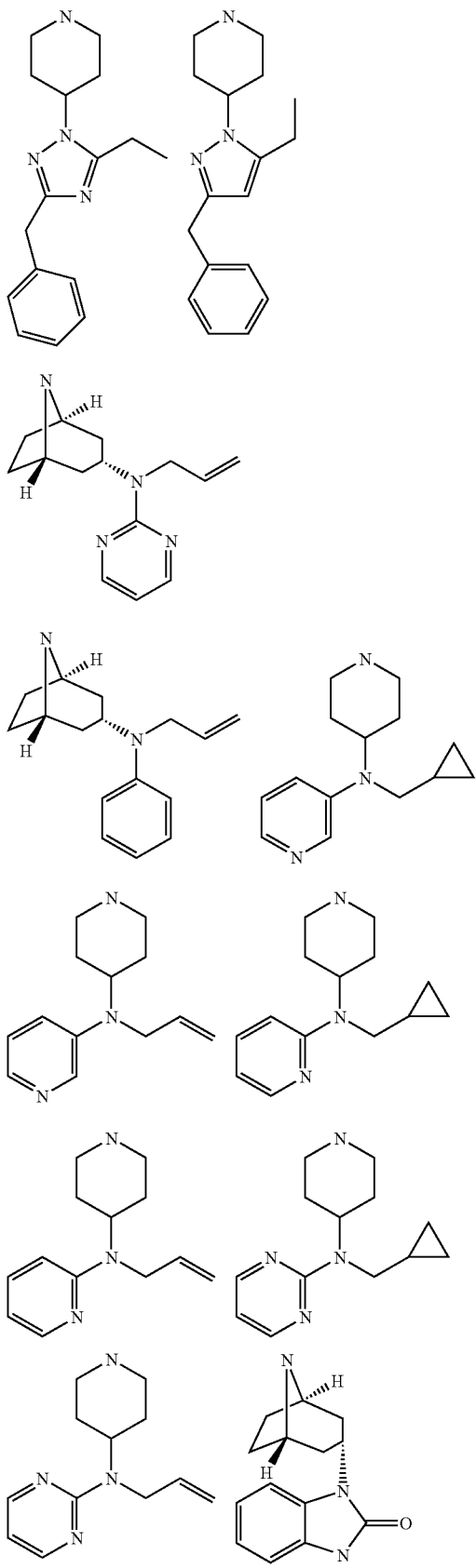
38
-continued
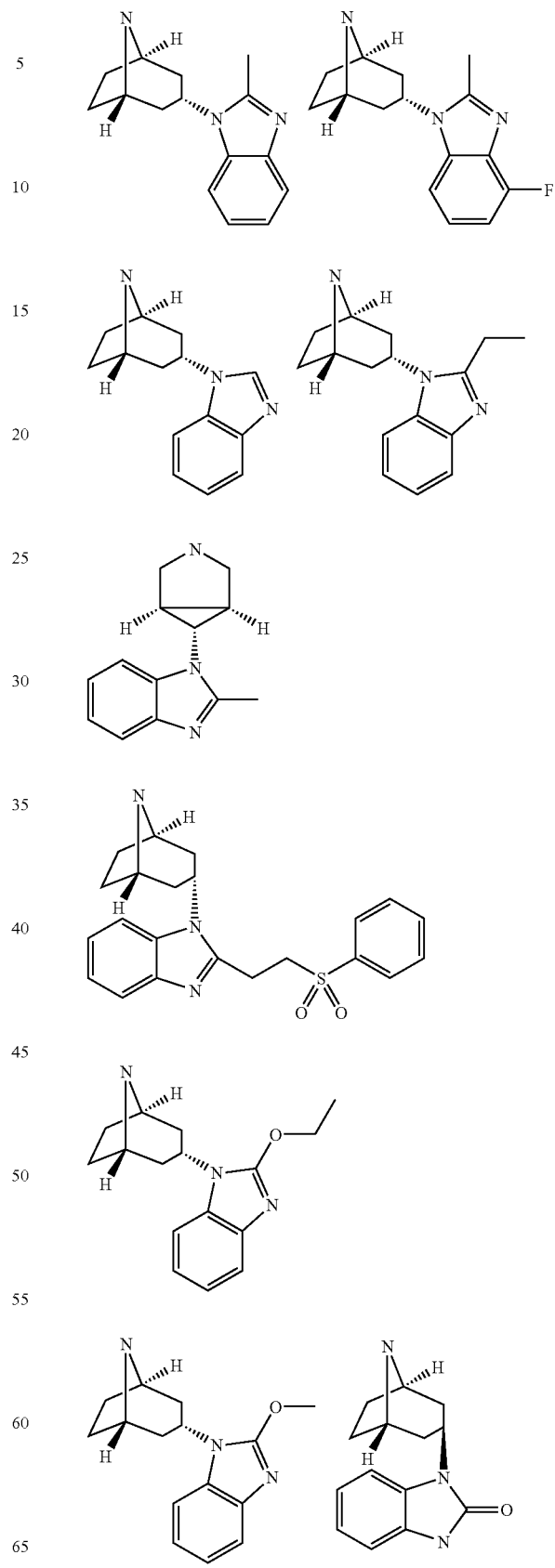

-continued
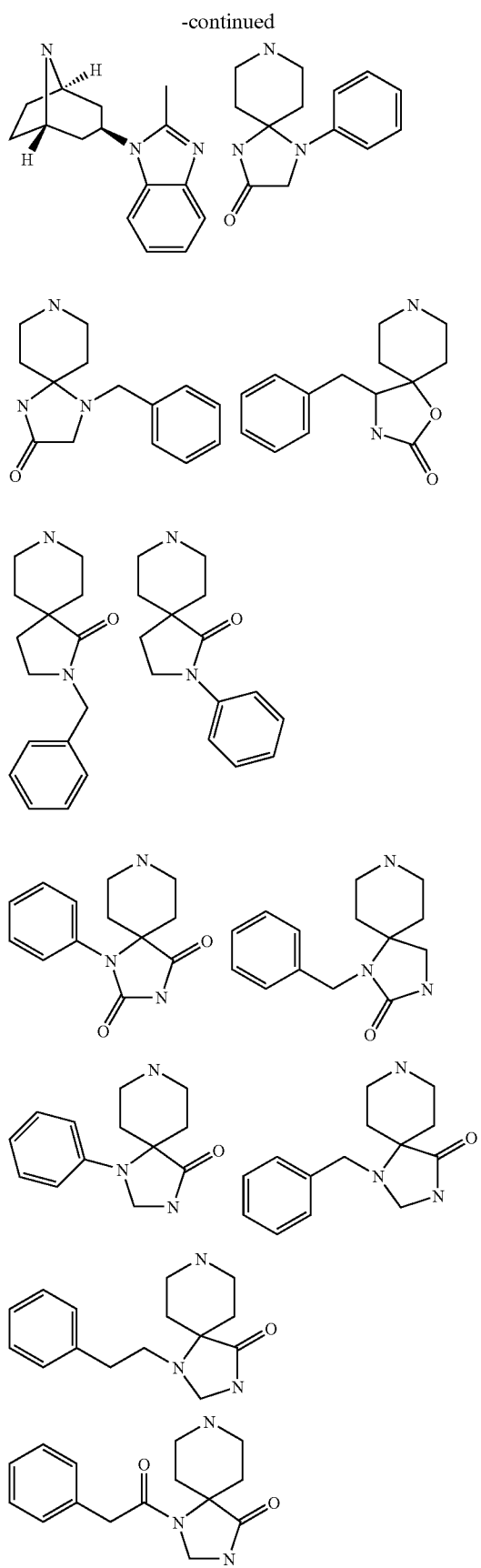
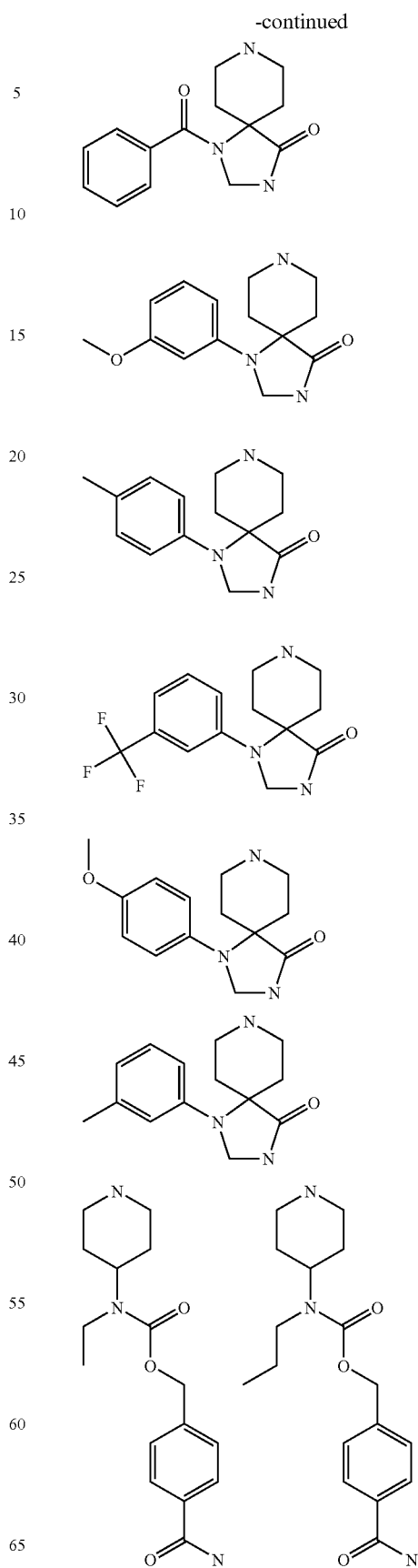

-continued
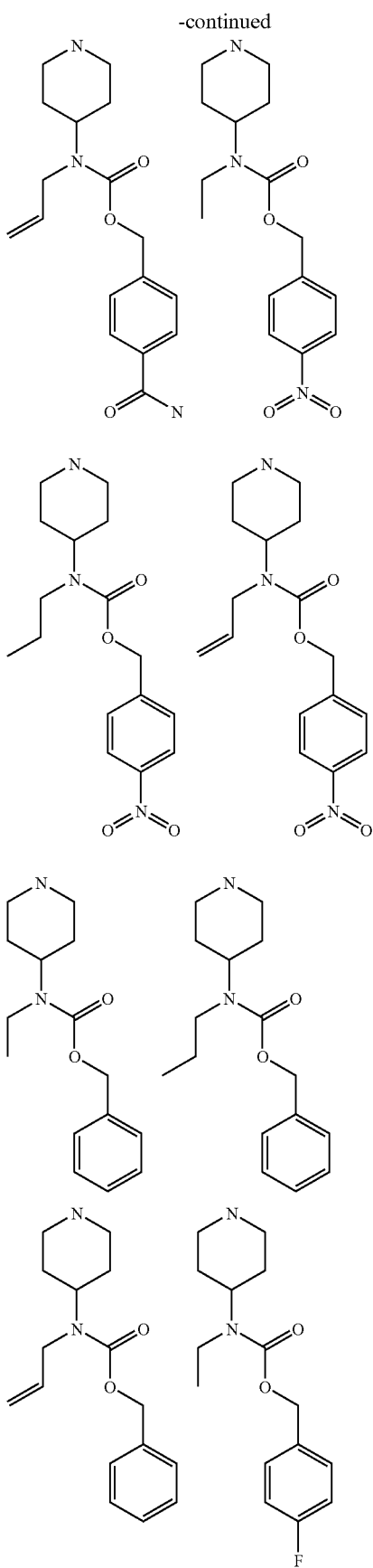
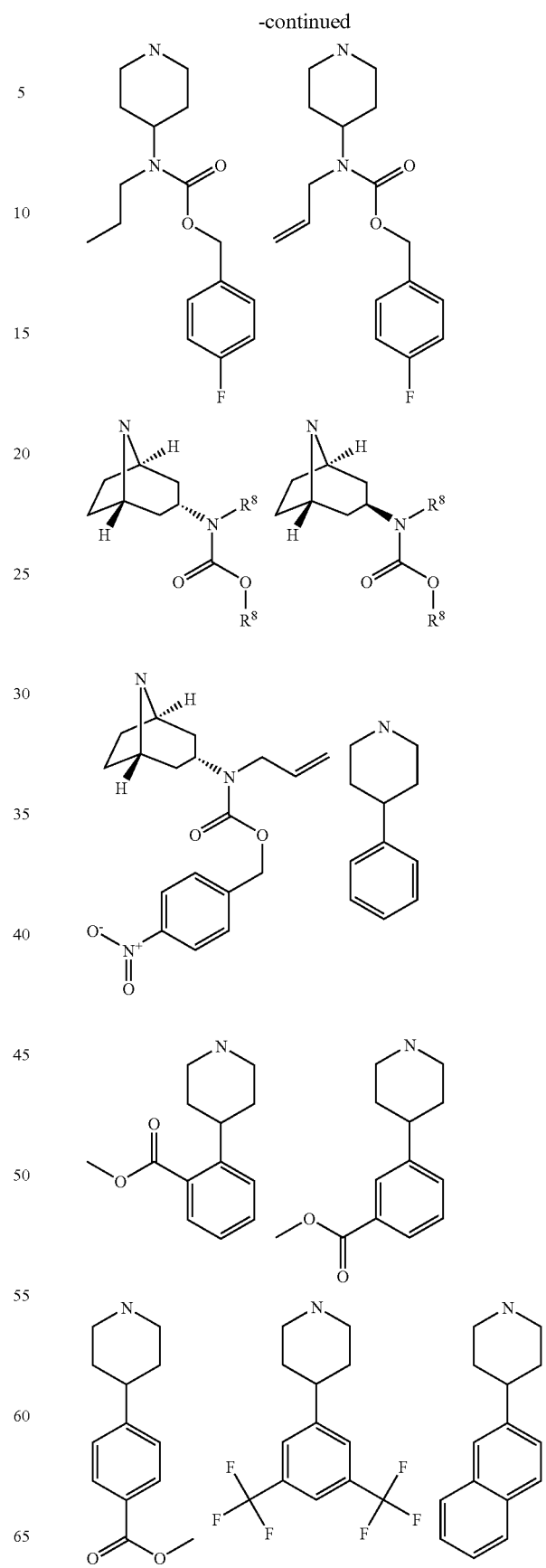

-continued
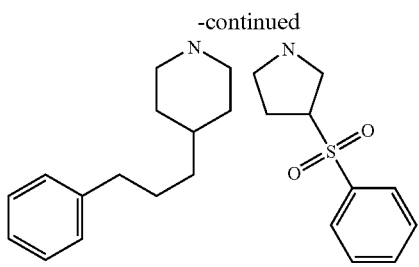
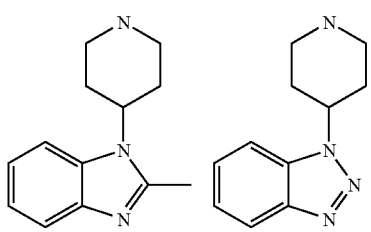
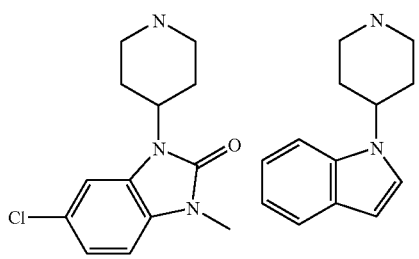
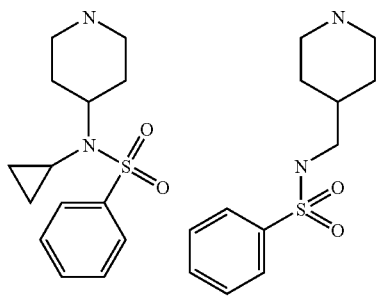
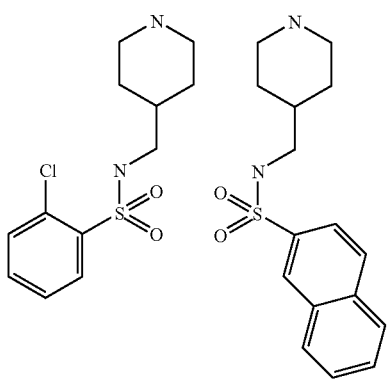
-continued
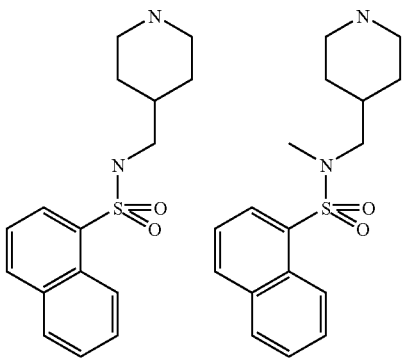
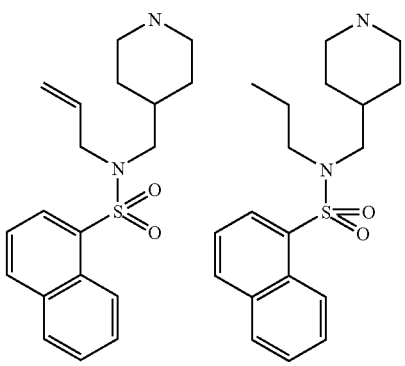
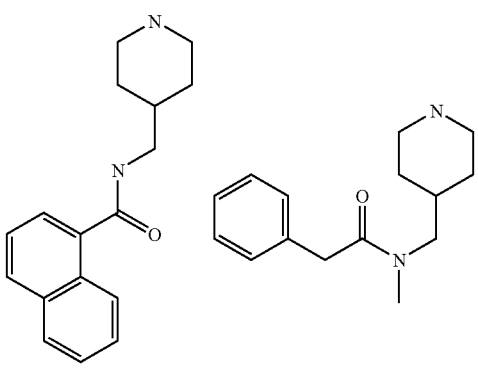
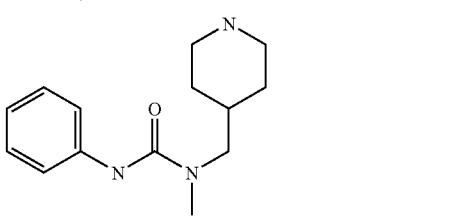
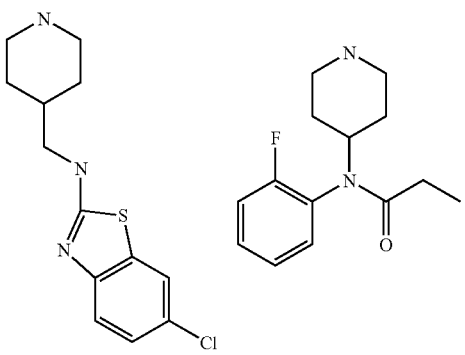

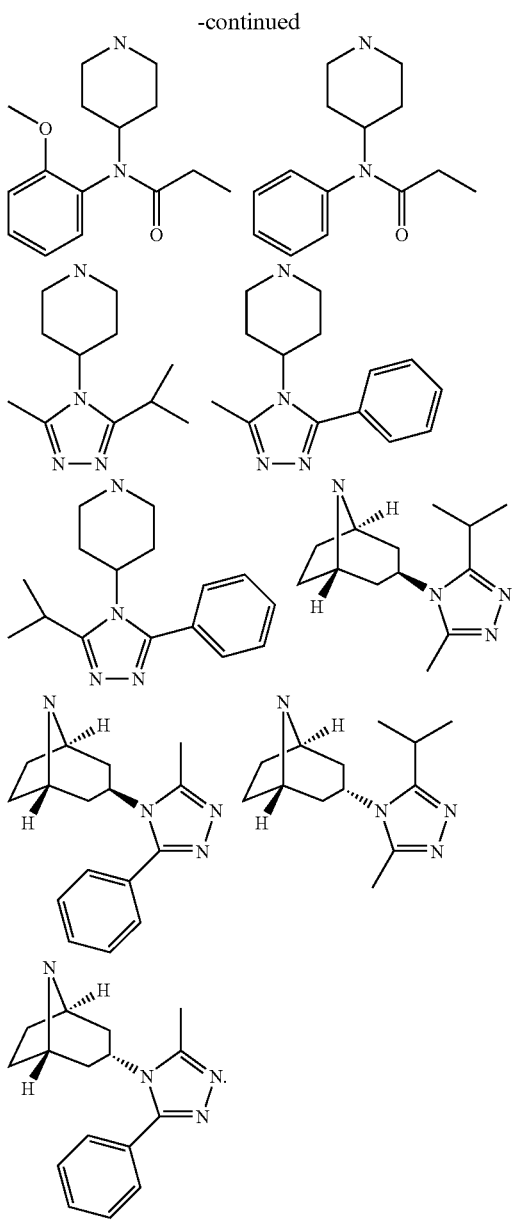

In one embodiment the A ring contains at least one additional nitrogen atom and said A ring optionally is N-substituted. Suitably the A ring is N-substituted with —(CH$_2$)$_a$—(V$_b$—R+).

Another aspect of the present invention includes a method of treatment including prevention of a viral infection in a mammal comprising administering to said mammal an antiviral effective amount of a compound of the present invention. Preferably the viral infection is an HIV infection.

Another aspect of the present invention includes a method of treatment including prevention of a bacterial infection in a mammal comprising administering to said mammal an effective amount of a compound of the present invention. Preferably the bacterium is *Yersinia pestis*.

Another aspect of the present invention includes a method of treatment including prevention of multiple sclerosis, rheumatoid arthritis, autoimmune diabetes, chronic implant rejection, asthma, rheumatoid arthritis, Crohn's Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis and immune mediated disorders in a mammal comprising administering to said mammal a pharmaceutically effective amount of a compound of the present invention.

Another aspect of the present invention includes a compound of the present invention for use in medical therapy.

Another aspect of the present invention includes the use of a compound of the present invention in the manufacture of a medicament for the treatment including prophylaxis of a viral infection. Preferably the viral infection is a HIV infection.

Another aspect of the present invention includes the use of a compound of the present invention in the manufacture of a medicament for the treatment including prophylaxis of a bacterial infection. Preferably the bacterium is *Yersinia pestis*.

Another aspect of the present invention includes the use of a compound of the present invention in the manufacture of a medicament for the treatment including prophylaxis of multiple sclerosis, rheumatoid arthritis, autoimmune diabetes, chronic implant rejection, asthma, rheumatoid arthritis, Crohn's Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis and immune mediated disorders.

Another aspect of the present invention includes a pharmaceutical composition comprising a pharmaceutically effective amount of a compound of the present invention together with a pharmaceutically acceptable carrier. Preferably the pharmaceutical composition is in the form of a tablet, a capsule, or a liquid.

Another aspect of the present invention includes a method of treatment including prevention of a viral infection in a mammal comprising administering to said mammal a composition comprising a compound of the present invention and another therapeutic agent. Preferably the composition comprises one or more therapeutic agent selected from the group consisting of (1-alpha, 2-beta, 3-alpha)-9-[2,3-bis(hydroxymethyl) cyclobutyl]guanine [(−)BHCG, SQ-34514, lobucavir], 9-[(2R,3R,4S)-3,4-bis(hydroxymethyl)-2-oxetanosyl]adenine (oxetanocin-G), acyclic nucleosides, acyclovir, valaciclovir, famciclovir, ganciclovir, penciclovir, acyclic nucleoside phosphonates, (S)-1-(3-hydroxy-2-phosphonylmethoxypropyl)cytosine (HPMPC), [[[2-(6-amino-9H-purin-9-yl)ethoxy]methyl]phosphinylidene] bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), (R)-[[2-(6-Amino-9H-purin-9-yl)-1-methylethoxy]methyl]phosphonic acid bis-(isopropoxycarbonyloxymethyl)ester (bis-POC-PMPA), ribonucleotide reductase inhibitors, 2-acetylpyridine 5-[(2-chloroanilino)thiocarbonyl] thiocarbonohydrazone and hydroxyurea, nucleoside reverse transcriptase inhibitors, 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (–)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (–)-cis-4-[2-amino-6-(cyclopropylamino)-9H-purin-9-yl]-2-cyclopentene-1-methanol (abacavir), 9-[4-hydroxy-2-(hydroxymethyl)but-1-yl]-guanine (H2G), ABT-606 (2HM-H2G) ribavirin, protease inhibitors, indinavir, ritonavir, nelfinavir, amprenavir, saquinavir, fosamprenavir, (R)-N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272), 4R-(4alpha,5alpha,6beta)]-1,3-bis[(3-aminophenyl)methyl]hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-I-tert-leucylamino]-4-phenylbutyl-N alpha-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl) thiazolidine-4(R)-carboxamide (AG-1776), N-(2(R)-hydroxy-1(S)-indanyl)-2(R)-phenyl-methyl-4(S)-hydroxy-5-(1-(1-(4-benzo[b]furanylmethyl)-2(S)-N'-(tert-butylcarboxamido)piperazinyl)pentanamide (MK-944A), interferons, α-interferon, renal excretion inhibitors, probenecid, nucleoside transport inhibitors, dipyridamole, pentoxifylline, N-acetylcysteine (NAC), Procysteine, α-trichosanthin, phosphonoformic acid, immunomodulators, interleukin II, thymosin, granulocyte macrophage colony stimulating factors, erythropoetin, soluble $CD_4$ and genetically engineered derivatives thereof, non-nucleoside reverse transcriptase inhibitors (NNRTIs), nevirapine (BI-RG-587), alpha-((2-acetyl-5-methylphenyl)amino)-2,6-dichloro-benzeneacetamide (loviride), 1-[3-(isopropylamino)-2-pyridyl]-4-[5-(methanesulfonamido)-1H-indol-2-ylcarbonyl]piperazine monomethanesulfonate (delavirdine), (10R,11S,12S)-12-hydroxy-6,6,10,11-tetramethyl-4-propyl-11,12-dihydro-2H, 6H, 10H-benzo(1, 2-b:3, 4-b':5, 6-b")tripyran-2-one ((+) calanolide A), (4S)-6-Chloro-4-[1E)-cyclopropylethenyl)-3, 4-dihydro-4-(trifluoromethyl)-2(1H)-quinazolinone (DPC-083), (S)-6-chloro-4-(cyclopropylethynyl)-1,4-dihydro-4-(trifluoromethyl)-2H-3,1-benzoxazin-2-one (efavirenz, DMP 266), 1-(ethoxymethyl)-5-(1-methylethyl)-6-(phenylmethyl)-2,4(1H,3H)-pyrimidinedione (MKC442), and 5-(3, 5-dichlorophenyl)thio-4-isopropyl-1-(4-pyridyl)methyl-1H-imidazol-2-ylmethyl carbamate (capravirine), glycoprotein 120 antagonists, PRO-2000, PRO-542, 1,4-bis[3-[(2, 4-dichlorophenyl)carbonylamino]-2-oxo-5,8-disodiumsulfanyl]naphthalyl-2, 5-dimethoxyphenyl-1, 4-dihydrazone (FP-21399), cytokine antagonists, reticulose (Product-R), 1,1'-azobis-formamide (ADA), 1,11-(1,4-phenylenebis(methylene))bis-1,4,8,11-tetraazacyclotetradecane octahydrochloride (AMD-3100), integrase inhibitors, and fusion inhibitors.

Another aspect of the present invention includes a method of treatment or prevention of a viral infection in a mammal comprising administering to said mammal a composition comprising a compound of the present invention and ritonavir.

Particular compounds of the present invention include:

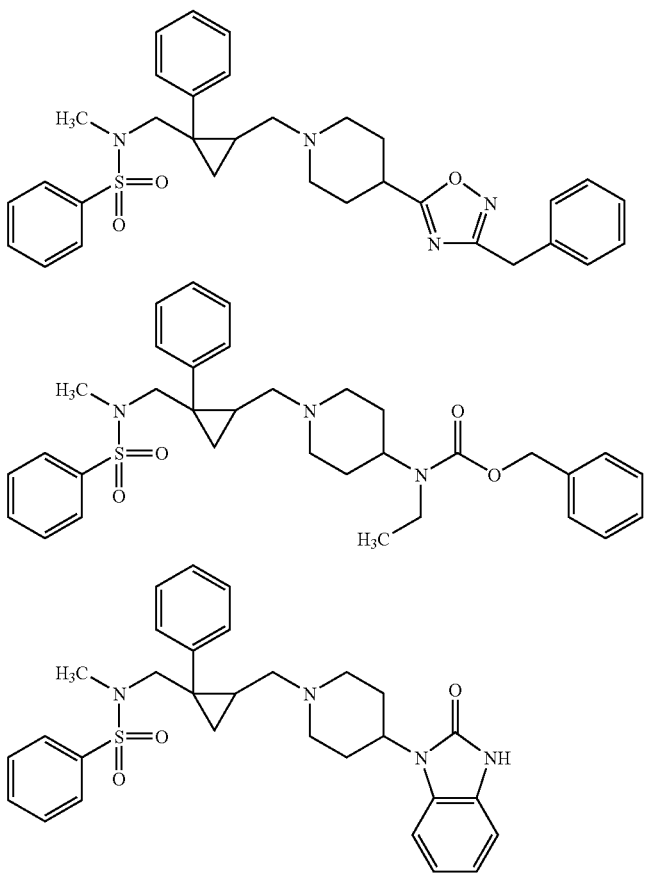

-continued
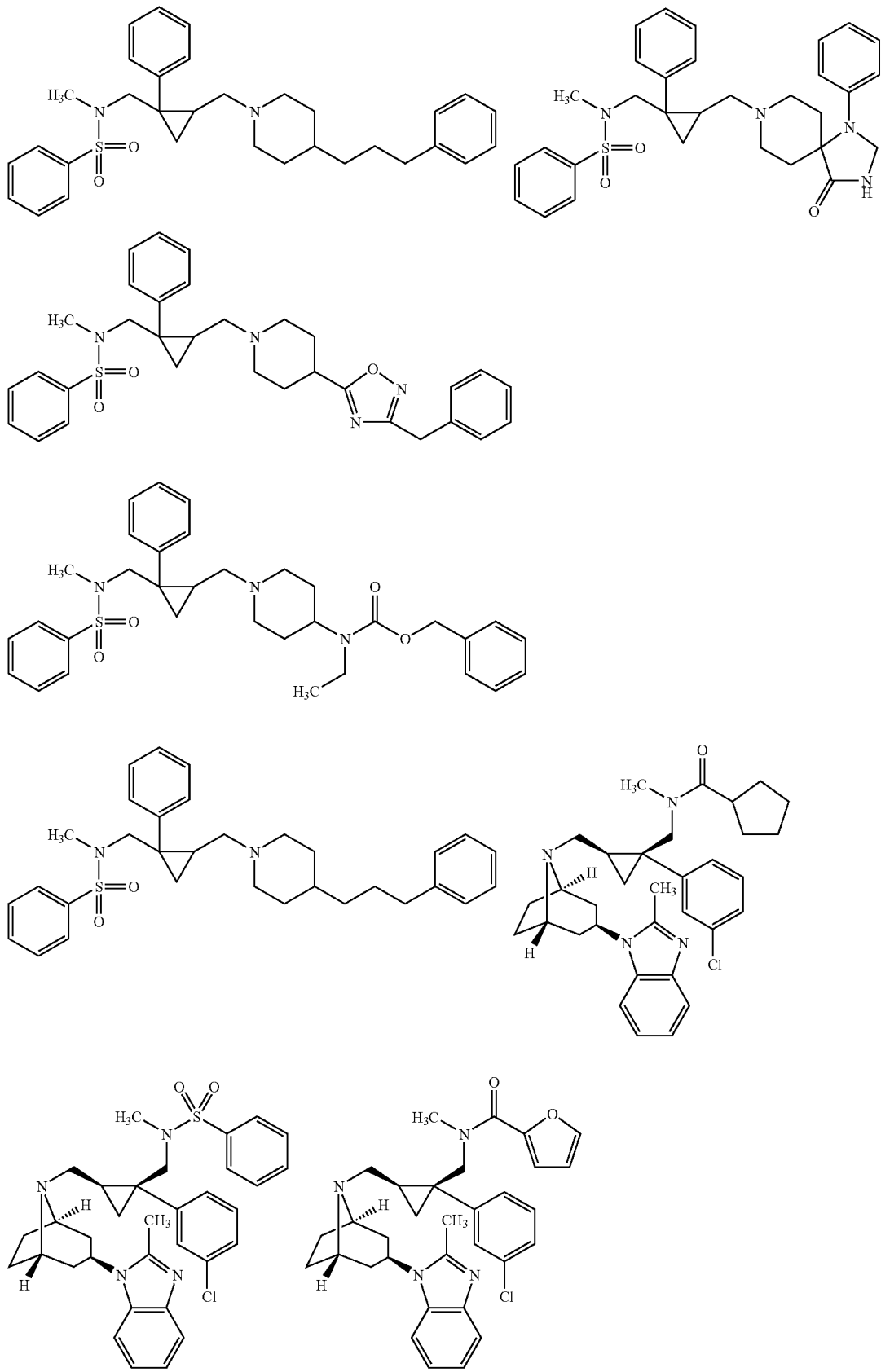

-continued
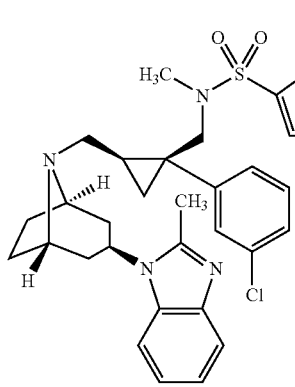
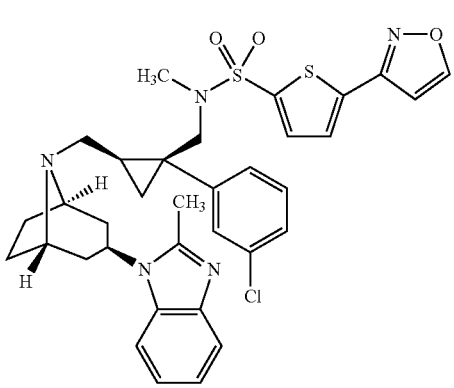
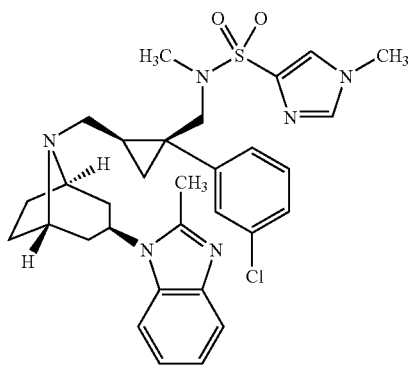
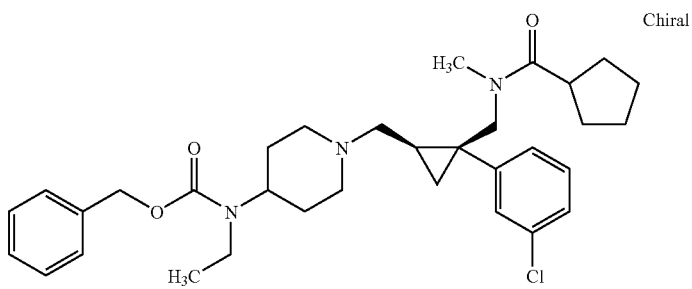
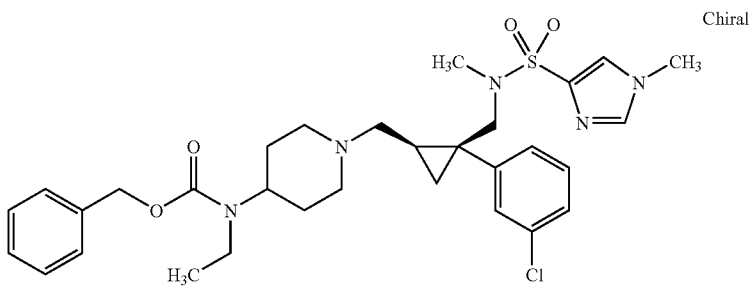
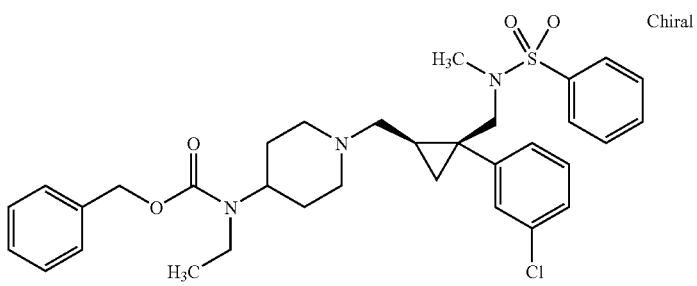
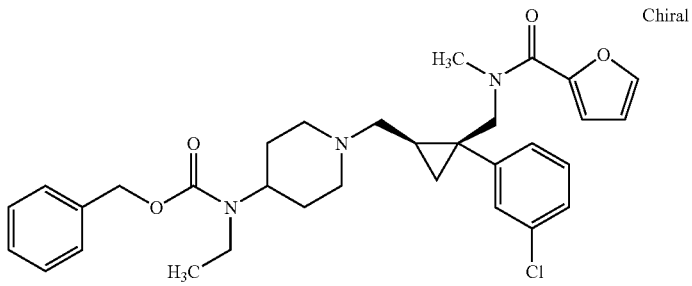

-continued
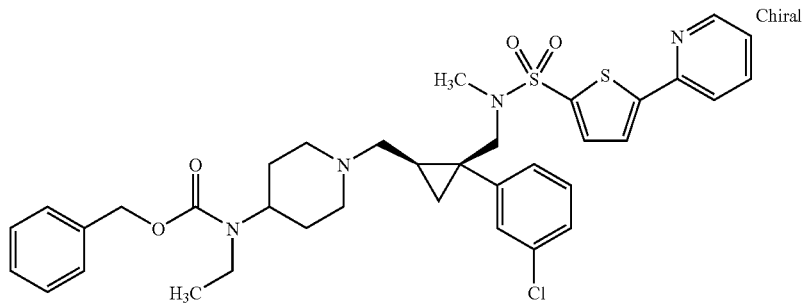
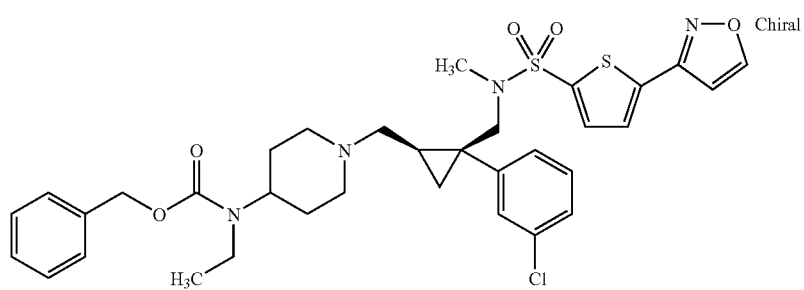
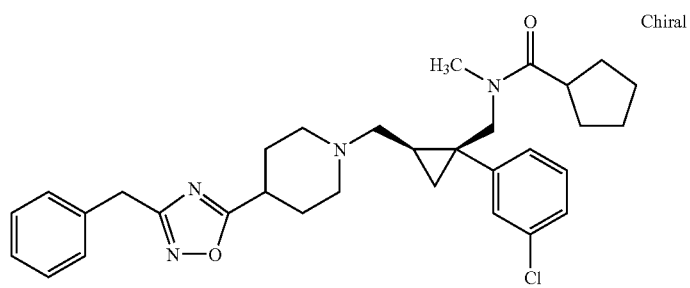
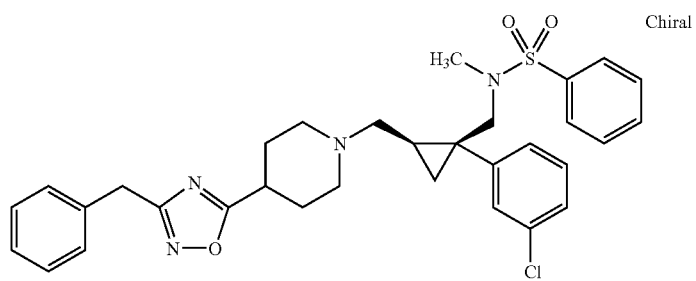
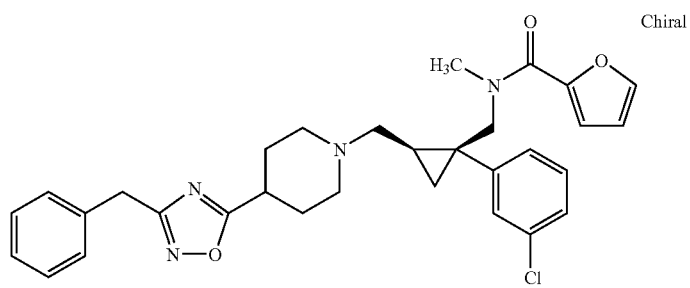

-continued
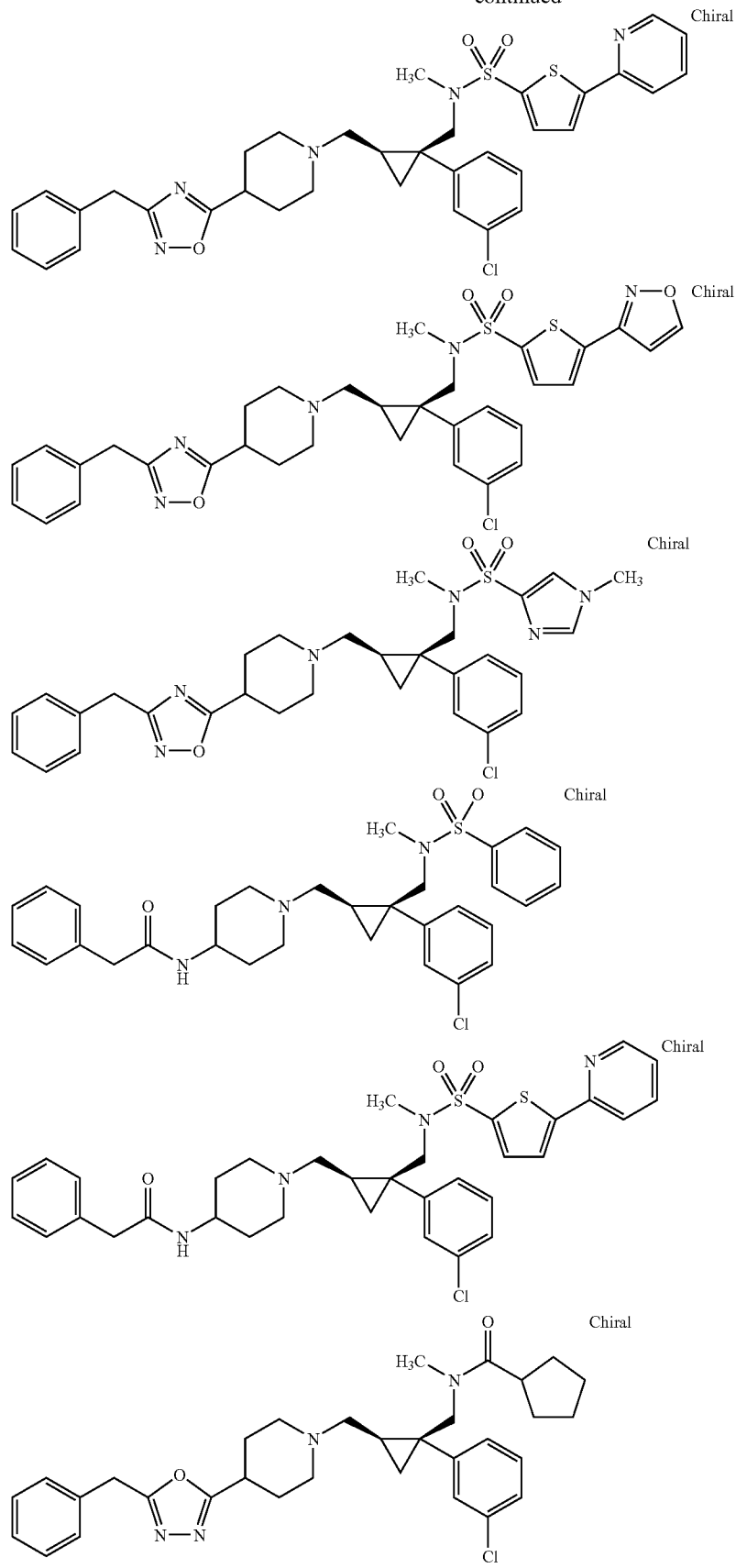

-continued
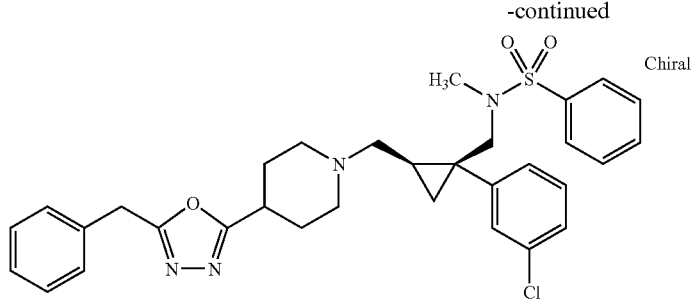
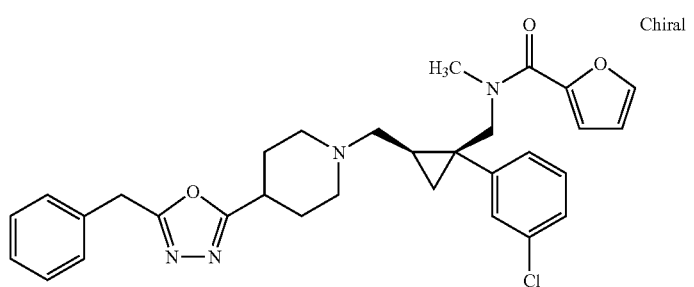
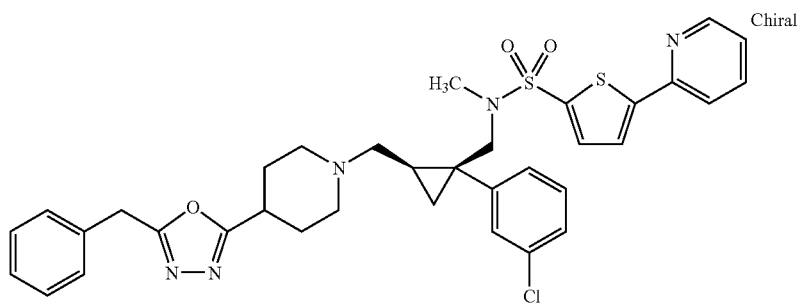
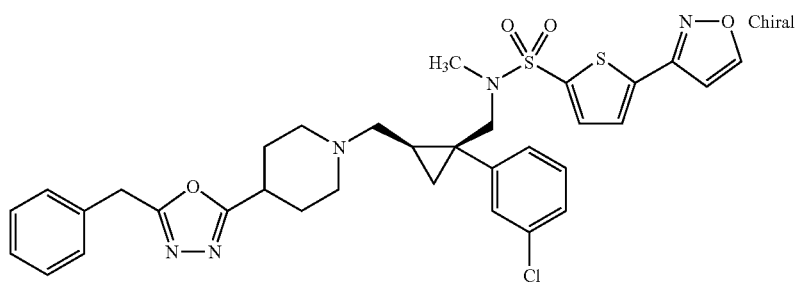
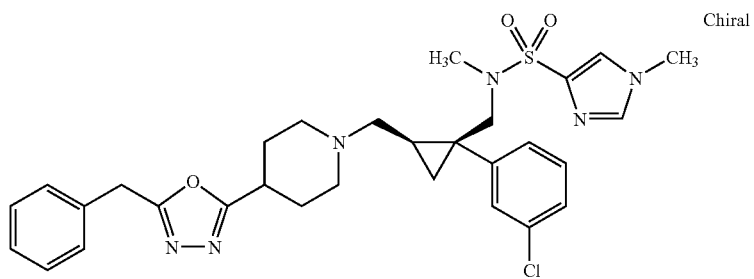

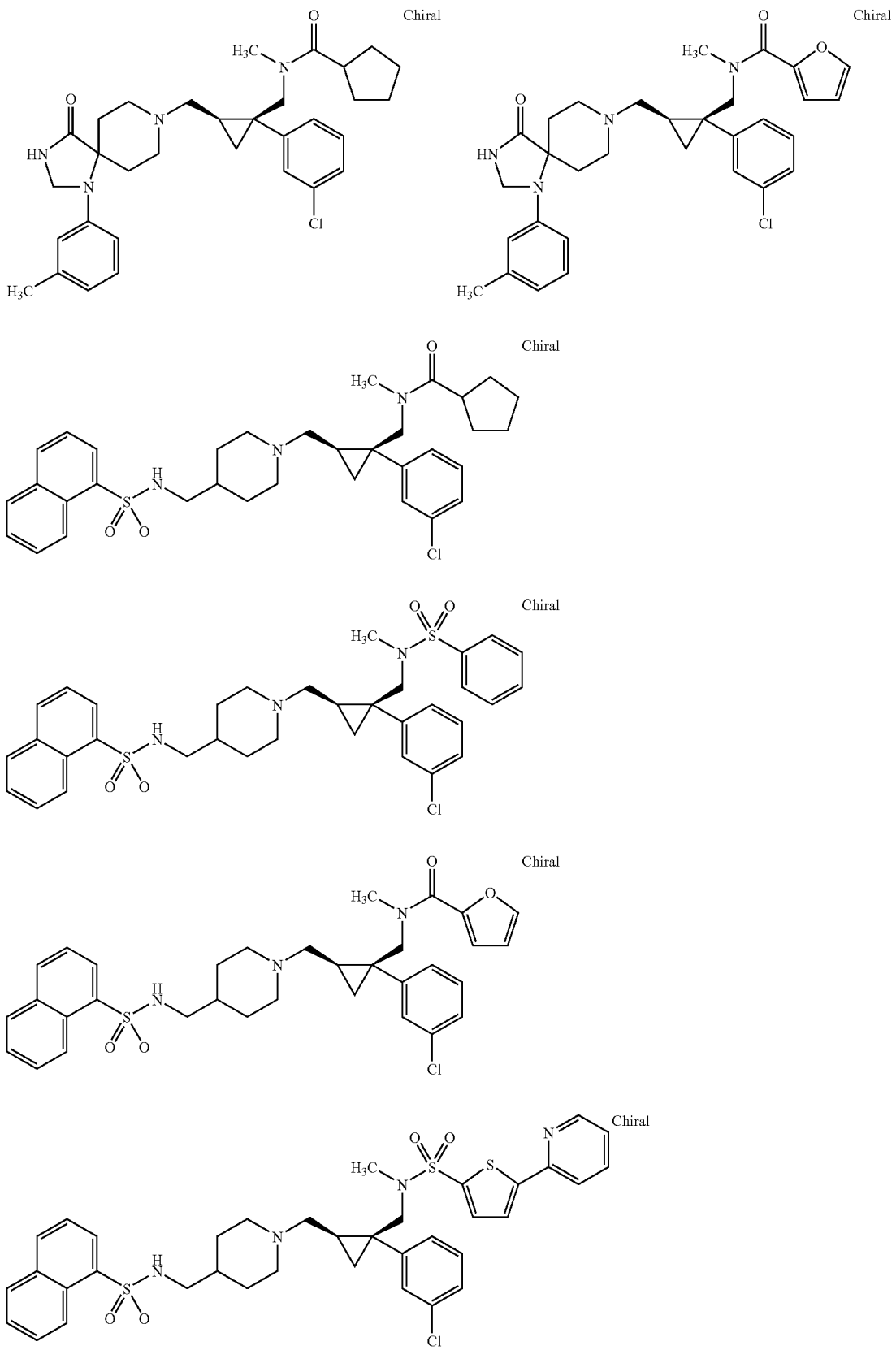

-continued
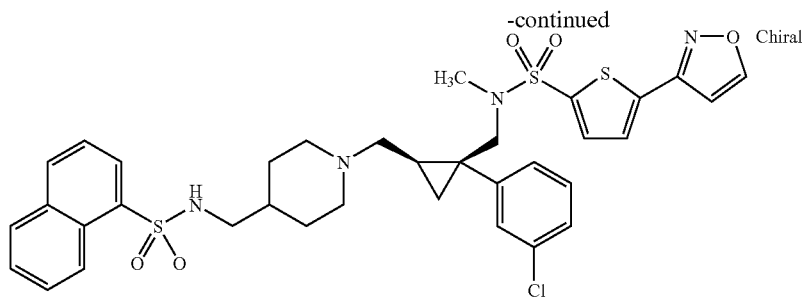
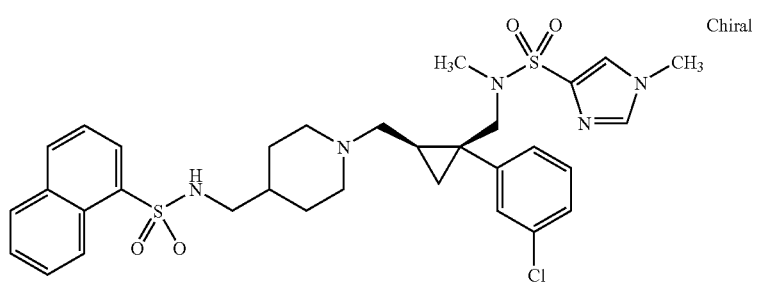
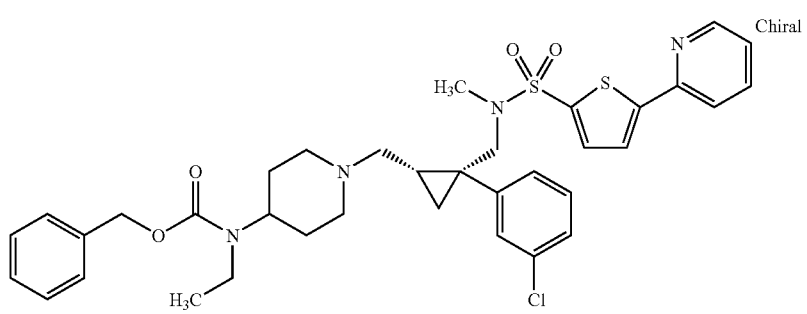
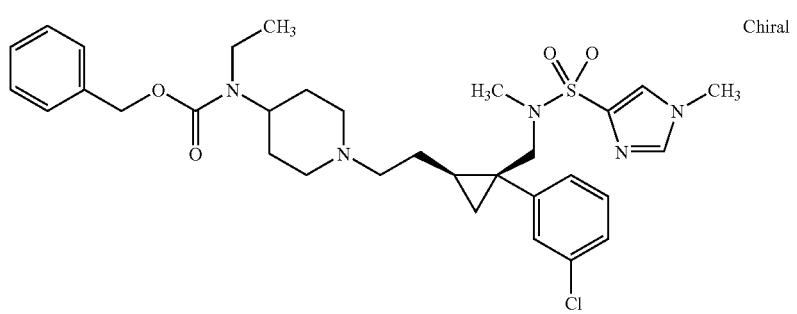
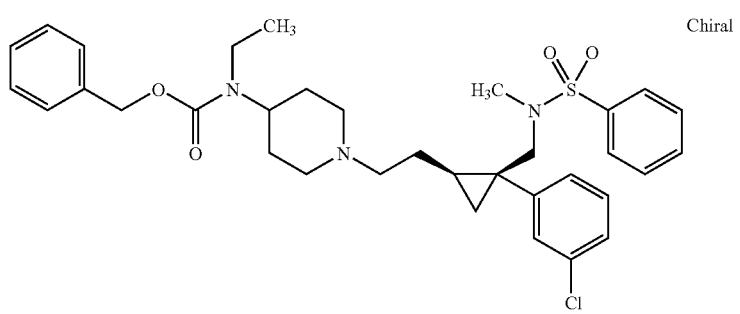

-continued
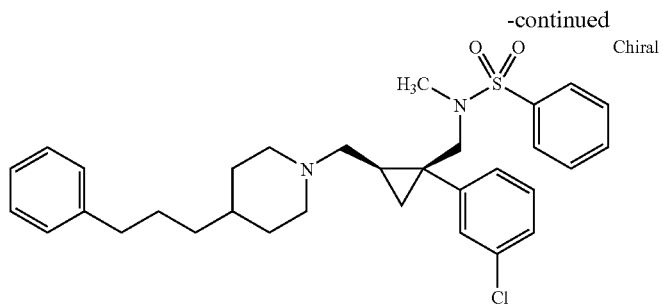
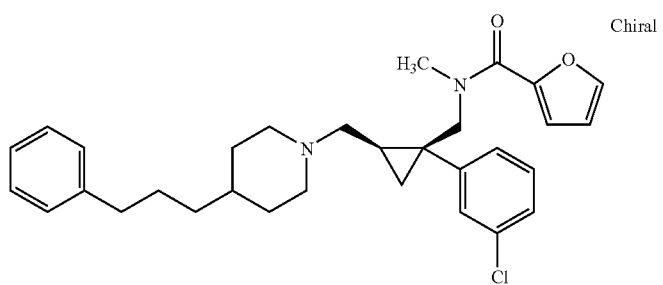
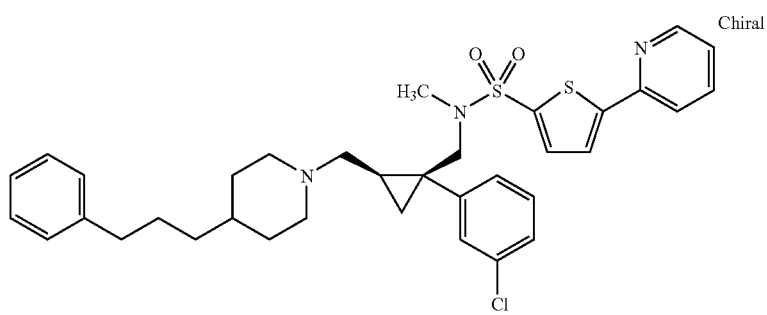
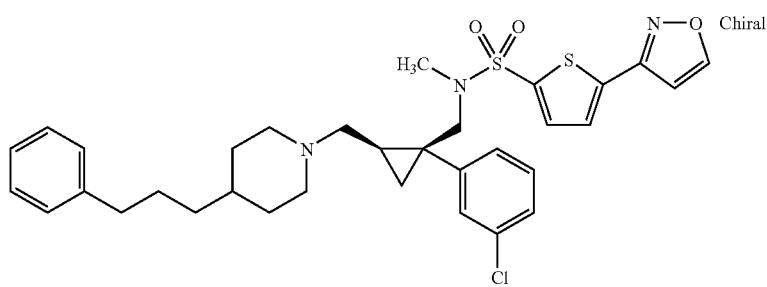
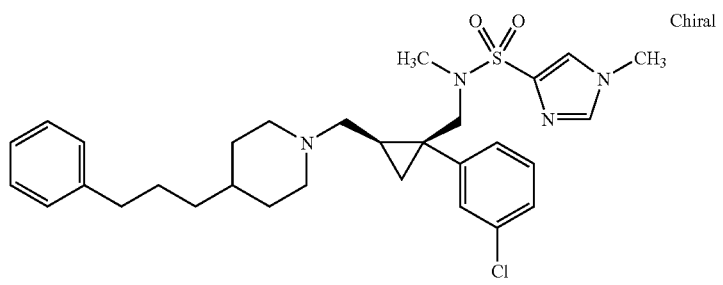

-continued
65 66
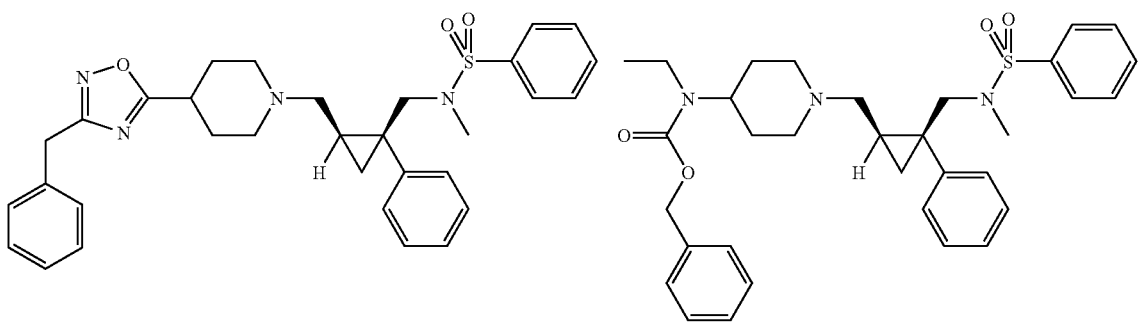
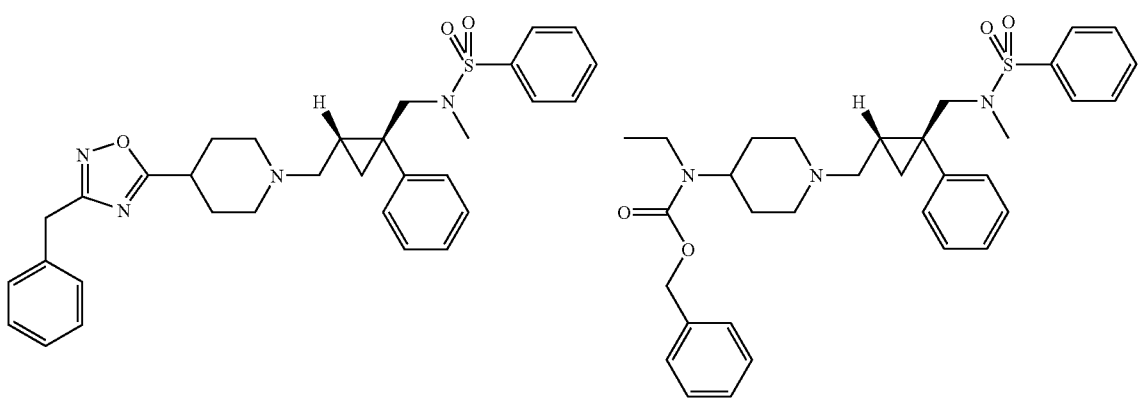
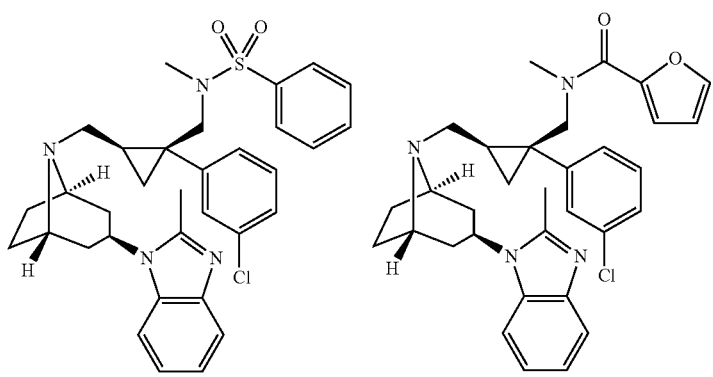
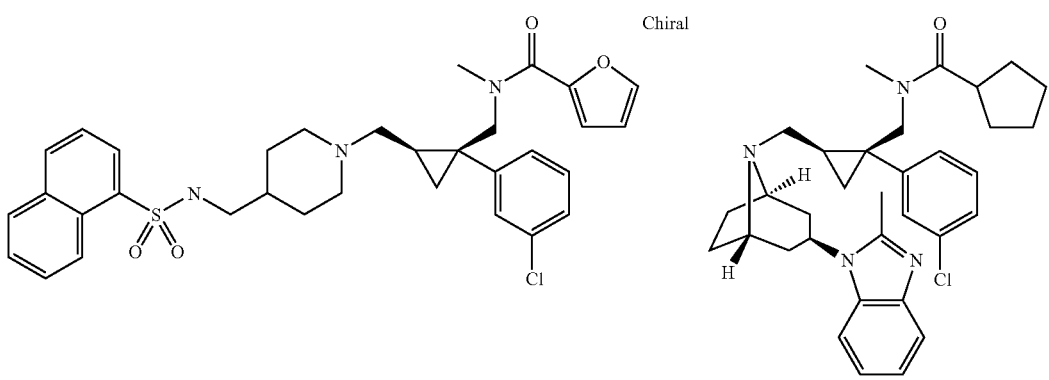

-continued

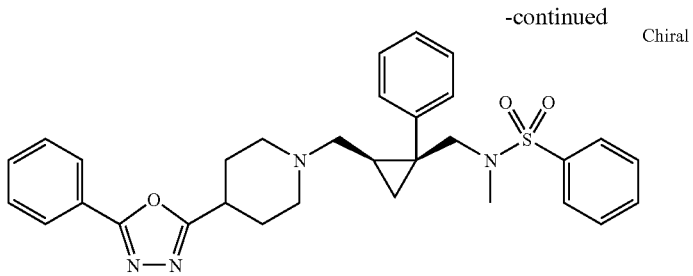
Chiral

DETAILED DESCRIPTION OF THE INVENTION

The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "cycloalkyl", "carbocylyl", "carbocyclic", or "carbocycle", or "carbocyclo", alone or in combination with any other term, refers to a monocyclic or polycyclic non-aromatic hydrocarbon ring radical having three to twenty carbon atoms, preferably from three to twelve carbon atoms, and more preferably from three to ten carbon atoms. If polycyclic, each ring in a carbocylyl radical is non-aromatic unless otherwise indicated. A carbocylyl radical is either completely saturated or contains one or more units of unsaturation but is not aromatic. The unsaturation, if present, may occur in any point in the ring that may result in any chemically stable configuration. The term "cycloalkyl", "carbocylyl", "carbocyclic", or "carbocycle", or "carbocyclo" also includes hydrocarbon rings that are fused to one or more aromatic rings, such as in tetrahydronaphthyl, where the radical or point of attachment is on the non-aromatic ring.

Unless otherwise indicated, the term "cycloalkyl", "carbocylyl", "carbocyclic", or "carbocycle", or "carbocyclo" also includes each possible positional isomer of a non-aromatic hydrocarbon radical, such as in 1-decahydronaphthyl, 2-decahydronaphthyl, 1-tetrahydronaphthyl and 2-tetrahydronaphthyl. Examples of suitable cycloalkyl groups include, but are not limited to, cyclopropyl, cyclobutyl, cyclopentyl, cyclohexyl, cyclohexenyl, decahydronaphthyl, tetrahydronaphthyl and the like.

The term "alkenyl," alone or in combination with any other term, refers to a straight-chain or branched-chain alkyl group with at least one carbon-carbon double bond. Examples of alkenyl radicals include, but are not limited to, ethenyl, propenyl, isopropenyl, butenyl, isobutenyl, pentenyl, hexenyl, hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl", alone or in combination with any other term, refers to an aromatic monocyclic or polycyclic hydrocarbon ring radical containing five to twenty carbon atoms, preferably from six to fourteen carbon atoms, and more preferably from six to ten carbon atoms. Also included within the scope of the term "aryl", as it is used herein, is a group in which an aromatic hydrocarbon ring is fused to one or more non-aromatic carbocyclic or heteroatom-containing rings, such as in an indanyl, phenanthridinyl or tetrahydronaphthyl, where the radical or point of attachment is on the aromatic hydrocarbon ring.

Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "aralkyl" further refers to groups of —$R_aR_b$, where $R_a$ is an alkylene as defined herein and $R_b$ is an aryl as defined herein.

The term "heterocycle", "heterocyclic", and "heterocyclyl", alone or in combination with any other term, refers to a non-aromatic monocyclic or polycyclic ring radical containing three to twenty carbon atoms, preferably three to seven carbon atoms if monocyclic and eight to eleven carbon atoms if bicyclic, and in which one or more ring carbons, preferably one to four, are each replaced by a heteroatom such as N, O, and S. If polycyclic, each ring in a heterocyclyl radical is non-aromatic unless otherwise indicated. A heterocyclic ring may be fully saturated or may contain one or more units of unsaturation but is not aromatic. The unsaturation, if present, may occur in any point in the ring that may result in any chemically stable configuration. The heterocyclic ring may be attached at a carbon or heteroatom that results in the creation of a stable structure. Preferred heterocycles include 5-7 membered monocyclic heterocycles and 8-10 membered bicyclic heterocycles.

Also included within the scope of the term "heterocycle", "heterocyclic", or "heterocyclyl" is a group in which a non-aromatic heteroatom-containing ring is fused to one or more aromatic rings, such as in an indolinyl, chromanyl, phenanthridinyl or tetrahydroquinolinyl, where the radical or point of attachment is on the non-aromatic heteroatom-containing ring. Unless otherwise indicated, the term "heterocycle", "heterocyclic", or "heterocyclyl" also includes each possible positional isomer of a heterocyclic radical, such as in 1-decahydroquinoline, 2-decahydroquinoline, 3-decahydroquinoline, 4-decahydroquinoline, 5-decahydroquinoline, 6-decahydroquinoline, 7-decahydroquinoline, 7-decahydroquinoline, 8-decahydroquinoline, 4a-decahydroquinoline, 8a-decahydroquinoline, 1-indolinyl, 2-indolinyl, 3-indolinyl, 1-tetrahydroquinoline, 2-tetrahydroquinoline, 3-tetrahydroquinoline and 4-tetrahydroquinoline. The term "heterocyclylalkyl" refers to an alkyl group substituted by a heterocyclyl.

Examples of heterocyclic groups include, but are not limited to, imidazolinyl, 2,3-dihydro-1H-imidazolyl, imidazolidinyl, indazolinolyl, perhydropyridazyl, pyrrolinyl, pyrrolidinyl, 4H-pyrazolyl, piperidinyl, pyranyl, pyrazolinyl, piperazinyl, morpholinyl, thiamorpholinyl, thiazolidinyl, thiamorpholinyl, oxopiperidinyl, oxopyrrolidinyl, azepinyl, tetrahydrofuranyl, oxoazepinyl, tetrahydropyranyl, thiazolyl, dioxolyl, dioxinyl, oxathiolyl, benzodioxolyl, dithiolyl, dithiolanyl, tetrahydrothiophenyl, sulfolanyl, dioxanyl, dioxolanyl, tetrahydrofurodihydrofuranyl, dihydropyranyl, tetrahydropyranodihydrofuranyl, tetradyrofurofuranyl, tetrahydropyranofuranyl, diazolonyl, phthalimidinyl, benzoxanyl, benzopyrrolidinyl, benzopiperidinyl, benzoxolanyl, benzothiolanyl and benzothianyl.

The term "heteroaryl", alone or in combination with any other term, refers to an aromatic monocyclic or polycyclic ring radical containing five to twenty carbon atoms, preferably five to ten carbon atoms, in which one or more ring carbons, preferably one to four, are each replaced by a heteroatom such as N, O, and S. Preferred heteroaryl groups include 5-6 membered monocyclic heteroaryls and 8-10 membered bicyclic heteroaryls.

Also included within the scope of the term "heteroaryl" is a group in which a heteroaromatic ring is fused to one or more aromatic or non-aromatic rings where the radical or point of attachment is on the heteroaromatic ring. Examples include, but are not limited to, pyrido[3,4-d]pyrimidinyl, 7,8-dihydropyrido[3,4-d]pyrimidine and 5,6,7,8-tetrahydro-pyrido[3,4-d]pyrimidine. Unless otherwise indicated, the term "heteroaryl" also includes each possible positional isomer of a heteroaryl radical, such as in 2-pyrido[3,4-d]pyrimidinyl and 4-pyrido[3,4-d]pyrimidinyl.

Examples of heteroaryl groups include, but are not limited to, imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, carbazolyl, carbolinyl, tetrazolyl, benzofuranyl, oxazolyl, benzoxazolyl, isoxozolyl, isothiazolyl, thiadiazolyl, furazanyl, oxadiazolyl, benzimidazolyl, benzothienyl, quinolinyl, benzotriazolyl, benzothiazolyl, isoquinolinyl, isoindolyl, acridinyl and benzoisoxazolyl.

The term "heteroaralkyl" further refers to groups of —$R_aR_b$, where $R_a$ is an alkylene as defined herein and $R_b$ is a heteroaryl as defined herein.

The term "heteroatom" means nitrogen, oxygen, phosphorus, or sulfur and includes any oxidized forms thereof, including as non-limiting examples oxidized forms of nitrogen such as N(O) {$N^+$—$O^-$}, oxidized forms of sulfur such as S(O) and S(O)$_2$, and the quaternized form of any basic nitrogen.

The term "halogen" refers to fluorine, chlorine, bromine or iodine.

The term "pharmaceutically effective amount" refers to an amount of a compound of the invention that is effective in treating a CCR5-related disease, for example a virus infection, for example an HIV infection, in a patient either as monotherapy or in combination with other agents. The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylaxis" refers to preventing a disease or condition or preventing the occurrence of symptoms of such a disease or condition, in a patient. As used herein, the term "patient" refers to a mammal, including a human.

The term "pharmaceutically acceptable carrier" refers to a carrier that may be administered to a patient, together with a compound of this invention, and which does not destroy the pharmacological activity thereof and is nontoxic when administered in doses sufficient to deliver a therapeutic amount of the therapeutic agent.

The term "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group).

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

The compounds according to the invention contain one or more asymmetric carbon atoms and thus occur as racemates and racemic mixtures, single enantiomers, diastereomeric mixtures and individual diastereoisomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are also within the scope of this invention.

Certain compounds of this invention may exist in alternative tautomeric forms. All such tautomeric forms of the present compounds are within the scope of the invention. Unless otherwise indicated, the representation of either tautomer is meant to include the other.

The present invention features compounds according to the invention for use in medical therapy, for example for the treatment including prophylaxis of viral infections such as an HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

The present invention features use of the compounds of the present invention in the manufacture of a medicament for the treatment including prophylaxis of a CCR5-related disease or condition, for example, a viral infection, for example, an HIV infection.

According to another aspect, the present invention provides a method for the treatment including prevention of the symptoms or effects of a viral infection in an infected animal, for example, a mammal including a human, which comprises treating said animal with a pharmaceutically effective amount of a compound according to the invention. According to one aspect of the invention, the viral infection is a retroviral infection, in particular an HIV infection. A further aspect of the invention includes a method for the treatment including prevention of the symptoms or effects of an HBV infection.

The compounds according to the invention may also be used in adjuvant therapy in the treatment of HIV infections or HIV-associated symptoms or effects, for example Kaposi's sarcoma.

The compounds of the present invention may also be used in the treatment including prevention of other CCR5-related diseases and conditions, including multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis, immune mediated disorders.

The present invention further provides a method for the treatment of a clinical condition in an animal, for example, a mammal including a human which clinical condition includes those which have been discussed hereinbefore, which comprises treating said animal with a pharmaceutically effective amount of a compound according to the invention. The present invention also includes a method for the treatment including prophylaxis of any of the aforementioned diseases or conditions.

In yet a further aspect, the present invention provides the use of a compound according to the invention in the manufacture of a medicament for the treatment including prophylaxis of any of the above mentioned viral infections or conditions.

The above compounds according to the invention and their pharmaceutically acceptable derivatives may be employed in combination with other therapeutic agents for the treatment (including prevention) of the above infections or conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of such therapeutic agents include agents that are effective for the treatment of viral infections or associated conditions. Among these agents are (1-alpha, 2-beta, 3-alpha)-9-[2,3-bis(hydroxymethyl)cyclobutyl]guanine [(−)BHCG, SQ-34514, lobucavir], 9-[(2R,3R,4S)-3,4-bis (hydroxymethyl)-2-oxetanosyl]adenine (oxetanocin-G), acyclic nucleosides, for example acyclovir, valaciclovir, famciclovir, ganciclovir, and penciclovir, acyclic nucleoside phosphonates, for example (S)-1-(3-hydroxy-2-phosphonylmethoxypropyl)cytosine (HPMPC), [[[2-(6-amino-9H-purin-9-yl)ethoxy]methyl]phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), and (R)-[[2-(6-Amino-9H-purin-9-yl)-1-methylethoxy]methyl]phosphonic acid bis-(isopropoxycarbonyloxymethyl)ester (bis-POC-PMPA), ribonucleotide reductase inhibitors, for example 2-acetylpyridine 5-[(2-chloroanilino)thiocarbonyl) thiocarbonohydrazone and hydroxyurea, nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9H-purin-9-yl]-2-cyclopentene-1-methanol (abacavir), 9-[4-hydroxy-2-(hydroxymethyl)but-1-yl]-guanine (H2G), ABT-606 (2HM-H2G) and ribavirin, protease inhibitors, for example indinavir, ritonavir, nelfinavir, amprenavir, saquinavir, fosamprenavir, (R)—N-tert-butyl-3-[(2S,3S)-2-hydroxy-3-N—[(R)-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272), 4R-(4alpha,5alpha,6beta)]-1,3-bis[(3-aminophenyl) methyl]hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-I-tert-leucylamino]-4-phenylbutyl-$N^{alpha}$-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-hydroxy-1(S)-indanyl)-2(R)-phenylmethyl-4(S)-hydroxy-5-(1-(1-(4-benzo[b]furanylmethyl)-2(S)-N'-(tert-butylcarboxamido)piperazinyl)pentanamide (MK-944A), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, non-nucleoside reverse transcriptase inhibitors (NNRTIs), for example nevirapine (BI-RG-587), alpha-((2-acetyl-5-methylphenyl)amino)-2,6-dichloro-benzeneacetamide (loviride), 1-[3-(isopropylamino)-2-pyridyl]-4-[5-(methanesulfonamido)-1H-indol-2-ylcarbonyl]piperazine monomethanesulfonate (delavirdine), (10R, 11S, 12S)-12-Hydroxy-6,6,10,11-tetramethyl-4-propyl-11,12-dihydro-2H, 6H, 10H-benzo(1,2-b:3, 4-b':5,6-b")tripyran-2-one ((+) calanolide A), (4S)-6-Chloro-4-[1E)-cyclopropylethenyl)-3,4-dihydro-4-(trifluoromethyl)-2(1H)-quinazolinone (DPC-083), (S)-6-chloro-4-(cyclopropylethynyl)-1,4-dihydro-4-(trifluoromethyl)-2H-3,1-benzoxazin-2-one (efavirenz, DMP 266), 1-(ethoxymethyl)-5-(1-methylethyl)-6-(phenylmethyl)-2,4(1H,3H)-pyrimidinedione (MKC-442), and 5-(3, 5-dichlorophenyl)thio-4-isopropyl-1-(4-pyridyl)methyl-1H-imidazol-2-ylmethyl carbamate (capravirine), glycoprotein 120 antagonists, for example PRO-2000, PRO-542 and 1,4-bis[3-[(2,4-dichlorophenyl)carbonylamino]-2-oxo-5,8-disodiumsulfanyl]naphthalyl-2,5-dimethoxyphenyl-1,4-dihydrazone (FP-21399), cytokine antagonists, for example reticulose (Product-R), 1,1'-azobis-formamide (ADA), 1,11-(1,4-phenylenebis(methylene))bis-1,4,8,11-tetraazacyclotetradecane octahydrochloride (AMD-3100), integrase inhibitors, or fusion inhibitors, for example T-20 and T-1249.

The present invention further includes the use of a compound according to the invention in the manufacture of a medicament for simultaneous or sequential administration with at least another therapeutic agent, such as those defined hereinbefore.

Compounds of the present invention may be administered with an agent known to inhibit or reduce the metabolism of compounds, for example ritonavir. Accordingly, the present invention features a method for the treatment including prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 50 to 400 mg of active ingredient per unit dosage form.

While it is possible for the active ingredient to be administered alone it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Phamaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in Pharmaceutical Research 3 (6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray Pharmaceutical compositions containing in addition to the active ingredient such carriers as are known in the art to be appropriate.

Pharmaceutical compositions for rectal administration may be presented as a suppository with a suitable carrier comprising, for example, cocoa buffer or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

EXAMPLES

The following examples are intended for illustration only and are not intended to limit the scope of the invention in any way.

Low resolution, open-access LC-MS data were acquired in either ESI pos/neg or APCI pos/neg mode with scanning from 100-1100 amu @ 0.5 sec/scan. LC conditions: flowrate 0.8 mL/min. 85% H$_2$O (0.1% formic acid) to 100% MeOH (0.075% formic acid) in 6 minutes. Phenomenex Max-RP column, 2.0×50 mm.

High Resolution Mass Spectra were acquired using Micromass LCT mass spectrometer (time-of-flight) with flow injection (FIA-MS) at 0.3 mL/min with 100% MeOH (0.1% formic acid), run time of 2 minutes, in ESI+mode, scanning from 100-1100 amu @ 0.5 sec/scan. Reserpine was used as the lock mass (m/z 609.2812) and to adjust mass scale.

As will be appreciated by those skilled in the art, the following schemes may be followed in preparing the compounds of the present invention. The variability depicted within the scheme(s) illustrated herein, for example the variability of the "R" groups, should be limited to the particular scheme and not necessarily extended throughout the rest of the present specification.

Scheme 1:

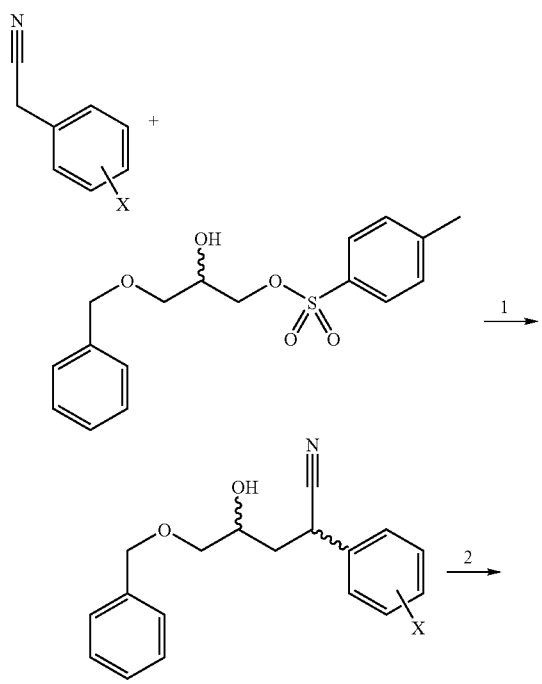

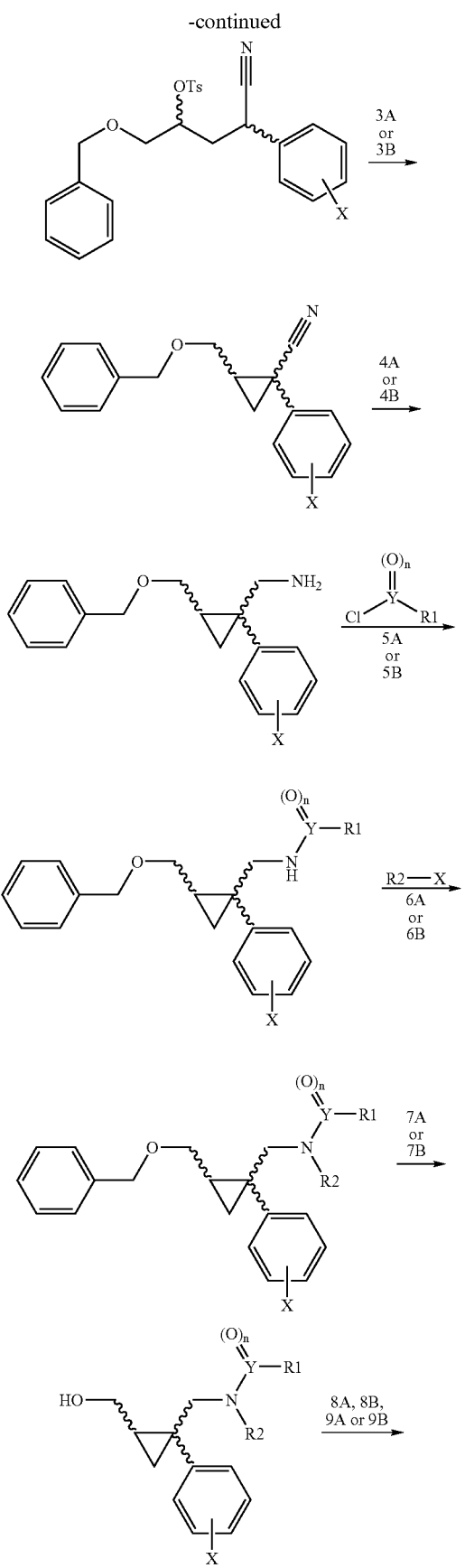

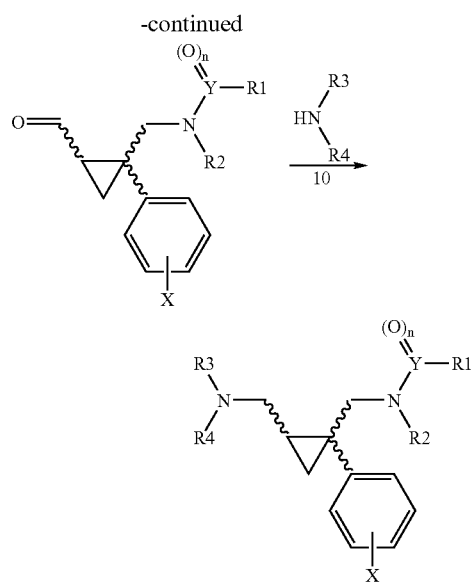

Where:

= an acid chloride or a sulfonyl chloride

R2—X = an alkyl halide

Preparation 1: (4R)-4-hydroxy-2-phenyl-5-[(phenyl-methyl)oxy]pentanenitrile

Phenylacetonitrile (4.59 g, 39.2 mmol) and (2S)-2-hydroxy-3-[(phenylmethyl)oxy]propyl 4-methylbenzenesulfonate (13.20 g, 39.2 mmol, 1 eq) were dissolved in 50 mL THF, cooled to −78° C., and treated with 2.5M butyllithium in hexanes (35 mL, 86.3 mmol, 2.2 eq) added dropwise over 30 min. The reaction mixture was stirred 4 h at −78° C., allowed to warm to ambient temperature and stirred an additional 16 h. The reaction mixture was diluted with EtOAc, washed successively with water and brine, dried over MgSO$_4$, filtered and concentrated to give the diastereomeric product as an orange oil in quantitative yield which was carried on without purification. ES-LCMS m/z 304.33 (M+Na).

Preparation 2: (1R)-3-cyano-3-phenyl-1-{[(phenylmethyl)oxy]methyl}propyl 4-methylbenzenesulfonate

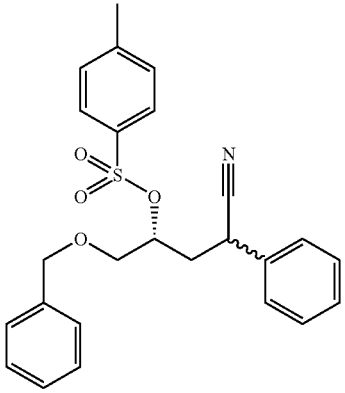

(4R)-4-hydroxy-2-phenyl-5-[(phenylmethyl)oxy]pentanenitrile (16.0 g, 57 mmol), accessed via the method of preparation 1, was dissolved in 116 mL CHCl₃ and 116 mL Pyridine (25 eq) with DMAP (0.70 g, 5.7 mmol, 0.1 eq) and cooled to 0° C. 4-methylbenzenesulfonyl chloride (43.5 g, 228 mmol, 4 eq) was added to the reaction mixture and stirred 3 days at 0° C. The reaction mixture was washed successively with 1N HCl (4×250 mL) and brine, dried over MgSO₄, filtered and concentrated to a red oil. The crude material was purified by flash chromatography (SiO₂, 10→25% EtOAc/Hexanes) to give the diastereomeric product as a yellow oil (14.88 g, 34.2 mmol, 60%). ES-LCMS m/z 458.36 (M+Na).

Preparation 3A: (1S,2R)-1-phenyl-2-{[(phenylmethyl)oxy]methyl}cyclopropanecarbonitrile

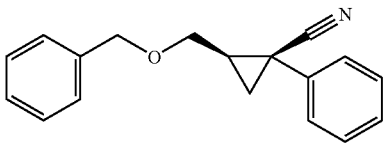

To (1R)-3-cyano-3-phenyl-1-{[(phenylmethyl)oxy]methyl}propyl 4-methylbenzenesulfonate (7.4 g, 17.0 mmol), accessed via the method of preparation 2, in 70 mL DMF at −42° C. was added 1M lithium bis(trimethylsilyl)amide in hexanes (25.5 mL, 25.5 mmol, 1.5 eq) dropwise and stirred with continued cooling at −42° C. for 1 h. The reaction mixture was diluted with EtOAc, washed successively with water (4×) and brine, dried over MgSO₄, filtered and concentrated to give the title compound (4.25 g, 16.1 mmol, 95%) as a yellow oil which was shown to be a 94:6 mix of the title compound to the product of Preparation 3B. $^1$H NMR (300 MHz, CDCl₃) δ 7.42-7.29 (m, 10H), 4.64 (m, 2H), 3.91-3.86 (m, 1H), 3.74-3.68 (m,1H), 2.00-1.90 (m, 1H), 1.68-1.56 (m, 2H).

Preparation 3B: (1R,2R)-1-phenyl-2-{[(phenylmethyl)oxy]methyl}cyclopropanecarbonitrile

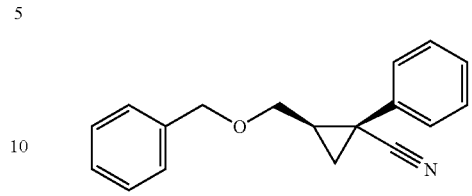

To 765 mL toluene cooled to 0° C. was added 1.0 M LHMDS in hexanes (148.1 mL, 148.1 mmol, 1 eq). To this solution was added (1R)-3-cyano-3-phenyl-1-{[(phenylmethyl)oxy]methyl}propyl 4-methylbenzenesulfonate (43.0 g, 98.73 mmol, 1 eq), accessed via the method of Preparation 2, in 236 mL toluene. The reaction mixture was stirred at 0° C. for 16 h, then washed successively with water and brine, dried over MgSO₄, filtered and concentrated to give a yellow oil that was shown to be an 8:2 diastereomeric mixture of the title compound to the product of Preparation 3A. The desired diastereomer (16.0 g, 62%) was separated by silica gel flash chromatography using 9:1→8:2 hexanes in ethyl acetate. $^1$H NMR (300 MHz, CDCl₃) δ 7.44-7.15 (m, 10H), 4.28-4.19 (m, 2H), 3.31-3.27 (m, 1H), 2.94-2.84 (m, 1H), 2.22-2.15 (m,1H), 1.76-1.72 (m, 1H), 1.47-1.44 (m, 1H). ES-LCMS m/z 264.1 (M+H).

Preparation 4A: [((1S,2R)-1-phenyl-2-{[(phenylmethyl)oxy]methyl}cyclopropyl)methyl]amine

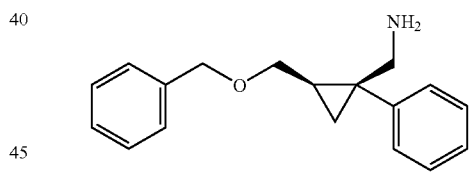

To 16.2 mL 1M lithium aluminum hydride (16.2 mmol) in diethyl ether at 0° C. (1S,2R)-1-phenyl-2-{[(phenylmethyl)oxy]methyl}cyclopropanecarbonitrile (4.25 g, 16.2 mmol), accessed via the method of Preparation 3A, dissolved in 17 mL diethyl ether. After complete addition, the reaction mixture was stirred at 0° C. for 2 h followed by 4 h at ambient temperature. The reaction mixture was diluted with 360 mL diethyl ether and quenched with successive addition of 0.6 mL water, 0.6 mL 15% NaOH, and 3.0 mL water. The reaction mixture was filtered and the filtrate was concentrated to a clear oil. The oil was purified by flash chromatography (SiO₂, 3→5% CH₃OH/EtOAc with 1% NH₄OH) to give the title product (3.08 g, 11.5 mmol, 71%) as a single diastereomer. $^1$H NMR (300 MHz, CDCl₃) δ 7.37-7.19 (m, 10H), 4.62-4.54 (m, 2H), 3.88 (m, 1H), 3.34 (m, 1H), 2.96 (d, J=14.1 Hz, 1H), 2.70 (d, J=14.1 Hz, ₁H), 1.58 (m, 1H), 1.00 (m, 1H), 0.62 (m, 1H). ES-LCMS m/z 268.4 (M+H).

Preparation 4B: [((1R,2R)-1-phenyl-2-{[(phenylmethyl)oxy]methyl]cyclopropyl)methyl]amine

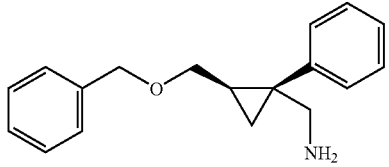

To 19.4 mL 1M lithium aluminum hydride (19.4 mmol) in diethyl ether at 0° C. was added (1R,2R)-1-phenyl-2-{[(phenylmethyl)oxy]methyl}cyclopropanecarbonitrile (5.10 g, 19.4 mmol), accessed via the method of Preparation 3B, dissolved in 20 mL diethyl ether. After complete addition, the reaction mixture was stirred at 0° C. for 3 h. The reaction mixture was diluted with 360 mL diethyl ether and quenched with successive addition of 0.6 mL water, 0.6 mL 15% NaOH, and 3.0 mL water. The reaction mixture was filtered and the filtrate was concentrated to a clear oil. The oil was purified by flash chromatography (SiO$_2$, 3→7% CH$_3$OH/EtOAc with 1% NH$_4$OH) to give the title product (3.03 g, 11.3 mmol, 59%) as a single diastereomer. $^1$H NMR (300 MHz, CDCl$_3$) δ 7.35-7.21 (m, 10H), 4.35-4.25 (m, 2H), 3.22-3.18 (m, 1H), 3.00-2.94 (m, 2H), 2.43 (d, J=13.5 Hz, 1H), 1.36 (m, 1H), 0.91 (m, 1H), 0.78 (m, 1H). ES-LCMS m/z 268.4 (M+H).

Preparation 5A: N-[(1S,2R)-1-phenyl-2-{[(phenylmethyl)oxy]methyl}cyclopropyl)methyl]benzenesulfonamide

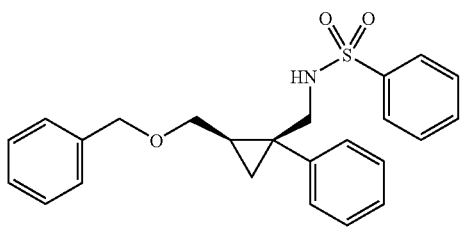

[((1S,2R)-1-phenyl-2-{[(phenylmethyl)oxy]methyl}cyclopropyl)methyl]amine (1.00 g, 3.74 mmol), accessed via the method of Preparation 4A, was dissolved in 10 mL DCE and combined with polymer-bound diisopropylamine (4.49 mmol, 1.2 eq). Benzenesulfonyl chloride (1.06 g, 5.98 mmol, 1.6 eq) was added and the reaction mixture agitated 16 h at ambient temperature. Excess sulfonyl chloride was scavenged by addition of polymer-bound trisamine (4.49 mmol, 1.2 eq) with agitation at ambient temperature for 16 h. The solid-supported reagents were filtered off, washed successively with DCM, CH$_3$OH, THF, and DCM, the filtrates combined and concentrated to give the title product (1.52 g, 100%) as an amber oil. $^1$H NMR (300 MHz, CDCl$_3$) δ 8.04-8.02 (m, 1H), 7.75-7.15 (m, 14H), 5.67 (m, 1H), 4.55 (s, 2H), 3.90-3.86 (m, 1H), 3.57-3.51 (m, 1H), 3.12-3.07 (m, 1H), 2.90-2.85 (m, 1H), 1.62-1.56 (m, 1H), 1.03-0.99 (m, 1H), 0.66 (m, 1H). ES-LCMS m/z 430.1 (M+Na).

Preparation 5B: N-[((1R,2R)-1-phenyl-2-{([(phenylmethyl)oxy]methyl}cyclopropyl)methyl]benzenesulfonamide

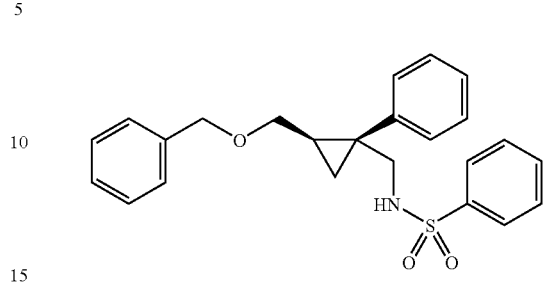

[((1R,2R)-1-phenyl-2-{[(phenylmethyl)oxy]methyl}cyclopropyl)methyl]amine (1.00 g, 3.74 mmol), accessed via the method of preparation 4B, was dissolved in 10 mL DCE and combined with polymer-bound diisopropylamine (4.49 mmol, 1.2 eq). Benzenesulfonyl chloride (1.06 g, 5.98 mmol, 1.6 eq) was added and the reaction mixture agitated 16 h at ambient temperature. Excess sulfonyl chloride was scavenged by addition of polymer-bound trisamine (4.49 mmol, 1.2 eq) with agitation at ambient temperature for 16 h. The solid-supported reagents were filtered off, washed successively with DCM, CH$_3$OH, THF, and DCM, the filtrates combined and concentrated to give the title product (1.52 g, 100%) as an amber oil. $^1$H NMR (300 MHz, CDCl$_3$) δ 8.04-8.02 (m, 1H), 7.64-7.19 (m, 14H), 5.25 (m, 1H), 4.23 (ABq, J=35.5, 11.4 Hz, 2H), 3.28-3.24 (m, 1H), 3.15 (d, J=12.7 Hz, 1H), 2.90 (d, J=12.7 Hz, 1H), 2.82-2.77 (m, 1H), 1.36-1.31 (m, 1H), 0.96-0.92 (m, 1H), 0.76 (m, 1H). ES-LCMS m/z 430.2 (M+Na).

Preparation 6A: N-methyl-N-[((1S,2R)-1-phenyl-2-{[(phenylmethyl)oxy]methyl}cyclopropyl)methyl]benzenesulfonamide

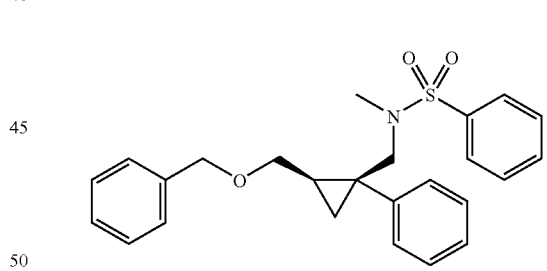

Iodomethane (2.12 g, 14.9 mmol, 4 eq) was added portionwise to N-[((1S,2R)-1-phenyl-2-{[(phenylmethyl)oxy]methyl}cyclopropyl)methyl]benzenesulfonamide (1.71 g, 3.74 mmol, 1 eq), accessed via the method of preparation 5A, in 7 mL DMF with potassium carbonate (1.03 g, 7.48 mmol, 2 eq) over 6 h at 80° C. Following addition, the reaction mixture was stirred 16 h at 80° C. The reaction mixture was diluted with EtOAc, washed successively with saturated aqueous NaHCO$_3$, water (4×) and brine, dried over MgSO$_4$, filtered and concentrated to give a brown oil. The crude material was purified by flash chromatography (SiO$_2$, eluted successively with hexanes and EtOAc/hexanes (1:4)) to give the title product (1.57 g, 100%) as a yellow oil. $^1$H NMR (300 MHz, CDCl$_3$) δ 7.58-7.19 (m, 15H), 4.57 (ABq, J=24.3, 11.9 Hz, 2H), 3.84-3.80 (m, 1H), 3.58-3.48 (m, 1H), 3.29 (d, J=14.1 Hz, 1H), 2.50 (s, 3H), 1.47 (m, 1H), 1.33 (m, 1H), 0.91 (m, 1H). ES-LCMS m/z 444.2 (M+Na).

Preparation 6B: N-methyl-N-[((1R,2R)-1-phenyl-2-{[(phenylmethyl)oxy]methyl}cyclopropyl)methyl]benzenesulfonamide

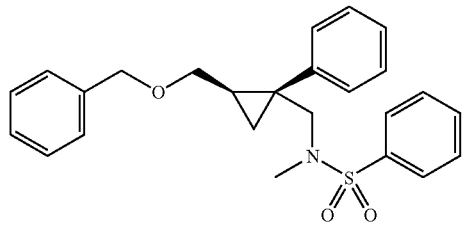

Iodomethane (2.12 g, 14.9 mmol, 4 eq) was added portionwise to N-[((1R,2R)-1-phenyl-2-{[(phenylmethyl)oxy]methyl}cyclopropyl)methyl]benzenesulfonamide (1.71 g, 3.74 mmol, 1 eq), accessed via the method of preparation 5B, in 7 mL DMF with potassium carbonate (1.03 g, 7.48 mmol, 2 eq) over 6 h at 80° C. Following addition, the reaction mixture was stirred 16 h at 80° C. The reaction mixture was diluted with EtOAc, washed successively with saturated aqueous NaHCO$_3$, water (4×) and brine, dried over MgSO$_4$, filtered and concentrated to give a brown oil. The crude material was purified by flash chromatography (SiO$_2$, eluted successively with hexanes and EtOAc/hexanes (1:4)) to give the title product (1.57 g, 100%) as a yellow oil. $^1$H NMR (300 MHz, CDCl$_3$) δ 7.58-7.21 (m, 15H), 4.26 (ABq, J=26.5, 11.7 Hz, 2H), 3.50 (d, J=14.0 Hz, 1H), 3.23-3.20 (m, 1H), 2.94-2.89 (m, 2H), 2.54 (s, 3H), 1.39 (m, 1H), 1.10 (m, 1H), 0.92 (m, 1H). ES-LCMS m/z 444.3 (M+Na).

Preparation 7A: N-{[(1S,2R)-2-(hydroxymethyl)-1-phenylcyclopropyl]methyl}-N-methylbenzenesulfonamide

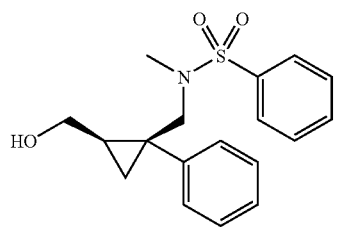

N-methyl-N-[((1S,2R)-1-phenyl-2-{[(phenylmethyl)oxy]methyl}cyclopropyl)methyl]benzenesulfonamide (1.57 g, 3.74 mmol), accessed via the method of preparation 6A, was combined with 10% palladium on activated carbon (0.35 g) in EtOAc and hydrogenated under 1 atm H$_2$(g) for 4 h at ambient temperature. The catalyst was filtered off through celite and the filtrate concentrated to give the title product (1.17 g, 3.53 mmol, 95%) as a clear oil. $^1$H NMR (300 MHz, CDCl$_3$) δ 7.68-7.18 (m, 10H), 4.07-4.03 (m, 1H), 3.72-3.66 (m, 1H), 3.55 (d, J=14.1 Hz, 1H), 3.25 (d, J=14.1 Hz, 1H), 2.36 (s, 3H), 1.59 (m, 1H), 1.18-1.15 (m, 1H), 0.79 (m, 1H). ES-LCMS m/z 354.3 (M+Na).

Preparation 7B: N-[(1R,2R)-2-(hydroxymethyl)-1-phenylcyclopropyl]methyl}-N-methylbenzenesulfonamide

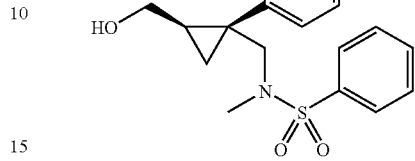

N-methyl-N-[((1R,2R)-1-phenyl-2-{[(phenylmethyl)oxy]methyl}cyclopropyl)methyl]benzenesulfonamide (1.57 g, 3.74 mmol), accessed via the method of preparation 6B, was combined with 10% palladium on activated carbon (0.35 g) in EtOAc and hydrogenated under 1 atm H$_2$(g) for 4 h at ambient temperature. The catalyst was filtered off through celite and the filtrate concentrated to give the title product (1.01 g, 3.05 mmol, 82%) as a clear oil. $^1$H NMR (300 MHz, CDCl$_3$) δ 7.63-7.61 (m, 2H), 7.53 (m, 1H), 7.46-7.43 (m, 2H), 7.33-7.24 (m, 5H), 3.60 (d, J=13.8 Hz, 1H), 3.40-3.35 (m, 1H), 3.20-3.14 (m, 1H), 2.92 (d, J=13.8 Hz, 1H), 2.55 (s, 3H), 1.43 (m, 1H), 1.10 (m, 1H), 0.99 (m, 1H). ES-LCMS m/z 354.2 (M+Na).

Preparation 8A: N-{[(1S,2R)-2-formyl-1-phenylcyclopropyl]methyl}-N-methylbenzenesulfonamide

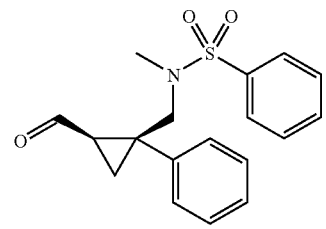

N-{[(1S,2R)-2-(hydroxymethyl)-1-phenylcyclopropyl]methyl}-N-methylbenzenesulfonamide (600 mg, 1.82 mmol), accessed via the method of preparation 7A, was dissolved in 18 mL DCM with 270 uL 2-methylpropan-2-ol and treated with Dess-Martin Periodinane (1.23 g, 2.90 mmol, 1.6 eq) at ambient temperature for 16 h. The reaction mixture was diluted with 42 mL diethyl ether and treated with 22 mL 1N NaOH at ambient temperature for 15 min. The organic phase was separated, the aqueous phase extracted twice with diethyl ether, the organic phases combined, washed with brine, dried over MgSO$_4$, filtered and concentrated to a colorless oil. The crude material was purified by flash chromatography (SiO$_2$, eluted successively with DCM, EtOAc/hexanes (1:4)) to the title product (270 mg, 0.82 mmol, 45%) as a colorless oil. $^1$H NMR (300 MHz, CDCl$_3$) δ 9.82 (d, J=3.8 Hz, 1H), 7.65-7.28 (m, 10H), 3.53-3.43 (m, 2H), 2.42 (s, 3H), 2.34-2.32 (m, 1H), 1.90-1.87 (m, 1H), 1.70-1.66 (m, 1H).

Preparation 8B: N-{[(1R,2R)-2-formyl-1-phenylcyclopropyl]methyl}N-methylbenzenesulfonamide

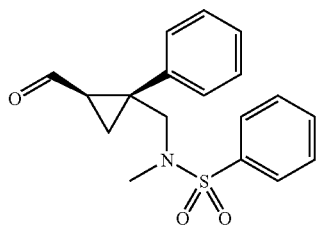

N-{[(1R,2R)-2-(hydroxymethyl)-1-phenylcyclopropyl]methyl}-N-methylbenzenesulfonamide (600 mg, 1.82 mmol), accessed via the method of preparation 7B, was dissolved in 18 mL DCM with 270 uL 2-methylpropan-2-ol and treated with Dess-Martin Periodinane (1.23 g, 2.90 mmol, 1.6 eq) at ambient temperature for 16 h. The reaction mixture was diluted with 42 mL diethyl ether and treated with 22 mL 1N NaOH at ambient temperature for 15 min. The organic phase was separated, the aqueous phase extracted twice with diethyl ether, the organic phases combined, washed with brine, dried over $MgSO_4$, filtered and concentrated to a colorless oil. The crude material was purified by flash chromatography ($SiO_2$, eluted successively with DCM, EtOAc/hexanes (1:4)) to the title product (410 mg, 1.24 mmol, 69%) as a colorless oil. $^1$H NMR (300 MHz, $CDCl_3$) δ 8.54 (d, J=6.7 Hz, 1H), 7.65 (m, 2H), 7.55 (m, 1H), 7.47 (m, 2H), 7.31-7.23 (m, 5H), 3.50 (d, J=14.3 Hz, 1H), 3.09 (d, J=14.3 Hz, 1H), 2.52 (s, 3H), 2.15-2.08 (m, 1H), 1.93 (m, 1H), 1.76-1.73 (m, 1H).

Preparation 9A: N-{[(1R,2S)-2-formyl-1-phenylcyclopropyl]methyl}-N-methylbenzenesulfonamide

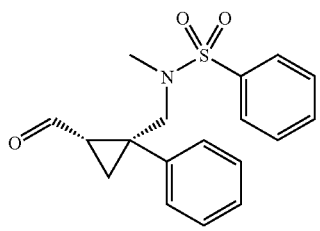

Starting from phenylacetonitrile and (2R)-2-hydroxy-3-[(phenylmethyl)oxy]propyl 4-methylbenzenesulfonate and using the methods of Preparations 1, 2, 3A, 4A, 5A, 6A, 7A, and 8A sequentially, the title product can be obtained in comparable yields and analytical characterization to those obtained in those preparations.

Preparation 9B: N-{[(1S,2S)-2-formyl-1-phenylcyclopropyl]methyl}-N-methylbenzenesulfonamide

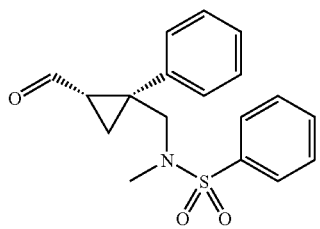

Starting from phenylacetonitrile and (2R)-2-hydroxy-3-[(phenylmethyl)oxy]propyl 4-methylbenzenesulfonate and using the methods of Preparations 1, 2, 3B, 4B, 5B, 6B, 7B, and 8B sequentially, the title product can be obtained in comparable yields and analytical characterization to those obtained in those preparations.

Preparation 10: Compounds of general formula:

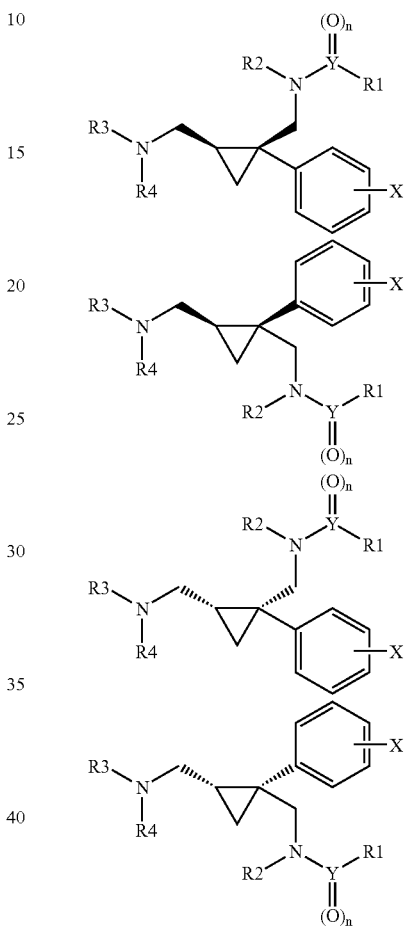

To aldehydes (33 mg, 100 μmol), made according to the methods of preparations 8A, 8B, 9A, and 9B, dissolved in 2 mL DCE were added secondary amines (100 μmol, 1 eq) in 1 mL DCM and treated with sodium triacetoxyborohydride (42 mg, 200 μmol, 2 eq) at ambient temperature for 16 h with continuous agitation. The reaction mixtures were each treated with 4 mL saturated aqueous $NaHCO_3$ with agitation for 1 h, the organic phases separated via filtration through hydrophobic frit tube assemblies, and the organic filtrates concentrated to dryness. Crude products were dissolved in 300 microliters of DMSO and brought up to a final volume of 500 microliters using methanol. This 500 microliter solution was injected by a Waters 2767 autosampler into an XTerra C18 5 micron particle HPLC column (19 mm×150 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. Final products were obtained in moderate to good yields. Chiral HPLC was performed on representative samples to confirm that homochiral integrity had been preserved.

The following demonstrate the above-referenced general scheme:

Example 1

N-[((1S,2R)-2-{[4-(3-benzyl-1,2,4-oxadiazol-5-yl)piperidin-1-yl]methyl}-1-phenylcyclopropyl)methyl]-N-methylbenzenesulfonamide

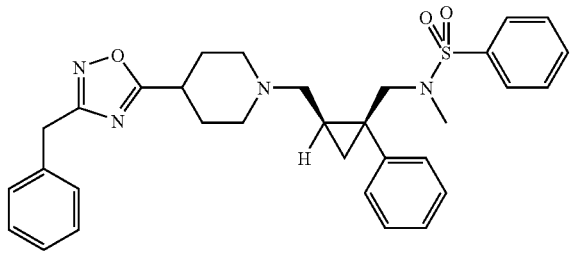

N-{[(1S,2R)-2-formyl-1-phenylcyclopropyl]methyl}-N-methylbenzenesulfonamide and 4-(3-benzyl-1,2,4-oxadiazol-5-yl)piperidine (incorporating by reference as needed WO 00/39125) were reacted as per Preparation 10 to give the title compound.

$^1$H NMR (300 MHz, DMSO-d$_6$) δ 7.69-7.55 (m, 5H), 7.36-7.18 (m, 10H), 4.08 (s, 2H), 3.91 (d, J=13.2 Hz, 1H), 3.08-2.98 (m, 2H), 2.81 (d, J=13.2 Hz, 1H), 2.84-2.78 (m, 1H), 2.59-2.43 (m, 2H), 2.52 (s, 3H), 2.27-1.97 (m, 4H), 1.80-1.66 (m, 2H), 1.45-1.39 (m, 1H), 1.09-0.99 (m, 1H), 0.80 (m, 1H). ES-LCMS m/z 557.2 (M+H).

Example 2

Benzyl ethyl{1-[((1R,2S)-2-{[methyl(phenylsulfonyl)amino]methyl}-2-phenylcyclopropyl)methyl]piperidin-4-yl}carbamate

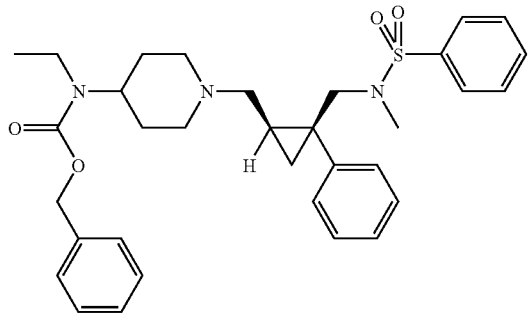

N-{[(1S,2R)-2-formyl-1-phenylcyclopropyl]methyl}-N-methylbenzenesulfonamide and benzyl ethyl(piperidin-4-yl)carbamate (incorporating by reference as needed *Bioorg. and Med. Chem. Lett.*, 11 (2001), 2475) were reacted as per Preparation 10 to give the title compound.

$^1$H NMR (300 MHz, DMSO-d$_8$) δ 7.70-7.56 (m, 5H), 7.40-7.17 (m, 10H), 5.09 (s, 2H), 3.88 (d, J=13.3 Hz, 1H), 3.75 (m, 1H), 3.19 (q, J=6.6 Hz, 2H), 3.09-3.05 (m, 1H), 2.91-2.87 (m, 1H), 2.83 (d, J=13.3 Hz, 1H), 2.58-2.52 (m, 1H), 2.52 (s, 3H), 2.44-2.38 (m, 1H), 2.08-1.92 (m, 2H), 1.77-1.58 (m, 4H), 1.41-1.37 (m, 0.1H), 1.07 (t, J=6.6 Hz, 3H), 1.07-0.99 (m, 1H), 0.78 (m, 1H). ES-LCMS m/z 576.1 (M+H).

Example 3

N-[((1S,2S)-2-{[4-(3-benzyl-1,2,4-oxadiazol-5-yl)piperidin-1-yl]methyl}-1-phenylcyclopropyl)methyl]-N-methylbenzenesulfonamide

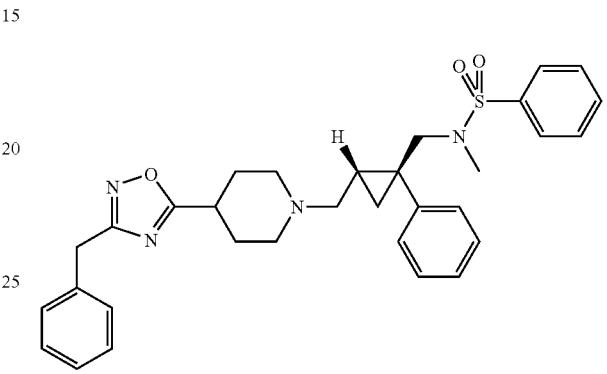

N-{[(1S,2S)-2-formyl-1-phenylcyclopropyl]methyl}-N-methylbenzenesulfonamide and 4-(3-benzyl-1,2,4-oxadiazol-5-yl)piperidine (incorporating by reference as needed WO 00/39125) were reacted as per Preparation 10 to give the title compound.

$^1$H NMR (300 MHz, DMSO-de) δ 7.69-7.54 (m, 5H), 7.35-7.20 (m, 10H), 4.06 (s, 2H), 3.55 (d, J=13.8 Hz, 1H), 2.97-2.85 (m, 1H), 2.78 (d, J=13.8 Hz, 1H), 2.64-2.59 (m, 1H), 2.53 (s, 3H), 2.27-2.21 (m, 1H), 2.02-1.88 (m, 4H), 1.75-1.61 (m, 2H), 1.48-1.41 (m, 1H), 1.17 (m, 1H), 1.07-1.02 (m, 1H), 0.93-0.89 (m, 1H). ES-LCMS m/z 557.1 (M+H).

Example 4 benzyl ethyl{1-[((1S,2S)-2-{[methyl(phenylsulfonyl)amino]methyl}-2-phenylcyclopropyl)methyl]piperidin-4-yl}carbamate

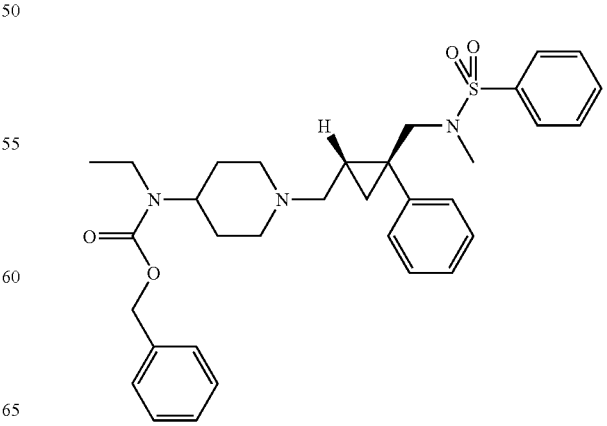

N-{[(1S,2S)-2-formyl-1-phenylcyclopropyl]methyl}-N-methylbenzenesulfonamide and benzyl ethyl(piperidin-4-yl)carbamate (incorporating by reference as needed *Bioorg. and Med. Chem. Lett.*, 11 (2001), 2475) were reacted as per Preparation 10 to give the title compound.

¹H NMR (300 MHz, DMSO-d₆) δ 7.67-7.55 (m, 5H), 7.39-7.21 (m, 10H), 5.07 (s, 2H), 3.67 (m, 1H), 3.57 (d, J=13.3 Hz, 1H), 3.17 (q, J=6.6 Hz, 2H), 2.99-2.93 (m, 1H), 2.76 (d, J=13.3 Hz, 1H), 2.75-2.68 (m, 1H), 2.52 (s, 3H), 2.29-2.19 (m, 1H), 1.87-1.38 (m, 7H), 1.11 (m, 1H), 1.04 (t, J=6.6 Hz, 3H), 1.07-1.03 (m, 1H), 0.90 (m, 1H). ES-LCMS m/z 576.2 (M+H).

Example 5

N-[((1S,2R)-1-(3-chlorophenyl)-2-{[(3-exo)-3-(2-methyl-1H-benzimidazol-1-yl)-8-azabicyclo[3.2.1]oct-8-yl]methyl}cyclopropyl)methyl]-N-methylbenzenesulfonamide

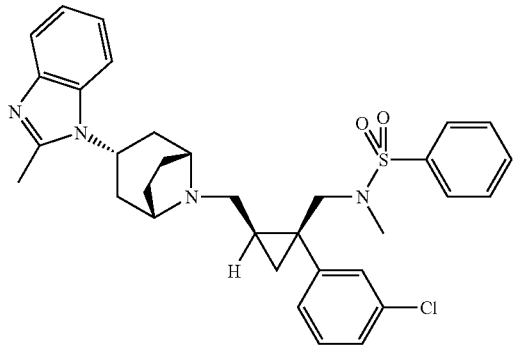

N-{[(1S,2R)-1-(3-chlorophenyl)-2-formylcyclopropyl]methyl}-N-methylbenzenesulfonamide [made from (3-chlorophenyl)acetonitrile via the sequential methods of Preparations 1, 2, 3A, 4A, 5A, 6A, 7A, 8A] and 1-[(3-exo)-8-azabicyclo[3.2.1]oct-3-yl]-2-methyl-1H-benzimidazole (incorporating by reference as needed WO 00/38680) were reacted as per Preparation 10 to give the title compound. ES-LCMS m/z 589.6 (M+H).

Example 6

N-{[(1S,2R)-2-{[4-(3-benzyl-1,2,4-oxadiazol-5-yl)piperidin-1-yl]methyl}-1-(3-chlorophenyl)cyclopropyl]methyl}-N-methylbenzenesulfonamide

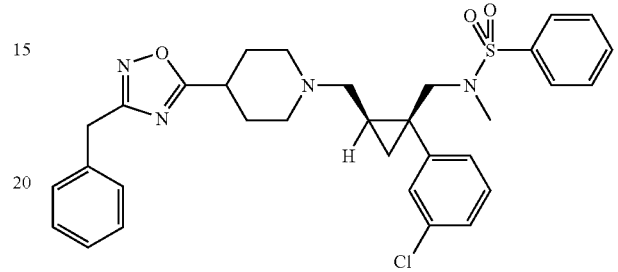

N-{[(1S,2R)-1-(3-chlorophenyl)-2-formylcyclopropyl]methyl}-N-methylbenzenesulfonamide [made from (3-chlorophenyl)acetonitrile via the sequential methods of Preparations 1, 2, 3A, 4A, 5A, 6A, 7A, 8A] and 4-(3-benzyl-1,2,4-oxadiazol-5-yl)piperidine (incorporating by reference as needed WO 00/39125) were reacted as per Preparation 10 to give the title compound.

¹H NMR (300 MHz, CD₃OD) δ 7.70-7.53 (m, 5H), 7.36-7.23 (m, 9H), 4.07 (s, 2H), 3.83 (d, J=14.0 Hz, 1H), 3.39-3.16 (m, 4H), 3.09 (d, J=14.0 Hz, 1H), 2.78-2.61 (m, 3H), 2.57 (s, 3H), 2.28-2.21 (m, 2H), 2.07-1.94 (m, 2H), 1.53-1.48 (m, 1H), 1.33-1.29 (m, 1H), 1.00-0.96 (m, 1H). ES-LCMS m/z 591.5 (M+H).

Scheme 2:

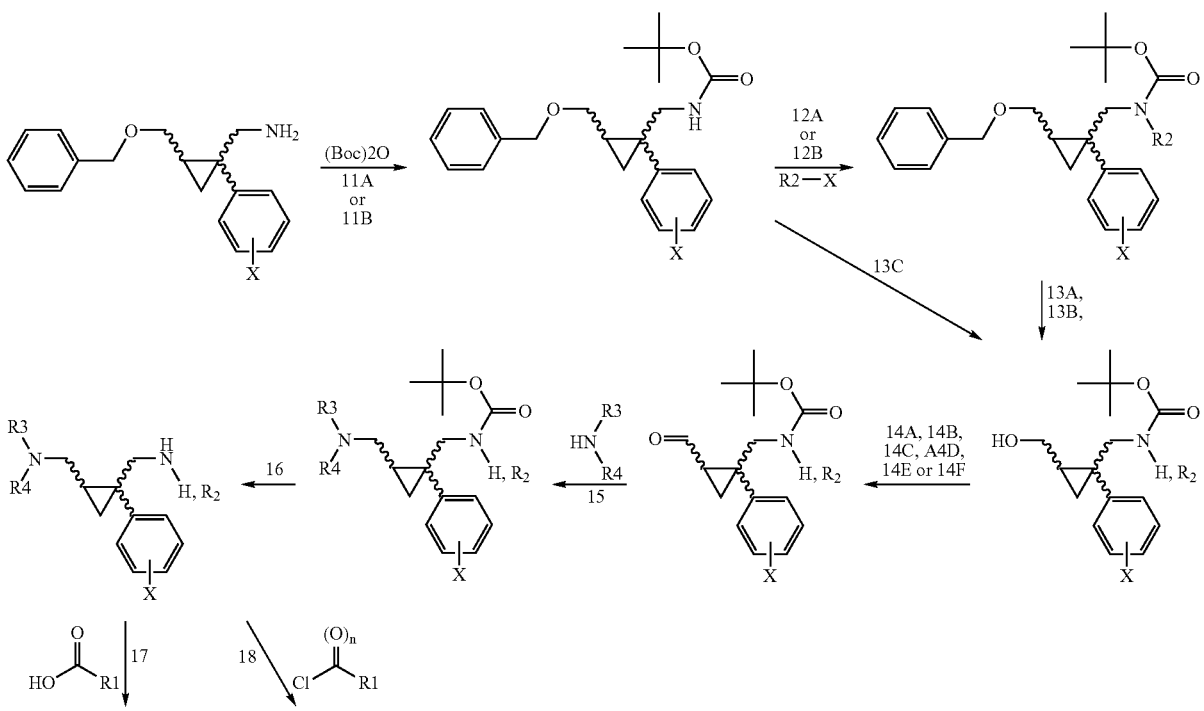

-continued

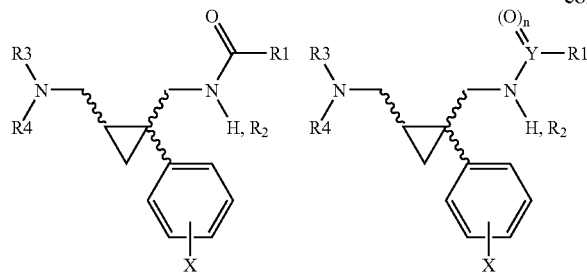

Where:

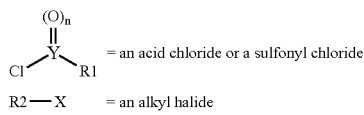  = an acid chloride or a sulfonyl chloride

R2—X  = an alkyl halide

Preparation 11A: 1,1-dimethylethyl [((1S,2R)-1-phenyl-2-{[(phenylmethyl)oxy]methyl}cyclopropyl)methyl]carbamate

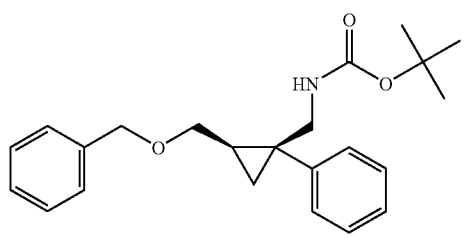

To a solution of [((1S,2R)-1-phenyl-2-{[(phenylmethyl)oxy]methyl}cyclopropyl)methyl]amine (28.53 g, 107 mmol, 1 eq), accessed via the method of preparation 4A, and triethylamine (11.9 g, 117 mmol, 1.1 eq) in 380 mL DCM cooled to 0° C. was added di(tert-butyl) dicarbonate (24.45 g, 112 mmol, 1.05 eq). The resultant mixture was stirred 2 h at 0° C. followed by 16 h at ambient temperature. The reaction mixture was diluted with DCM, washed successively with saturated NaHCO₃ and brine, dried over MgSO₄, filtered and concentrated to give the title compound (39.3 g, 107 mmol, 100%) as an amber oil. $^1$H NMR (300 MHz, CDCl₃) δ 7.43-7.17(m, 10H), 5.35 (d, J=7.8 Hz, 1H), 4.60 (m, 2H), 3.95 (m, 2H), 3.35 (t, J=10.3 Hz, 1H), 2.97 (dd, J=13.9, 2.1 Hz, 1H), 1.62 (m, 1H), 1.35 (s, 9H), 1.08 (m, 1H), 0.77 (t, J=5.4 Hz, 1H). ES-LCMS m/z 390.30 (M+Na).

Preparation 11B: 1,1-dimethylethyl [((1R,2R)-1-phenyl-2-{[(phenylmethyl)oxy]methyl}cyclopropyl)methyl]carbamate

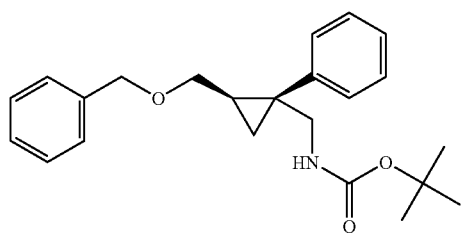

To a solution of [((1R,2R)-1-phenyl-2-{[(phenylmethyl)oxy]methyl}cyclopropyl)methyl]amine (12.6 g, 47.13 mmol, 1 eq), accessed via the method of 4B, and triethylamine (5.25 g, 51.8 mmol, 1.1 eq) in 200 mL DCM cooled to 0° C. was added di(tert-butyl) dicarbonate (10.79 g, 49.48 mmol, 1.05 eq). The resultant mixture was stirred 2 h at 0° C. followed by 16 h at ambient temperature. The reaction mixture was diluted with DCM, washed successively with saturated NaHCO₃ and brine, dried over MgSO₄, filtered and concentrated to give the title compound (16.6 g, 45.17 mmol, 96%) as a yellow oil. $^1$H NMR (400 MHz, CDCl₃) δ 7.42-7.14 (m, 10H), 4.50 (m, 1H), 4.35-4.25 (m, 2H), 3.50-3.45 (m, 1H), 3.21-3.17 (m, 1H), 3.10-3.05 (m, 1H), 3.00-2.95 (m, 1H), 1.36 (s, 9H), 1.07-1.04 (m, 1H), 0.82-0.798(m, 1H). ES-LCMS m/z 368.2 (M+H).

Preparation 12A: 1,1-dimethylethyl methyl[((1S,2R)-1-phenyl-2-{[(phenylmethyl)oxy]methyl}cyclopropyl)methyl]carbamate

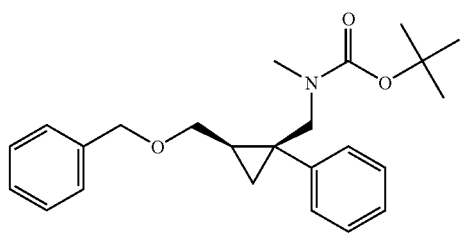

To a solution of 1,1-dimethylethyl [((1S,2R)-phenyl-2-{[(phenylmethyl)oxy]methyl}cyclopropyl)methyl]carbamate (39.2 g, 92 mmol), accessed via the method of 11A, and methyl iodide (39.2 g, 276 mmol, 3 eq) in 300 mL THF cooled to 0° C. was added 1M sodium bis(trimethylsilyl)amide in THF (138 mL, 138 mmol, 1.5 eq). The reaction mixture was stirred 2 h at 0° C. followed by 16 h at ambient temperature. The reaction mixture was partitioned between EtOAc and water, the phases separated, the aqueous phase extracted twice with EtOAc, the organic phases combined, washed with brine, dried over MgSO₄, filtered and concentrated to an amber oil. The crude material was purified by flash chromatography (SiO₂, eluted successively with DCM/hexanes (1:1), DCM, and EtOAc/hexanes (1:4)) to give the title compound (22.25 g, 58 mmol, 63%) as a pale yellow oil. ES-LCMS m/z 404.30(M+Na).

Preparation 12B: 1,1-dimethylethyl methyl[((1R,2R)-1-phenyl-2-{[(phenylmethyl)oxy]methyl}cyclopropyl)methyl]carbamate

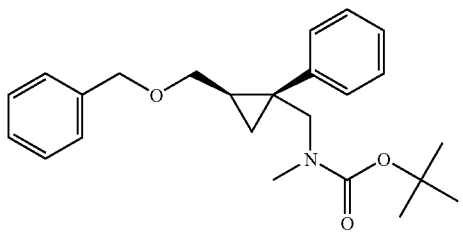

To a solution of 1,1-dimethylethyl [((1R,2R)-1-phenyl-2-{[(phenylmethyl)oxy]methyl}cyclopropyl)methyl]carbamate (7.5 g, 20.4 mmol), accessed via the method of 11B, and methyl iodide (14.4 g, 102.0 mmol, 5 eq) in 100 mL THF cooled to 0° C. was added 1M sodium bis(trimethylsilyl)amide in THF (30.6 mL, 30.6 mmol, 1.5 eq). The reaction mixture was stirred 8 h at 0° C. followed by 16 h at ambient temperature. The reaction mixture was partitioned between EtOAc and water, the phases separated, the aqueous phase extracted twice with EtOAc, the organic phases combined, washed with brine, dried over MgSO$_4$, filtered and concentrated to an amber oil. The crude material was purified by flash chromatography (SiO$_2$, eluted with EtOAc/hexanes (1:4)) to give the title compound (3.1 g, 8.1 mmol, 40%) as a pale yellow oil. $^1$H NMR (400 MHz, CDCl$_3$) δ 7.34-7.18 (m, 10H), 4.36-4.27 (m, 2H), 3.67-3.45 (m, 1H), 3.26-3.13 (m, 2H), 3.07-2.99 (m, 1H), 2.77-2.62 (m, 3H), 1.39-0.80 (m, 12H). ES-LCMS m/z 404.2 (M+Na).

Preparation 13A: 1,1-dimethylethyl {[(1S,2R)-2-(hydroxymethyl)-1-phenylcyclopropyl]methyl}methylcarbamate

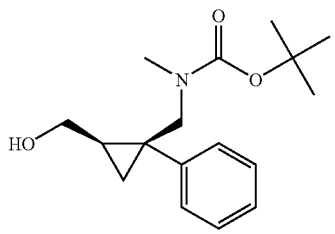

1,1-dimethylethyl methyl[((1S,2R)-1-phenyl-2-{[(phenylmethyl)oxy]methyl}cyclopropyl)methyl]carbamate (20.65 g, 54 mmol), accessed via the method of Preparation 12A, was combined with 10% palladium on activated carbon (2.00 g) in 250 mL ethyl alcohol and hydrogenated under 1 atm H$_2$(g) for 3 h at ambient temperature. The catalyst was filtered off through celite and the filtrate concentrated to a yellow oil. The crude material was purified by flash chromatography on silica eluted with 5→25% EtOAc/DCM. Appropriate fractions were combined and concentrated to give the title compound (12.02 g, 41.2 mmol, 76%) as a colorless oil. $^1$H NMR (300 MHz, DMSO-d6, 90° C.) δ 7.30-7.22 (m, 9H), 7.15 (m, 1H), 4.41 (t, J=5.1 Hz, 1H), 3.87 (d, J=14.5 Hz, 1H), 3.74 (m, 1H), 3.52 (m, 1H), 3.31 (d, J=14.4 Hz, 1H), 2.63 (s, 3H), 1.21 (s, 9H), 1.20-1.07 (m, 2H), 0.77 (m, 1H). ES-LCMS m/z 314.21 (M+Na).

Preparation 13B: 1,1-dimethylethyl {[(1R,2R)-2-(hydroxymethyl)-1-phenylcyclopropyl]methyl}methylcarbamate

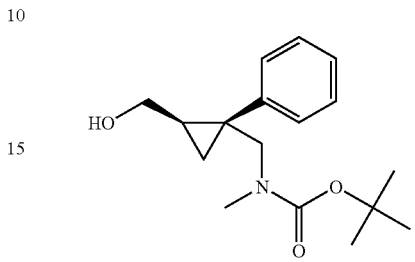

1,1-dimethylethyl methyl[((1R,2R)-1-phenyl-2-{[(phenylmethyl)oxy]methyl}cyclopropyl)methyl]carbamate (3.1 g, 8.1 mmol), accessed via the method of Preparation 12B, was combined with 10% palladium on activated carbon (0.50 g) in ethyl alcohol and hydrogenated under 1 atm H$_2$(g) for 0.5 h at ambient temperature. The catalyst was filtered off through celite and the filtrate concentrated to a colorless oil. The crude material was purified by flash chromatography (SiO$_2$, eluted with EtOAc/hexanes (4:6)) to give the title compound (2.2 g, 7.5 mmol, 95%) as a pale yellow oil. $^1$H NMR (400 MHz, CDCl$_3$) δ 7.32-7.20 (m, 5H), 3.70-3.54 (m, 1H), 3.34-3.18 (m, 3H), 2.76-2.60 (m, 3H), 1.41-1.22 (m, 11H), 1.00 (m, 1H), 0.87-0.85 (m, 1H). ES-LCMS m/z 314.1 (M+Na).

Preparation 13C: 1,1-dimethylethyl {[(1R,2R)-2-(hydroxymethyl)-1-phenylcyclopropyl]methyl}carbamate

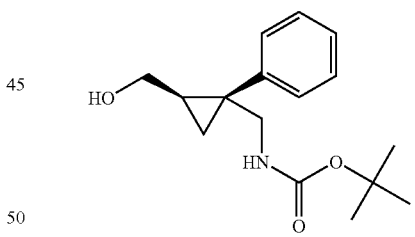

1,1-dimethylethyl [((1R,2R)-1-phenyl-2-{[(phenylmethyl)oxy]methyl}cyclopropyl)methyl]carbamate (8.0 g, 21.7 mmol), accessed via the method of Preparation 11B, was combined with 10% palladium on activated carbon (0.8 g) in ethyl alcohol and hydrogenated under 1 atm H$_2$(g) for 2.5 h at ambient temperature. The catalyst was filtered off through celite and the filtrate concentrated to a colorless oil. The crude material was purified by flash chromatography (SiO$_2$, eluted with EtOAc/hexanes (4:6)) to give the title compound (5.8 g, 20.9 mmol, 96%) as a pale yellow oil. $^1$H NMR (400 MHz, CDCl$_3$) δ 7.35-7.25 (m, 5H), 3.52-3.48 (m, 1H), 3.35-3.30 (m, 1H), 3.23-3.19 (m, 1H), 3.10-3.07 (m, 1H), 1.45-1.37 (m, 11H), 1.04-1.04 (m, 1H), 0.87-0.84 (m, 1H). LCMS m/z 300.1 (M+Na).

Preparation 14A: 1,1-dimethylethyl {[(1S,2R)-2-formyl-1-phenylcyclopropyl]methyl}methylcarbamate

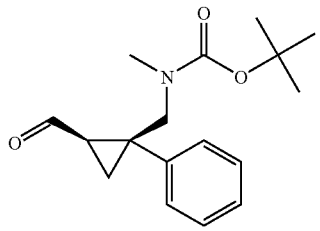

1,1-dimethylethyl {[(1S,2R)-2-(hydroxymethyl)-1-phenylcyclopropyl]methyl}methylcarbamate (12.02 g, 41.2 mmol), accessed via the method of Preparation 13A, was dissolved in 200 mL DCM with 6.2 mL 2-methylpropan-2-ol and treated with Dess-Martin Periodinane (28.0 g, 66.0 mmol, 1.6 eq) in 200 mL DCM at ambient temperature for 3 h. The reaction mixture was diluted with 1 L diethyl ether and treated with 400 mL 1N NaOH at ambient temperature for 30 min. The organic phase was separated, the aqueous phase extracted twice with diethyl ether, the organic phases combined, washed with brine, dried over MgSO$_4$, filtered and concentrated to a colorless oil. The crude material was purified by flash chromatography (SiO$_2$, eluted with EtOAc/hexanes (1:4)) to give the title compound (10.7, 36.9 mmol, 89%). $^1$H NMR (400 MHz, CDCl$_3$) δ 9.77-9.65 (m, 1H), 7.33-7.23 (m, 5H), 3.75-3.63 (m, 2H), 2.72-2.50 (m, 3H), 2.26-2.19 (m, 1H), 1.87-1.81 (m, 1H), 1.65-1.61 (m, 1H), 1.31-1.18 (m, 9H). LCMS m/z 312.2 (M+Na).

Preparation 14B: 1,1-dimethylethyl {[(1R,2R)-2-formyl-1-phenylcyclopropyl]methyl}methylcarbamate

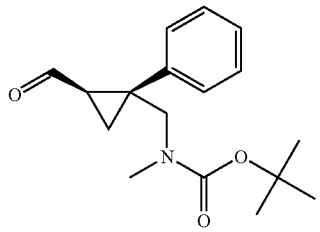

1,1-dimethylethyl {[(1R,2R)-2-(hydroxymethyl)-1-phenylcyclopropyl]methyl}methylcarbamate (3.8 g, 13.0 mmol), accessed via the method of Preparation 13B, was dissolved in 35 mL DCM with 1.1 mL 2-methylpropan-2-ol and treated with Dess-Martin Periodinane (8.8 g, 20.8 mmol, 1.6 eq) in 35 mL DCM at ambient temperature for 2 h. The reaction mixture was diluted with 50 mL diethyl ether and treated with 50 mL 1N NaOH at ambient temperature for 15 min. The organic phase was separated, the aqueous phase extracted twice with diethyl ether, the organic phases combined, washed with brine, dried over MgSO$_4$, filtered and concentrated to a colorless oil. The crude material was purified by flash chromatography (SiO$_2$, eluted EtOAc/hexanes (3:7)) to give the title compound (3.2 g, 11.0 mmol, 84%). $^1$H NMR (400 MHz, CDCl$_3$) δ 8.49-8.47 (m, 1H), 7.29-7.24 (m, 5H), 3.62-3.58 (m, 1H), 3.33-3.22 (m, 1H), 2.72-2.58 (m, 3H), 1.84-1.81 (m, 1H), 1.71-1.53 (m, 1H), 1.34-1.25 (m, 10H). ES-LCMS m/z 312.2 (M+Na).

Preparation 14C: 1,1-dimethylethyl {[(1R,2R)-2-formyl-1-phenylcyclopropyl]methyl}carbamate

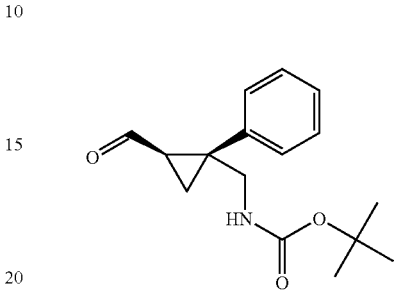

1,1-dimethylethyl {[(1R,2R)-2-(hydroxymethyl)-1-phenylcyclopropyl]methyl}carbamate (5.8 g, 20.9 mmol), accessed via the method of Preparation 13C, was dissolved in 100 mL DCM with 3.1 mL 2-methylpropan-2-ol and treated with Dess-Martin Periodinane (14.1 g, 33.4 mmol, 1.6 eq) in 100 mL DCM at ambient temperature for 3 h. The reaction mixture was diluted with 500 mL diethyl ether and treated with 200 mL 1N NaOH at ambient temperature for 15 min. The organic phase was separated, the aqueous phase extracted twice with diethyl ether, the organic phases combined, washed with brine, dried over MgSO$_4$, filtered and concentrated to a colorless oil. The crude material was purified by flash chromatography (SiO$_2$, eluted with EtOAc/hexanes (1:4)) to give the title compound (4.2 g, 15.2 mmol, 73%). $^1$H NMR (400 MHz, CDCl$_3$) δ 8.51-8.50 (m, 1H), 7.34-7.24 (m, 5H), 4.55 (m, 1H), 3.44-3.39 (m, 1H), 3.25-3.20 (m, 1H), 2.13-2.08 (m, 1H), 1.80-1.78 (m, 1H), 1.64-1.61 (m, 1H), 1.37 (s, 9H). ES-LCMS m/z 298.1 (M+Na).

Preparation 14D: 1,1-dimethylethyl {[(1R,2S)-2-formyl-1-phenylcyclopropyl]methyl}methylcarbamate

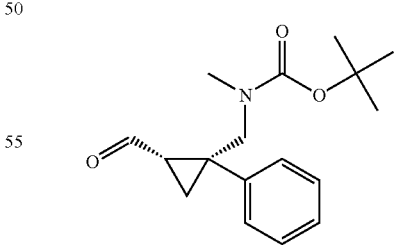

Starting from phenylacetonitrile and (2R)-2-hydroxy-3-[(phenylmethyl)oxy]propyl 4-methylbenzenesulfonate and using the methods of Preparations 1, 2, 3A, 4A, 11A, 12A, 13A and 14A sequentially, the title product can be obtained in comparable yields and analytical characterization to those obtained in those preparations.

Preparation 14E: 1,1-dimethylethyl {[(1S,2S)-2-formyl-1-phenylcyclopropyl]methyl}methylcarbamate

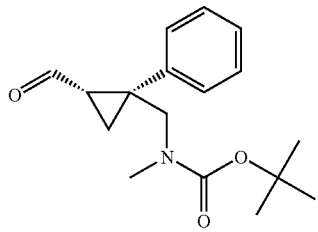

Starting from phenylacetonitrile and (2R)-2-hydroxy-3-[(phenylmethyl)oxy]propyl 4-methylbenzenesulfonate and using the methods of Preparations 1, 2, 3B, 4B, 11B, 12B, 13B, and 14B sequentially, the title product can be obtained in comparable yields and analytical characterization to those obtained in those preparations.

Preparation 14F: 1,1-dimethylethyl {[(1S,2S)-2-formyl-1-phenylcyclopropyl]methyl}carbamate

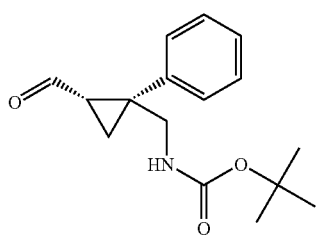

Starting from phenylacetonitrile and (2R)-2-hydroxy-3-[(phenylmethyl)oxy]propyl 4-methylbenzenesulfonate and using the methods of Preparations 1, 2, 3B, 4B, 11B, 13C, and 14C sequentially, the title product can be obtained in comparable yields and analytical characterization to those obtained in those preparations.

Preparation 15: Compounds of generic structure:

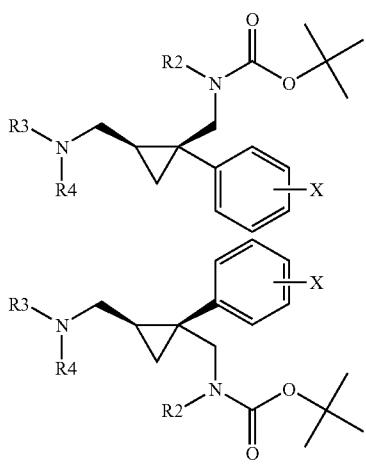

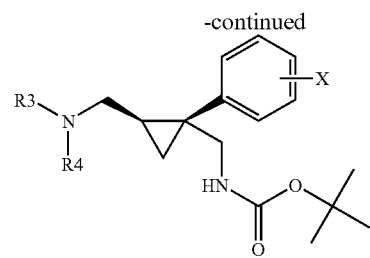

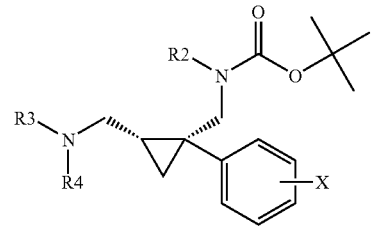

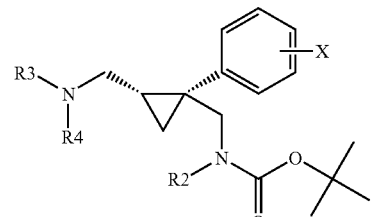

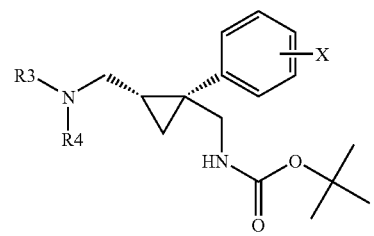

In combinatorial fashion, aldehydes prepared by the methods of Preparations 14A-F (0.35 mmol) in 3 mL DCE were treated with various secondary amines (0.35 mmol, 1 eq) and mp-sodium triacetoxyborohydride (500 mg, 1.04 mmol, 3 eq) at ambient temperature for 20 h with continuous agitation. The reaction mixtures were each filtered. The remaining resin was treated with 4 mL DCM with agitation for 1 h and the organics separated via filtration. The organic filtrates were concentrated to dryness and carried forward without purification or characterization.

Preparation 16: Compounds of generic structure:

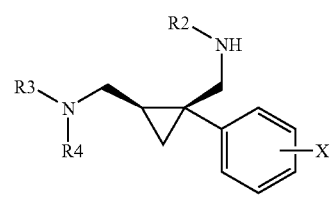

-continued

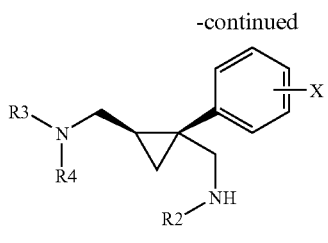

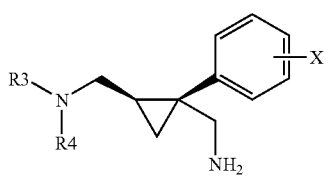

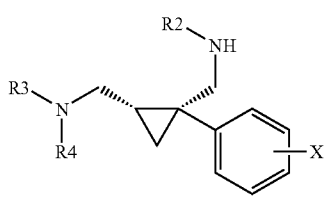

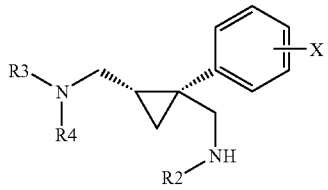

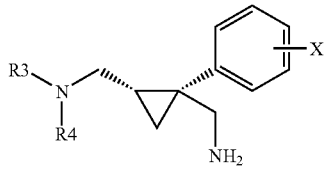

-continued

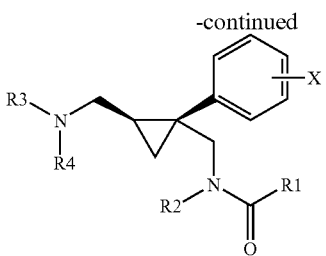

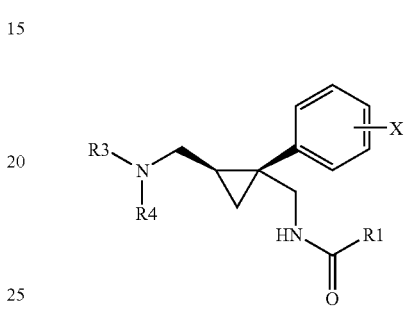

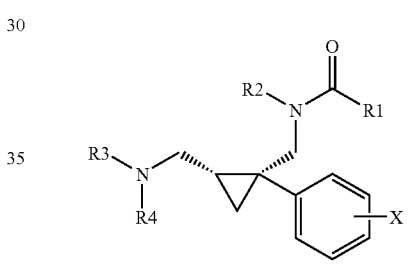

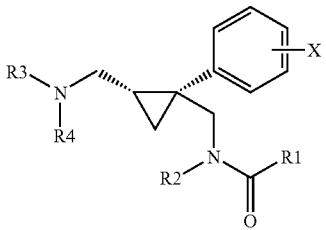

Compounds prepared by the method of Preparation 15 were treated with 1 mL trifluoroacetic acid in 2 mL DCM and 2 mL DCE for 5 h at ambient temperature with slight agitation. The reaction mixtures were concentrated and partitioned between DCM (2 mL) and saturated NaHCO$_3$ (2 mL) and the organic phases separated via filtration through hydrophobic frit tube assemblies. The organic filtrates were concentrated to dryness and carried forward without purification or characterization.

Preparation 17: Compounds of general formula:

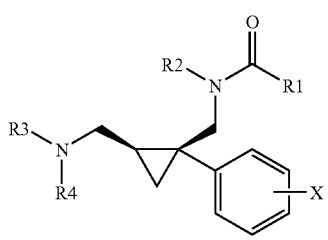

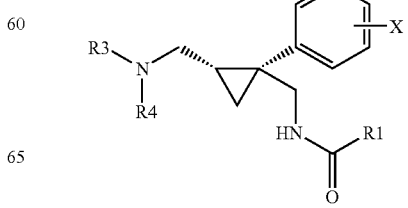

The compounds prepared according to the method of Preparation 16 were dissolved in 3 mL DCE and further split out in combinatorial fashion such that each reaction was performed on a theoretical scale of 0.12 mmol in 1 mL DCE. The reaction plates were concentrated down and the residues taken up in 1 mL DMF for reaction. Polymer-bound diisopropylamine (0.48 mmol, 4 eq) was added to each well followed by an acid (0.13 mmol, 1.1 eq) in 0.5 mL DMF and HATU (0.12 mmol, 1 eq) in 0.5 mL DMF. The resultant reaction mixtures were agitated at ambient temperature for 18 h and HATU byproducts scavenged by addition of polymer-bound carbonate (0.36 mmol, 3 eq) and agitation at ambient temperature for 3 h. The reaction plates were filtered and the filtrates concentrated to dryness. Crude products were dissolved in 300 microliters of DMSO and brought up to a final volume of 500 microliters using methanol. This 500 microliter solution was injected by a Waters 2767 autosampler into an XTerra C18 5 micron particle HPLC column (19 mm×150 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. Chiral HPLC was performed on representative samples to confirm that homochiral integrity had been preserved.

Preparation 18: Compounds of general formula:

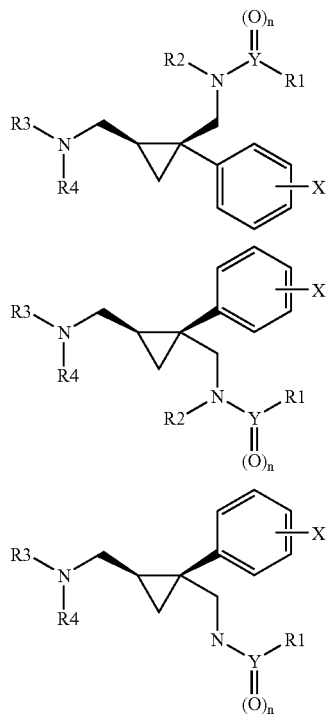

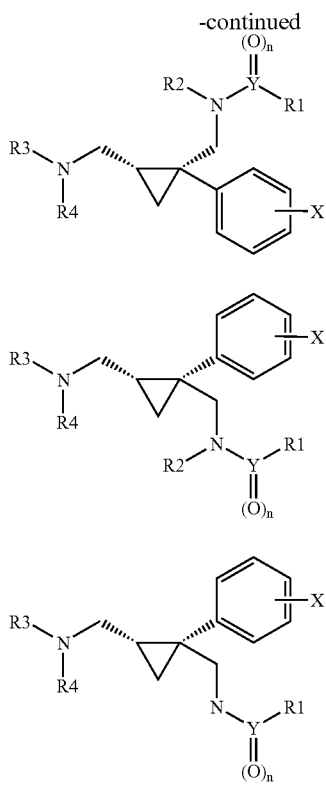

The compounds prepared according to the method of Preparation 16 were dissolved in 3 mL DCE (1:1) and further split out in combinatorial fashion such that each reaction was performed on a theoretical scale of 0.12 mmol in 1 mL DCE. Polymer-bound diisopropylamine (0.48 mmol, 4 eq) was added to each well followed by either an acid chloride or sulfonyl chloride (0.12 mol, 1 eq) in 1 mL DCE. The resultant reaction mixtures were agitated at ambient temperature for 16 h and excess acid or sulfonyl chloride scavanged by addition of polymer-bound trisamine (0.36 mmol, 3 eq) and agitation at ambient temperature for 4 h. The reaction plates were filtered and the filtrates concentrated to dryness. Crude products were dissolved in 300 microliters of DMSO and brought up to a final volume of 500 microliters using methanol. This 500 microliter solution was injected by a Waters 2767 autosampler into an XTerra C18 5 micron particle HPLC column (19 mm×150 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. Chiral HPLC was performed on representative samples to confirm that homochiral integrity had been preserved.

The following demonstrate the above-referenced general scheme:

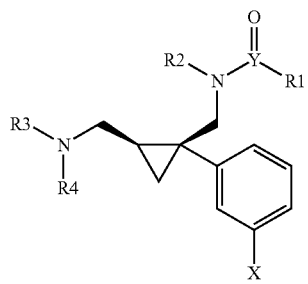

| Example # | R3—N—R4 | —Y(O)ₙR1 | X | % Yield | LCMS ES | Ion | Preparation |
|---|---|---|---|---|---|---|---|
| 7 | (2-methylbenzimidazolyl-azabicyclic) | phenylsulfonyl | Cl | | 589.6, 591.5 | (M + H) | 18 |
| 8 | (2-methylbenzimidazolyl-azabicyclic) | 2-furyl carbonyl | Cl | | 543.5, 545.5 | (M + H) | 18 |
| 9 | naphthalenesulfonamido-piperidinylmethyl | 2-furyl carbonyl | Cl | | 606.5, 608.5 | (M + H) | 18 |
| 10 | (2-methylbenzimidazolyl-azabicyclic) | cyclopentylcarbonyl | Cl | | 545.5, 547.6 | (M + H) | 18 |
| 11 | phenyl-oxadiazolyl-piperidinyl | phenylsulfonyl | H | 62 | 543.4 | (M + H) | 18 |

As will be appreciated by those skilled in the art, additional compounds of the ent invention may be similarly prepared according to the schemes provided herein.

Scheme 3:
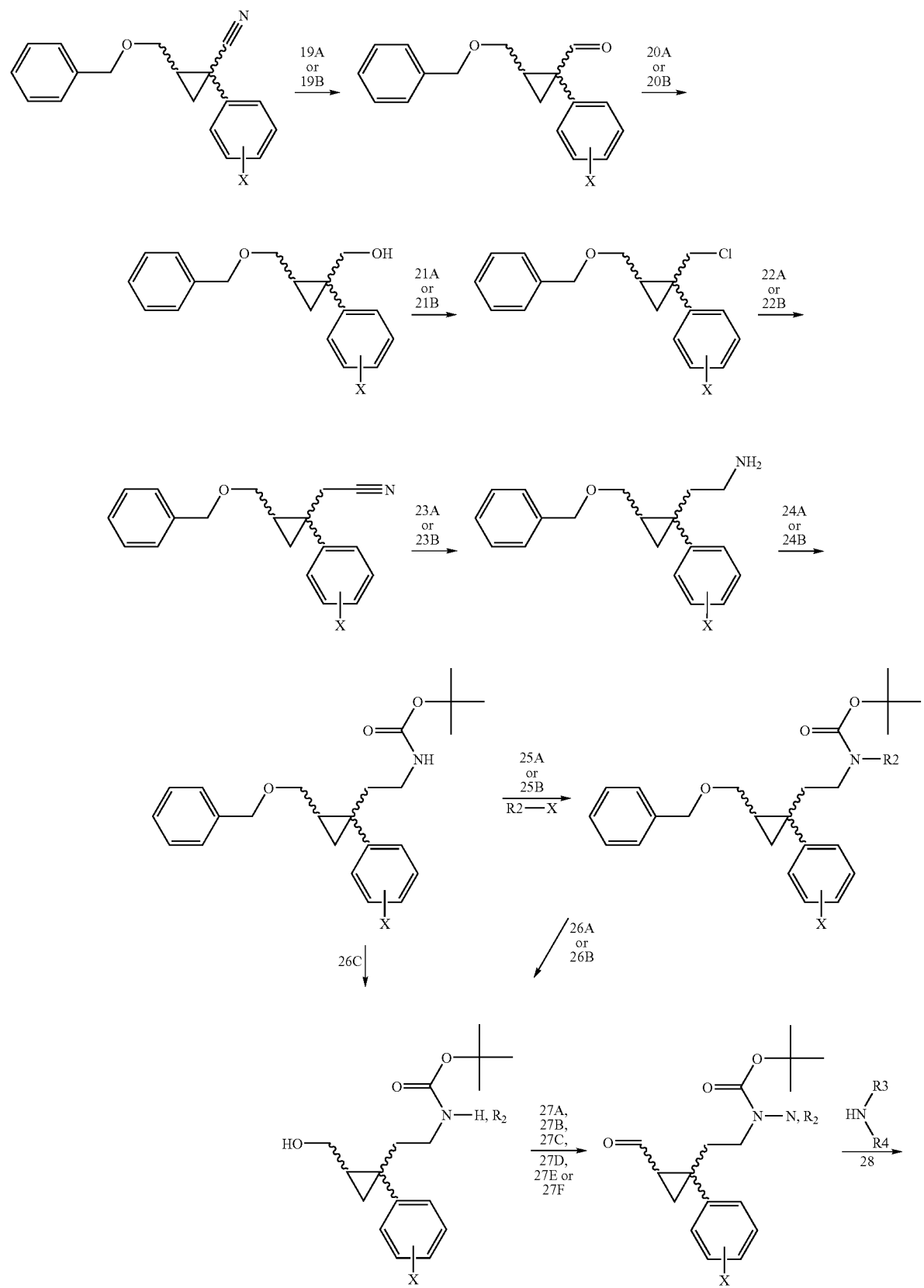

-continued

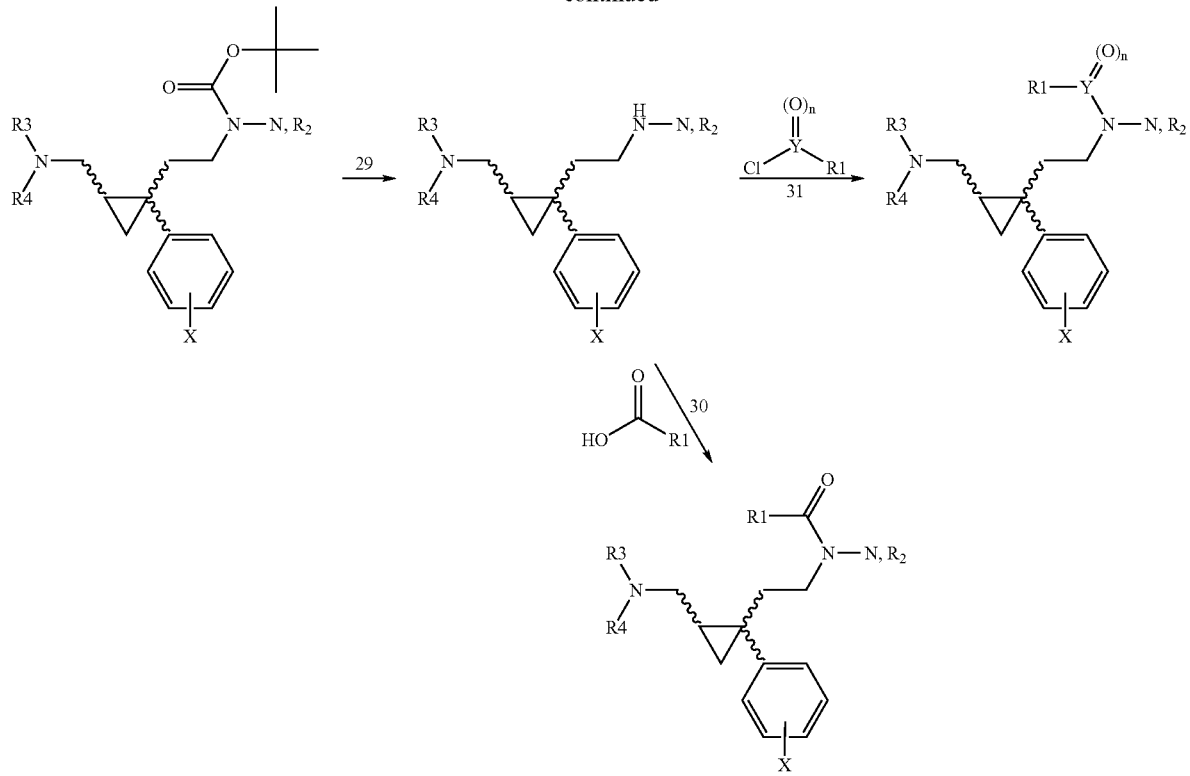

Where:

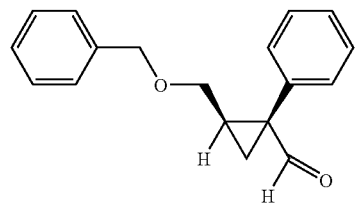 = an acid chloride or a sulfonyl chloride

R2—X = an alkyl halide

Preparation 19B: (1R,2R)-1-phenyl-2-{[(phenylmethyl)oxy]methyl}cyclopropanecarbaldehyde

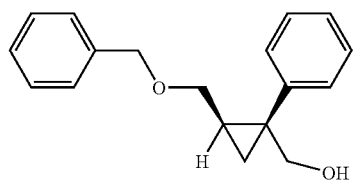

To a solution of 300 mL toluene and (1R,2R)-1-phenyl-2-{[(phenylmethyl)oxy]methyl}cyclopropanecarbonitrile (12.0 g, 45.57 mmol, 1 eq), accessed via the method of Preparation 3B, at 0° C. was added 59.3 mL 1M diisobutylaluminum hydride (59.3 mmol, 1.3 eq) in tetrahydrofuran. The mixture was stirred at 0° C. for 4 h and then at ambient temperature for 18 h before dilution with 500 mL toluene and 500 mL water. The mixture was stirred for 30 min and then filtered through a pad of celite. The organics were isolated, dried over $Na_2SO_4$, filtered and concentrated to give the title compound (7.8 g, 29.3 mmol, 64%) as a yellow oil. $^1$H NMR (400 MHz, $CDCl_3$) δ 9.39 (s, 1H), 7.39-7.19 (m, 10H), 4.33-4.23 (m, 2H), 3.36-3.33 (m, 1H), 3.03-2.98 (m, 1H), 2.16-2.11 (m, 1H), 1.77-1.73 (m, 1H), 1.46-1.43 (m, 1H).

Preparation 20B: ((1R,2R)-1-phenyl-2-{[(phenylmethyl)oxy]methyl}cyclopropyl)methanol Sodium borohydride (1.2 g, 32.2 mmol, 1 eq) was added in one portion to a mixture of (1R,2R)-1-phenyl-2-{[(phenylmethyl)oxy]methyl}cyclopropanecarbaldehyde (7.8 g, 29.3 mmol, 1 eq), accessed via the method of Preparation 19B, in 100 mL ethyl alcohol at ambient temperature. The reaction was stirred at ambient temperature for 18 h, concentrated down and the residue partitioned between ethyl acetate and brine. The organics were dried over $Na_2SO_4$, filtered and concentrated to give a yellow oil. The crude material was purified by flash chromatography ($SiO_2$, eluted successively with hexanes and EtOAc/hexanes (1:4)) to give the title product (7.8 g, 29.06 mmol, 99%) as a clear oil. $^1$H NMR (400 MHz, DMSO-$d_6$) δ 7.31-7.15 (m, 10H), 4.61 (t, J=5.7 Hz, 1H), 4.30-4.17 (m, 2H), 3.53-3.48 (m, 1H), 3.35-3.31 (m, 1H), 3.02-2.95 (m, 2H), 1.40-1.33 (m, 1H), 0.96-0.93 (m, 1H), 0.72-0.69 (m, 1H). ES-LCMS m/z 291.2 (M+Na).

Preparation 21B: [({[(1R,2R)-2-(chloromethyl)-2-phenylcyclopropyl]methyl}oxy)methyl]benzene

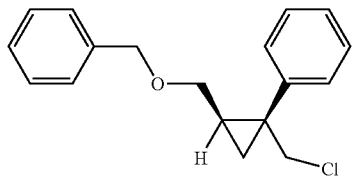

A mixture of polymer-bound triphenylphosphine (31.64 g, 67.08 mmol, 3 eq) and carbon tetrachloride (6.5 mL, 67.08 mmol, 3 eq) in 300 mL DCM was stirred at ambient temperature for 30 min. To this was added a solution of ((1R,2R)-1-phenyl-2{[(phenylmethyl)oxy]methyl}cyclopropyl)methanol (6.0 g, 22.36 mmol, 1 eq), accessed via the method of Preparation 20B, in 50 mL DCM and the entire reaction mixture was stirred at ambient temperature for 16 h. The mixture was then filtered and the resin washed with excess DCM. The organics were concentrated down to give the title compound (6.4 g, 22.36 mmol, 100%) as a clear oil. $^1$H NMR (400 MHz, DMSO-$d_6$) δ 7.38-7.17 (m, 10H), 4.31-4.16 (m, 2H), 4.10-4.07 (m, 1H), 3.56-3.53 (m, 1H), 3.08-3.04 (m, 1H), 2.92-2.87 (m, 1H), 1.63-1.56 (m, 1H), 1.08-0.99 (m, 2H).

Preparation 22B: ((1R,2R)-1-phenyl-2-{[(phenylmethyl)oxy]methyl}cyclopropyl)acetonitrile

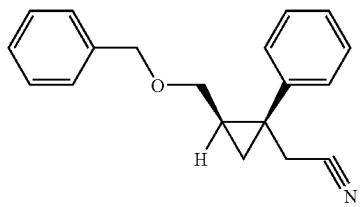

A mixture of [({[(1R,2R)-2-(chloromethyl)-2-phenylcyclopropyl]methyl}oxy)methyl]benzene [(1R,2R)-2-(chloromethyl)-2-phenylcyclopropyl]methyl phenylmethyl diethyl ether (6.4 g, 22.32 mmol, 1 equiv), accessed via the method of Preparation 21B, potassium cyanide (2.18 g, 33.47 mmol, 1.5 eq) and potassium carbonate (6.17 g, 44.63 mmol, 2 eq) in 200 mL DMF was heated to 80° C. for 18 h. The reaction was then partitioned between ethyl acetate and water. The organics were washed with water (3×) and brine, dried over Na$_2$SO$_4$, filtered and concentrated down. The crude material was purified by flash chromatography (SiO$_2$, eluted successively with hexanes and EtOAc/hexanes (1:4)) to give the title product (5.2 g, 18.13 mmol, 81%) as a clear oil. $^1$H NMR (400 MHz, DMSO-$d_6$) δ 7.39-7.16 (m, 10H), 4.30-4.15 (m, 2H), 3.09-3.01 (m, 2H), 2.88-2.84 (m, 1H), 2.65-2.61 (m, 1H), 1.51-1.44 (m, 1H), 1.04-1.00 (m, 1H), 0.94-0.92 (m, 1H).

Preparation 23B: [2-((1R,2R)-1-phenyl-2-{[(phenylmethyl)oxy]methyl}cyclopropyl)ethyl]amine

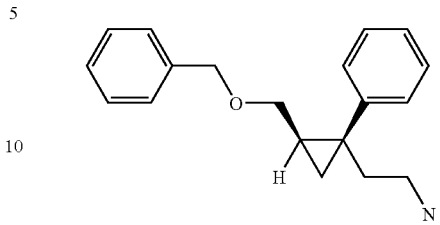

To 18.13 mL 1M lithium aluminum hydride (18.13 mmol) in diethyl ether at 0° C. was added ((1R,2R)-1-phenyl-2-{[(phenylmethyl)oxy]methyl)cyclopropyl)acetonitrile (5.2 g, 18.13 mmol), accessed via the method of Preparation 22B, dissolved in 20 mL diethyl ether. After complete addition, the reaction mixture was stirred at 0° C. for 3 h. The reaction mixture was diluted with 400 mL diethyl ether and quenched with successive addition of 0.6 mL water, 0.6 mL 15% NaOH, and 3.0 mL water. The reaction mixture was filtered through a pad of celite and the filtrate was concentrated to give the title product (5.1 g, 18.13 mmol 100%) as a clear oil. $^1$H NMR (400 MHz, DMSO-$d_6$) δ 7.29-7.14 (m, 10H), 4.29-4.16 (m, 2H), 3.04-2.99 (m, 1H), 2.91-2.86 (m, 1H), 2.39-2.27 (m, 2H), 1.88-1.83 (m, 1H), 1.28-1.19 (m, 2H), 0.84-0.81 (m, 1H), 0.73-0.71 (m, 1H).

Preparation 24B: 1,1-dimethylethyl [2-((1R,2R)-1-phenyl-2-{[(phenylmethyl)oxy]methyl}cyclopropyl)ethyl]carbamate

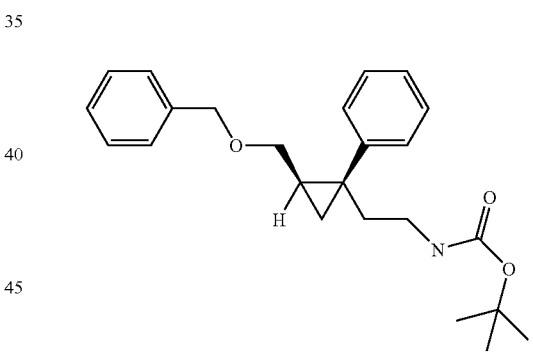

To a solution of [2-((1R,2R)-1-phenyl-2-{[(phenylmethyl)oxy]methyl}cyclopropyl)ethyl]amine (5.1 g, 18.12 mmol, 1 eq), accessed via the method of 23B, and triethylamine (2.78 mL, 19.03 mmol, 1.1 eq) in 75 mL DCM cooled to 0° C. was added di(tert-butyl) dicarbonate (4.15 g, 19.03 mmol, 1.05 eq). The resultant mixture was stirred 2 h at 0° C. followed by 16 h at ambient temperature. The reaction mixture was diluted with DCM, washed successively with saturated NaHCO$_3$ and brine, dried over MgSO$_4$, filtered and concentrated down. The crude material was purified by flash chromatography (SiO$_2$, eluted successively with hexanes and EtOAc/hexanes (1:4)) to give the title product (5.9 g, 15.46 mmol, 85%) as a clear oil. $^1$H NMR (400 MHz, DMSO-$d_6$) δ 7.29-7.17 (m, 10H), 6.60-6.58 (m, 1H), 4.29-4.16 (m, 2H), 3.01-2.97 (m, 1H), 2.91-2.87 (m, 1H), 2.83-2.77 (m, 1H), 2.71-2.66 (m, 1H), 1.91-1.85 (m, 1H), 1.33-1.21 (m, 11H), 0.83-0.80 (m, 1H), 0.74-0.72 (m, 1H). ES-LCMS m/z 404.2 (M+Na).

Preparation 26C: 1,1-dimethylethyl {2-[(1R,2R)-2-(hydroxymethyl)-1-phenylcyclopropyl]ethyl}carbamate

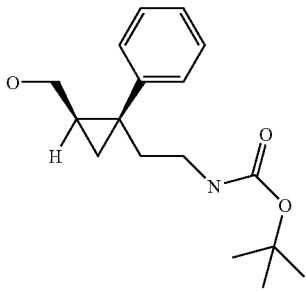

1,1-dimethylethyl [2-((1R,2R)-1-phenyl-2-{[(phenylmethyl)oxy]methyl}cyclopropyl)ethyl]carbamate (5.9 g, 15.46 mmol), accessed via the method of Preparation 24B was combined with 10% palladium on activated carbon (600 mg) in 100 mL ethyl alcohol and hydrogenated under 1 atm $H_2(g)$ for 3 h at ambient temperature. The catalyst was filtered off through celite and the filtrate concentrated to give the title compound (4.1 g, 14.07 mmol, 91%) as a colorless oil. $^1$H NMR (400 MHz, DMSO-$d_6$) δ 7.27-7.12 (m, 5H), 6.59-6.56 (m, 1H), 4.31-4.29 (m, 1H), 3.00-2.94 (m, 1H), 2.87-2.66 (m, 3H), 1.88-1.82 (m, 1H), 1.32-1.25 (m, 10H), 1.11-1.05 (m, 1H), 0.76-0.73 (m, 1H), 0.65-0.63 (m, 1H). ES-LCMS m/z 314.1 (M+Na).

Preparation 27C: 1,1-dimethylethyl {2-[(1R,2R)-2-formyl-1-phenylcyclopropyl]ethyl}carbamate

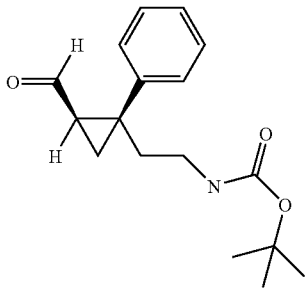

1,1-dimethylethyl {2-[(1R,2R)-2-(hydroxymethyl)-1-phenylcyclopropyl]ethyl}carbamate (4.1 g, 14.07 mmol), accessed via the method of Preparation 26C, was dissolved in 40 mL DCM with 1.2 mL 2-methylpropan-2-ol and treated with Dess-Martin Periodinane (9.55 g, 22.51 mmol, 1.6 eq) in 40 mL DCM at ambient temperature for 3 h. The reaction mixture was diluted with 50 mL diethyl ether and treated with 50 mL 1N NaOH at ambient temperature for 30 min. The organic phase was separated, the aqueous phase extracted twice with diethyl ether, the organic phases combined, washed with brine, dried over $MgSO_4$, filtered and concentrated to a colorless oil. The crude material was purified by flash chromatography ($SiO_2$, eluted with EtOAc/hexanes (3:7)) to give the title compound (3.5 g, 12.10 mmol, 86%). $^1$H NMR (400 MHz, $CDCl_3$) δ 8.43-8.41 (m, 1H), 7.31-7.20 (m, 5H), 4.41 (m, 1H), 3.04-2.95 (m, 2H), 2.16-2.10 (m, 1H), 1.99-1.94 (m, 1H), 1.88-1.85 (m, 1H), 1.54-1.46 (m, 1H), 1.38 (s, 10H). LCMS m/z 312.2 (M+Na).

Preparation 27F: 1,1-dimethylethyl {2-[(1S,2S)-2-formyl-1-phenylcyclopropyl]ethyl}carbamate

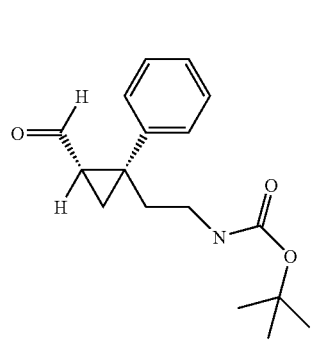

Starting from (1S,2S)-1-phenyl-2-{[(phenylmethyl)oxy]methyl}cyclopropanecarbonitrile, accessed via the method of 3B, and using the methods of Preparations 19B, 20B, 21B, 22B, 23B, 24B, 26C, and 27C sequentially, the title product can be obtained in comparable yields and analytical characterization to those obtained in those preparations.

Preparation 28: Compounds of generic structure:

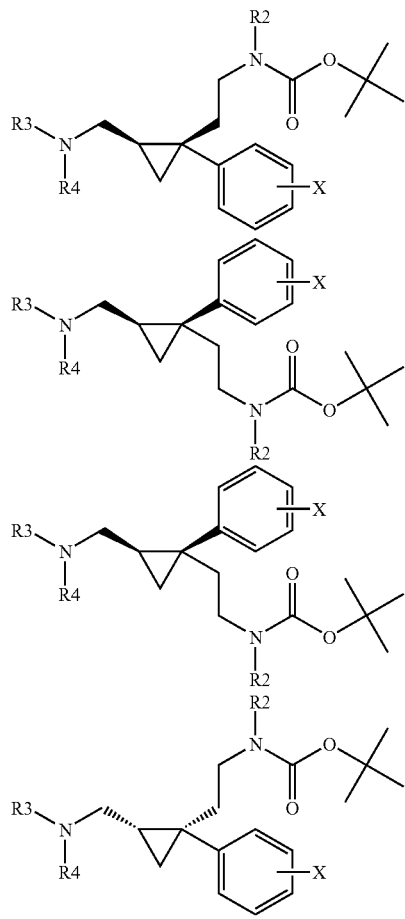

-continued

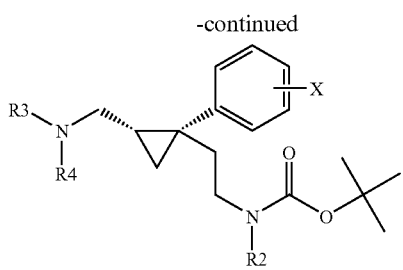

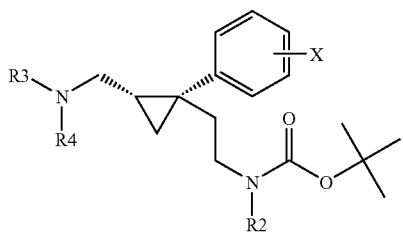

In combinatorial fashion, aldehydes prepared by the methods of Preparations 27A-F (0.35 mmol) in 3 mL DCE were treated with various secondary amines (0.35 mmol, 1 eq) and mp-sodium triacetoxyborohydride (500 mg, 1.04 mmol, 3 eq) at ambient temperature for 20 h with continuous agitation. The reaction mixtures were each filtered. The remaining resin was treated with 4 mL DCM with agitation for 1 h and the organics separated via filtration. The organic filtrates were concentrated to dryness and carried forward without purification or characterization.

Preparation 29: Compounds of generic structure:

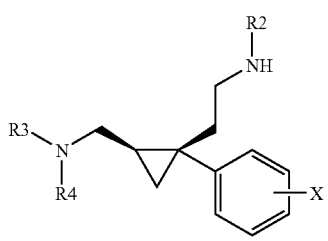

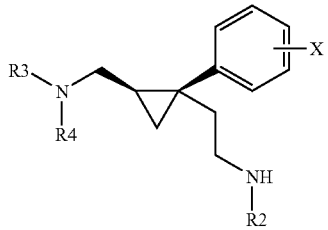

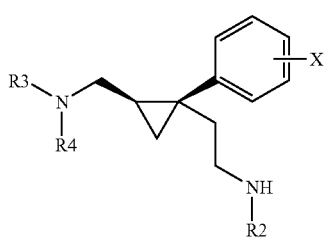

-continued

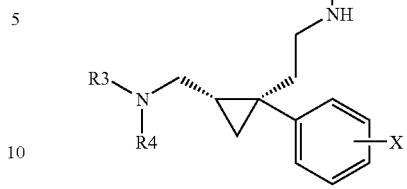

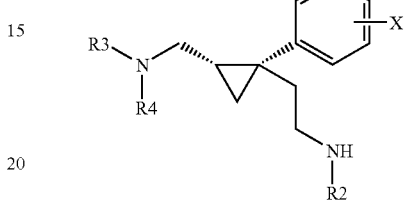

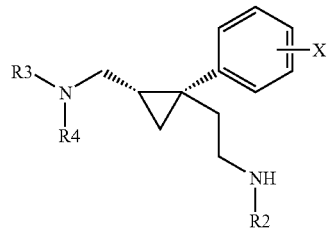

Compounds prepared by the method of Preparation 28 were treated with 1 mL trifluoroacetic acid in 2 mL DCM and 2 mL DCE for 5 h at ambient temperature with slight agitation. The reaction mixtures were concentrated and partitioned between DCM (2 mL) and saturated $NaHCO_3$ (2 mL) and the organic phases separated via filtration through hydrophobic frit tube assemblies. The organic filtrates were concentrated to dryness and carried forward without purification or characterization.

Preparation 30: Compounds of general formula:

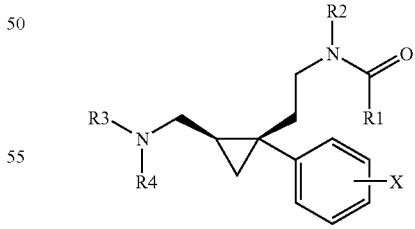

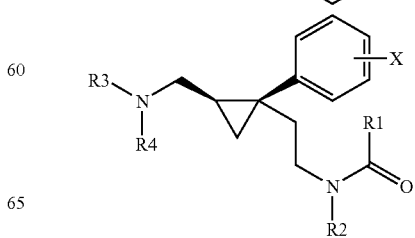

-continued

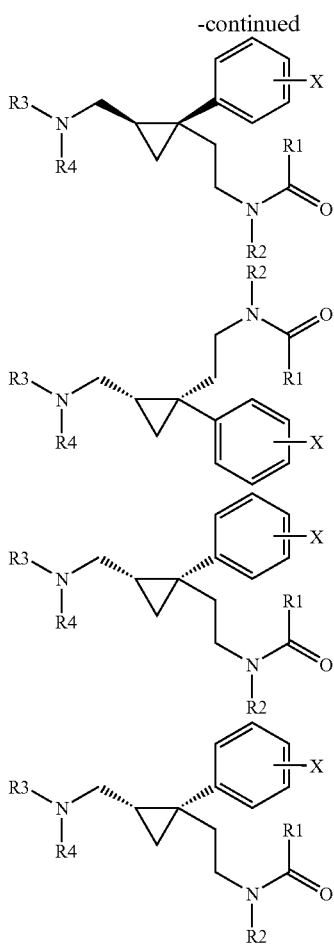

The compounds prepared according to the method of Preparation 29 were dissolved in 3 mL DCE and further split out in combinatorial fashion such that each reaction was performed on a theoretical scale of 0.12 mmol in 1 mL DCE. The reaction plates were concentrated down and the residues taken up in 1 mL DMF for reaction. Polymer-bound diisopropylamine (0.48 mmol, 4 eq) was added to each well followed by an acid (0.13 mmol, 1.1 eq) in 0.5 mL DMF and HATU (0.12 mmol, 1 eq) in 0.5 mL DMF. The resultant reaction mixtures were agitated at ambient temperature for 18 h and HATU byproducts scavanged by addition of polymer-bound carbonate (0.36 mmol, 3 eq) and agitation at ambient temperature for 3 h. The reaction plates were filtered and the filtrates concentrated to dryness. Crude products were dissolved in 300 microliters of DMSO and brought up to a final volume of 500 microliters using methanol. This 500 microliter solution was injected by a Waters 2767 autosampler into an XTerra C18 5 micron particle HPLC column (19 mm×150 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. Chiral HPLC was performed on representative samples to confirm that homochiral integrity had been preserved.

Preparation 31: Compounds of general formula:

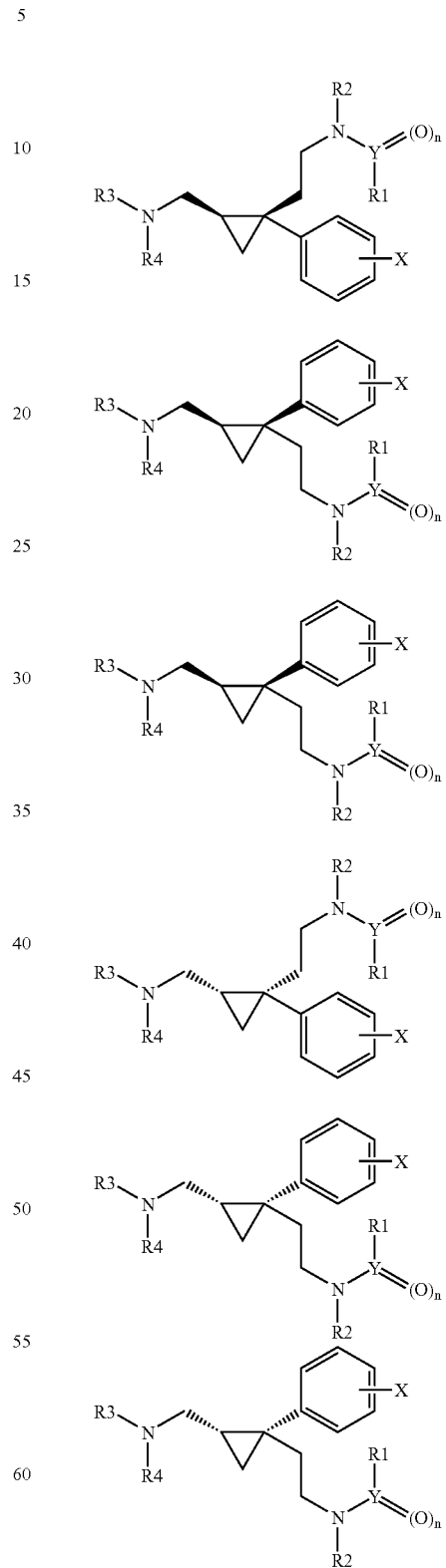

The compounds prepared according to the method of Preparation 29 were dissolved in 3 mL DCE (1:1) and further split out in combinatorial fashion such that each reaction was performed on a theoretical scale of 0.12 mmol in 1 mL DCE. Polymer-bound diisopropylamine (0.48 mmol, 4 eq) was added to each well followed by either an acid chloride or sulfonyl chloride (0.12 mol, 1 eq) in 1 mL DCE. The resultant reaction mixtures were agitated at ambient temperature for 16 h and excess acid or sulfonyl chloride scavenged by addition of polymer-bound trisamine (0.36 mmol, 3 eq) and agitation at ambient temperature for 4 h. The reaction plates were filtered and the filtrates concentrated to dryness. Crude products were dissolved in 300 microliters of DMSO and brought up to a final volume of 500 microliters using methanol. This 500 microliter solution was injected by a Waters 2767 autosampler into an XTerra C18 5 micron particle HPLC column (19 mm×150 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. Chiral HPLC was performed on representative samples to confirm that homochiral integrity had been preserved.

Scheme 4:

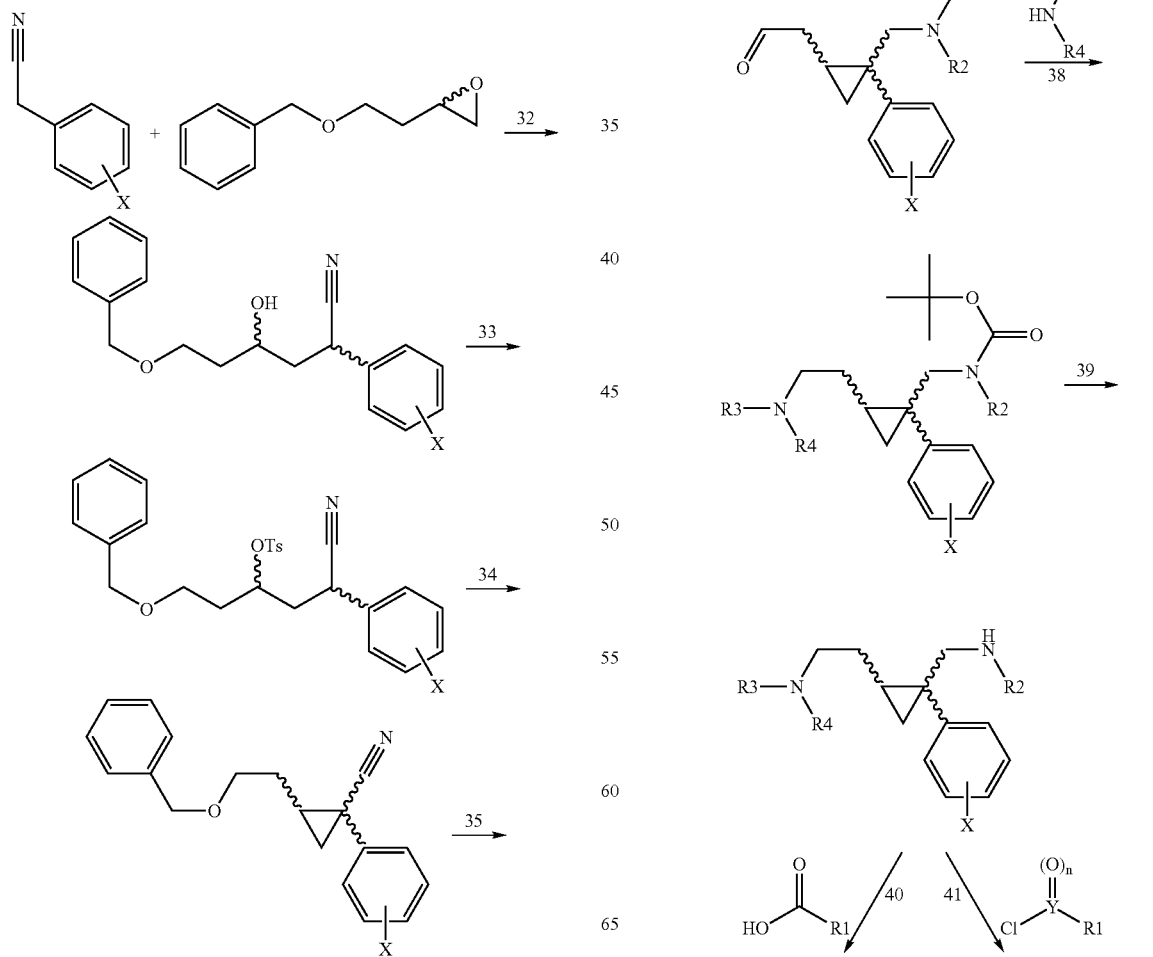

119

-continued

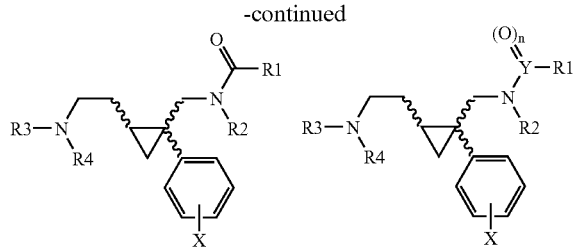

Where:

$\underset{Cl}{\overset{(O)_n}{\overset{\|}{Y}}}$—R1 = an acid chloride or a sulfonyl chloride R2—X = an alkyl halide Preparation 32: (4S)-2-(3-chlorophenyl)-4-hydroxy-6-[(phenylmethyl)oxy]hexanenitrile

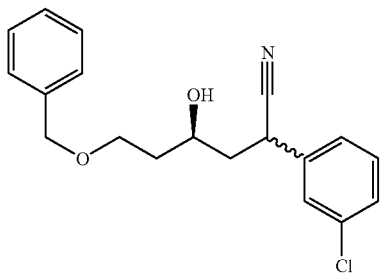

(3-Chlorophenyl)acetonitrile (8.62 mL, 72.9 mmol) in 100 ml of THF was cooled to −78° C. Butyllithium (35.1 mL, 56.1 mmol, 1.6 M in THF) was added over 20 minutes and stirred for an additional 15 min at −78° C. (2R)-2-{2-[(phenylmethyl)oxy]ethyl}oxirane (10.0 g, 56.1 mmol, *Synthesis* 1992, 7, 621-623) in 20 mL of THF was added over 30 minutes and stirred for an additional hour at −78° C. After warming to room temperature the solvent was evaporated and the orange red oil was chromatographed on silica gel with 20-25% EtOAc in Hexanes to give the title compound (11.05 g, 58%). 1H NMR (400 MHz, CHLOROFORM-D) δ ppm 1.8 (m, 3H) 3.6 (m, 1H) 3.7 (m, 2H) 4.1 (m, 2H) 4.5 (m, 2H) 7.3 (m, 9H).

Preparation 33: (1S)-3-(3-chlorophenyl)-3-cyano-1-{2-[(phenylmethyl)oxy]ethyl}propyl 4-methylbenzenesulfonate

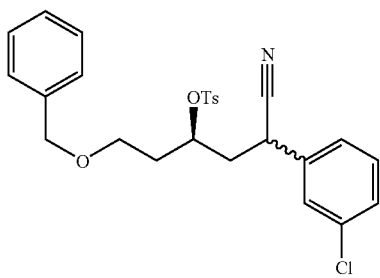

120

To a solution of (4S)-2-(3-chlorophenyl)-4-hydroxy-6-[(phenylmethyl)oxy]hexanenitrile (6.00 g, 18.2 mmol) in 50% CHCl$_3$ in pyridine at 0° C. was added DMAP (2.22 g) and toluenesulfonyl chloride (10.4 g, 54.5 mmol). After warming to room temperature over several hours, the reaction mixture was stored in the freezer for 2 days. After an aqueous work up with 1N HCl the organic layer was dried over MgSO$_4$ and evaporated to an oil. Chromatography on silica with 25% EtOAc in Hexanes afforded the title compound (5.68 g, 66%) as a yellow oil. 1H NMR (400 MHz, CHLOROFORM-D) δ ppm 1.9 (m, 2H) 2.1 (m, 2H) 2.3 (m, 2H) 2.4 (s, 3H) 3.4 (m, 1H) 3.5 (m, 1H) 4.4 (m, 2H) 7.1 (m, 1H) 7.3 (m, 10H) 7.8 (m, 2H)

Preparation 34: (1R,2R)-1-(3-chlorophenyl)-2-{2-[(phenylmethyl)oxy]ethyl}cyclopropanecarbonitrile

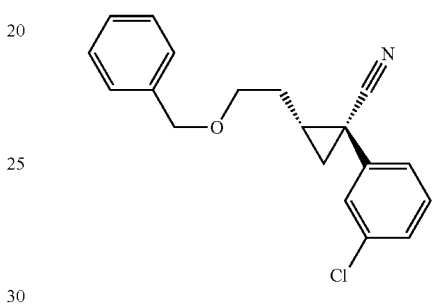

3.2 mL 1M LHMDS in hexanes (3.2 mmol) was added to 15 mL of DMF and cooled to −40° C. To this was added a solution of (1S)-3-(3-chlorophenyl)-3-cyano-1-(2-[(phenylmethyl)oxy]ethyl}propyl 4-methylbenzenesulfonate (1.00 g, 2.12 mmol) in 5 mL of DMF over 10 minutes and stirred for 40 minutes After warming to room temperature the reaction was stirred until no starting material remained by TLC. The reaction mixture was poured into 100 mL water, extracted with 50 mL EtOAc, the organic phase isolated, washed with brine and dried over MgSO$_4$. The resulting residue was purified by silica gel chromatography with 25% EtOAc in hexanes to give the title compound (436 mg, 65% yield). 1H NMR (400 MHz, CHLOROFORM-D) δ ppm 1.4 (dd, J=7.5, 5.6 Hz, 1H) 1.5 (m, 1H) 1.7 (m, 1H) 2.0 (m, 2H) 3.6 (m, 2H) 4.5 (d, J=2.2 Hz, 2H) 7.1 (m, 1H) 7.2 (m, 3H) 7.3 (m, 5H).

Preparation 35: [((1R,2R)-1-(3-chlorophenyl)-2-{2-[(phenylmethyl)oxy]ethyl}cyclopropyl)methyl] amine

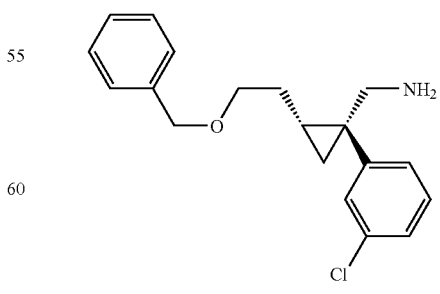

A solution of (1R,2R)-1-(3-chlorophenyl)-2-{2-[(phenylmethyl)oxy]ethyl}cyclopropanecarbonitrile (1.26 g, 4.0 mmol)

in diethyl ether at 0° C. was treated with 2 equivalents of LAH (1M in diethyl ether). After 1.5 hours at 0° C., water was added dropwise until no further evolution of gas was observed. The aluminum salts were filtered off and washed with diethyl ether. Evaporation of the diethyl ether afforded the title compound. 1H NMR (400 MHz, CHLOROFORM-D) δ ppm 0.5 (dd, J=5.9, 4.8 Hz, 1H) 1.0 (dd, J=8.9, 4.7 Hz, 1H) 1.2 (m, 1H) 1.4 (s, 2H) 1.8 (m, 2H) 2.9 (m, 2H) 3.6 (m, 2H) 4.6 (s, 2H) 7.2 (m, 3H) 7.3 (m, 2H) 7.4 (m, 4H).

Preparation 36: 1,1-dimethylethyl [((1R,2R)-1-(3-chlorophenyl)-2-(2-[(phenylmethyl)oxy]ethyl}cyclopropyl)methyl]methylcarbamate

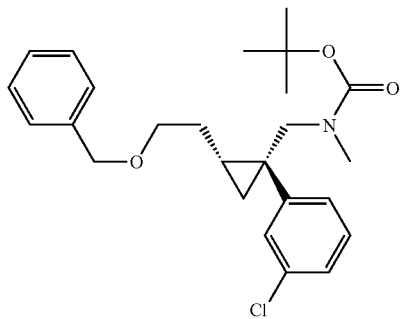

A solution of [((1R,2R)-1-(3-chlorophenyl)-2-{2-[(phenylmethyl)oxy]ethyl}cyclopropyl)methyl]amine (1.67 g, 5.29 mmol) and triethylamine (0.74 mL, 5.29 mmol) in DCM was cooled to 0° C. Di-tert-butyl dicarbonate (1.15 g, 5.29 mmol) was added as a solid and stirred at 0° C. for 1 hour. The reaction mixture was evaporated to give 2.27 g of an oil which was redissolved in THF and iodomethane (2.27 g, 15.98 mmol) and cooled to 0 C.°. NaHMDS (8.0 mL, 1M in THF) was added over 20 minutes to the stirring solution. After warming to room temperature the reaction was poured into water and diethyl ether. The diethyl ether was isolated, washed with water, dried over MgSO₄ and evaporated to afford the title compound (2.08 g, 91% yield). 1H NMR (400 MHz, CHLOROFORM-D) δ ppm 0.7 (m, 1H) 1.2 (m, 9H) 1.3 (m, 3H) 1.7 (m, 1H) 1.9 (m, 1H) 2.6 (s, 1H) 2.8 (s, 2H) 3.6 (m, 2H) 3.9 (d, J=14.8 Hz, 1H) 4.6 (s, 2H) 7.2 (m, 3H) 7.3 (m, 2H) 7.3 (m, 4H)

Preparation 37A: 1,1-dimethylethyl {[(1R,2R)-1-(3-chlorophenyl)-2-(2-oxoethyl)cyclopropyl]methyl}methylcarbamate

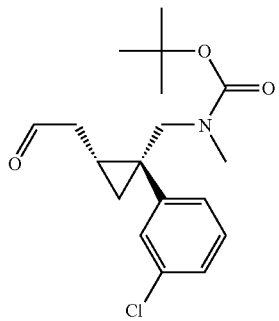

A solution of 1,1-dimethylethyl [((1R,2R)-1-(3-chlorophenyl)-2-{2-[(phenylmethyl)oxy]ethyl}cyclopropyl)methyl]methylcarbamate (2.08 g, 4.83 mmole) in 50 mL EtOAc was stirred overnight under 1 atmosphere of H₂ with 360 mg of 10% Pd on carbon. The suspension was filtered through celite and evaporated to afford 1.84 g of an oil. The oil was dissolved in DCM and added to a solution of Dess-Martin periodinane (3.67 g, 8.66 mmol) and 2-methyl-2-propanol (828 µl, 8.66 mmole) in DCM. After stirring overnight, the reaction mixture was mixed with 100 mL of 1N NaOH and 5.0 g of Na₂SO₄ for 20 minutes. 100 mL of diethyl ether was added and the organic layer washed with 1N NaOH, water and dried over MgSO₄. Removal of solvent afforded the title compound as a crude oil which was used without further purification. ES-LCMS m/z 360 (M+Na).

Preparation 37B: tert-butyl {[(1R,2S)-1-(3-chlorophenyl)-2-(2-oxoethyl)cyclopropyl]methyl}methylcarbamate

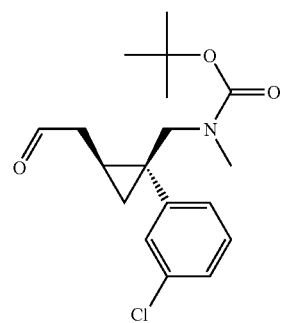

Starting from (3-chlorophenyl)acetonitrile and (2S)-2-{2-[(phenylmethyl)oxy]ethyl}oxirane and using the methods of Preparations 32, 33, 34, 35, 36, and 37A sequentially, the title product can be obtained in comparable yields and analytical characterization to those obtained in those preparations.

Preparation 38: Compounds of generic structure:

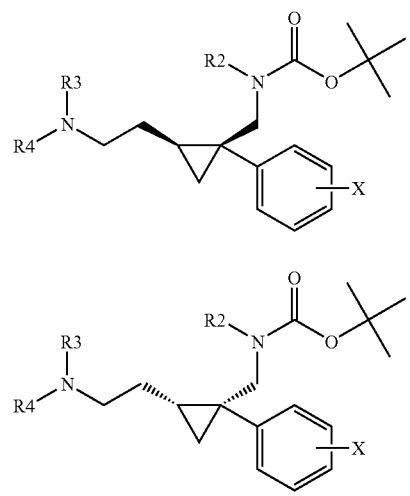

In combinatorial fashion, aldehydes prepared by the method of Preparations 37A-B (0.35 mmol) in 3 mL DCE were treated with various secondary amines (0.35 mmol, 1 eq) and mp-sodium triacetoxyborohydride (500 mg, 1.04 mmol, 3 eq) at ambient temperature for 20 h with continuous agitation. The reaction mixtures were each filtered. The remaining resin was treated with 4 mL DCM with agitation for 1 h and the organics separated via filtration. The organic filtrates were concentrated to dryness and carried forward without purification or characterization.

Preparation 39: Compounds of generic structure:

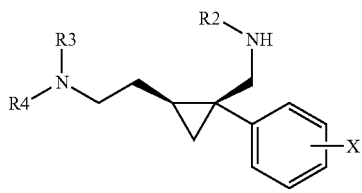

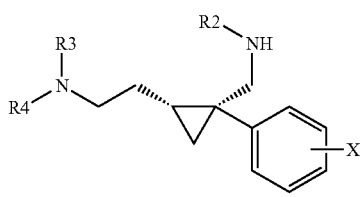

Compounds prepared by the method of Preparation 38 were treated with 1 mL trifluoroacetic acid in 2 mL DCM and 2 mL DCE for 5 h at ambient temperature with slight agitation. The reaction mixtures were concentrated and partitioned between DCM (2 mL) and saturated $NaHCO_3$ (2 mL) and the organic phases separated via filtration through hydrophobic frit tube assemblies. The organic filtrates were concentrated to dryness and carried forward without purification or characterization.

Preparation 40: Compounds of general formula:

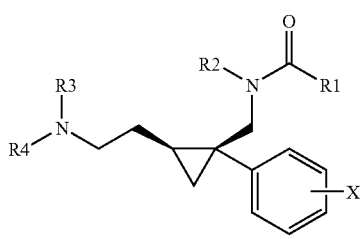

-continued

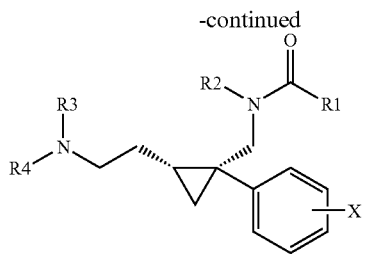

The compounds prepared according to the method of Preparation 39 were dissolved in 3 mL DCE and further split out in combinatorial fashion such that each reaction was performed on a theoretical scale of 0.12 mmol in 1 mL DCE. The reaction plates were concentrated down and the residues taken up in 1 mL DMF for reaction. Polymer-bound diisopropylamine (0.48 mmol, 4 eq) was added to each well followed by an acid (0.13 mmol, 1.1 eq) in 0.5 mL DMF and HATU (0.12 mmol, 1 eq) in 0.5 mL DMF. The resultant reaction mixtures were agitated at ambient temperature for 18 h and HATU byproducts scavenged by addition of polymer-bound carbonate (0.36 mmol, 3 eq) and agitation at ambient temperature for 3 h. The reaction plates were filtered and the filtrates concentrated to dryness. Crude products were dissolved in 300 microliters of DMSO and brought up to a final volume of 500 microliters using methanol. This 500 microliter solution was injected by a Waters 2767 autosampler into an XTerra C18 5 micron particle HPLC column (19 mm×150 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. Chiral HPLC was performed on representative samples to confirm that homochiral integrity had been preserved.

Preparation 41: Compounds of general formula:

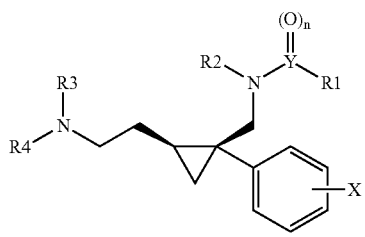

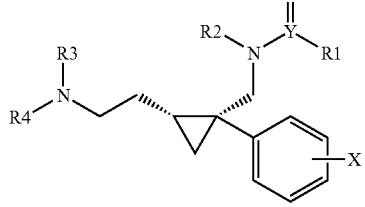

The compounds prepared according to the method of Preparation 39 were dissolved in 3 mL DCE (1:1) and further split out in combinatorial fashion such that each reaction was performed on a theoretical scale of 0.12 mmol in 1 mL DCE. Polymer-bound diisopropylamine (0.48 mmol, 4 eq) was added to each well followed by either an acid chloride or sulfonyl chloride (0.12 mol, 1 eq) in 1 mL DCE. The resultant reaction mixtures were agitated at ambient temperature for 16 h and excess acid or sulfonyl chloride scavenged by addition of polymer-bound trisamine (0.36 mmol, 3 eq) and agitation at ambient temperature for 4 h. The reaction plates were filtered and the filtrates concentrated to dryness. Crude products were dissolved in 300 microliters of DMSO and brought up to a final volume of 500 microliters using methanol. This 500 microliter solution was injected by a Waters 2767 autosampler into an XTerra C18 5 micron particle HPLC column (19 mm×150 mm). Initial solvent flow was 20 ml/min with 30% methanol and 70% water at a pH of 11 using ammonium hydroxide as buffer. Void volume was 2 minutes, and a linear gradient to 100% methanol in 10 minutes with a five minute wash at 100% methanol eluted the compound in approximately 10 minutes. A Micromass Platform LC mass spectrometer was used to monitor a split off the eluate for desired mass, and the purified fractions were collected using Micromass Fractionlynx software. Chiral HPLC was performed on representative samples to confirm that homochiral integrity had been preserved.

The following example demonstrates the above-referenced general scheme:

Example 12

N-[((1S,2S)-1-(3-chlorophenyl)-2-{2-[1-(3-methylphenyl)-4-oxo-1,3,8-triazaspiro[4.5]dec-8-yl]ethyl}cyclopropyl)methyl]-N-methylcyclopentanecarboxamide

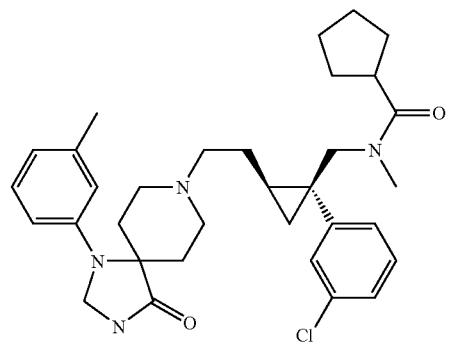

The title compound was prepared according to the methods of Preparation 41. ES-LCMS m/z 661.36 (M+H).

Scheme 5:

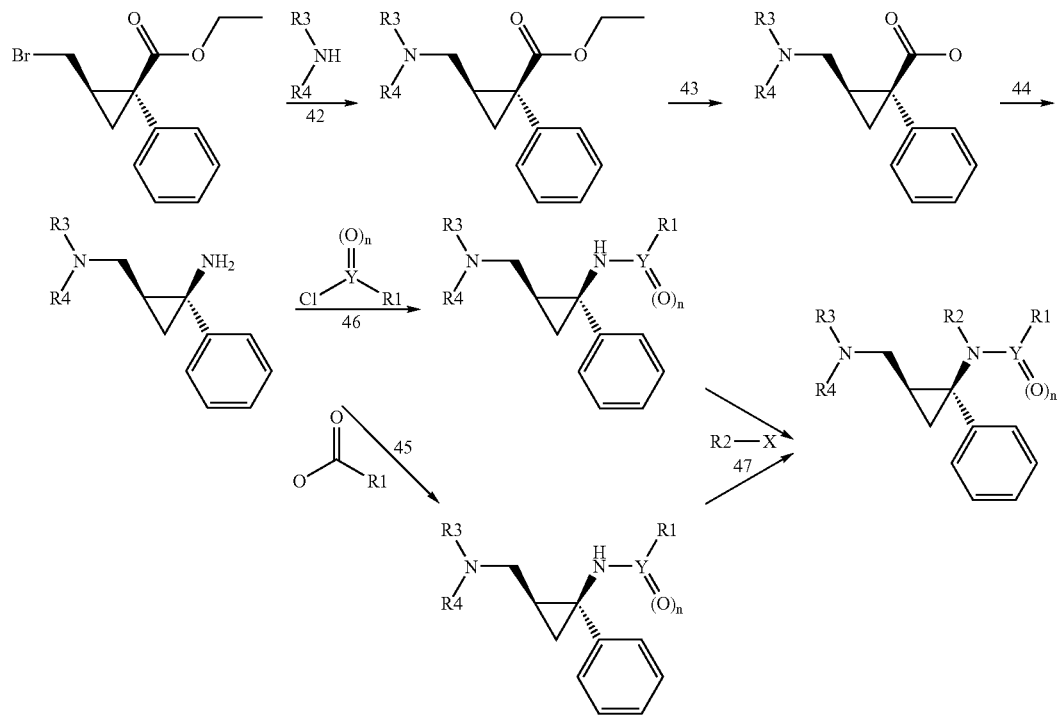

Where:

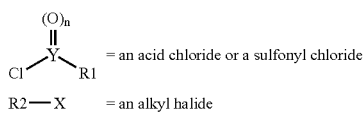

= an acid chloride or a sulfonyl chloride

R2—X = an alkyl halide

Preparation 42: Ethyl (1S,2R)-2-{[(3-endo)-3-(2-methyl-1H-benzimidazol-1-yl)-8-azabicyclo[3.2.1]oct-8-yl]methyl}-1-phenylcyclopropanecarboxylate

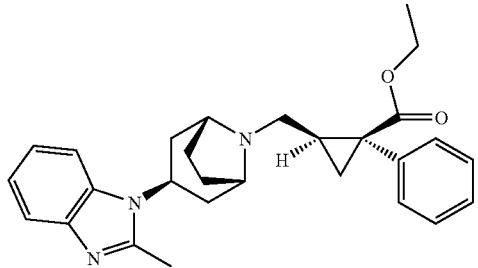

Ethyl (1S,2R)-2-(bromomethyl)-1-phenylcyclopropanecarboxylate (538 mg, 1.90 mmol, 1 eq., *J. Med. Chem.* 1987, 30(2), 318-325) was combined with 1-[(3-endo)-8-azabicyclo[3.2.1]oct-3-yl]-2-methyl-1H-benzimidazole (700 mg, 1.90 mmol, 1 eq., WO 00/38680), potassium carbonate (790 mg, 5.70 mmol, 3 eq.) and a catalytic amount of potassium iodide in 10 mL DMF and stirred 16 h at 85° C. The reaction mixture was partitioned between EtOAc and water (pH=9) and the organic phase isolated. The organic phase was combined with fresh water and the pH adjusted to 2 with 1N HCl. The aqueous phase was isolated, the pH adjusted to 11 with 1N NaOH, and extracted with DCM. The organic phase was isolated, dried over MgSO4, filtered and concentrated to give the title compound (574 mg, 1.29 mmol, 68%) as a brown foam. 1H NMR (400 MHz, DMSO-D6, 85° C.) δ ppm 1.2 (t, J=7.1 Hz, 3H) 1.4 (dd, J=9.0, 4.5 Hz, 1H) 1.6 (dd, J=7.1, 4.5 Hz, 1H) 1.8 (m, 3H) 1.9 (m, 2H) 2.1 (m, 2H) 2.4 (m, 2H) 2.5 (s, 3H) 2.7 (m, 1H) 3.4 (m, 1H) 3.7 (m, 1H) 4.1 (q, J=7.1 Hz, 2H) 4.8 (m, 1H) 7.1 (m, 2H) 7.2 (m, 1H) 7.3 (t, J=7.4 Hz, 2H) 7.4 (m, 2H) 7.4 (m, 1H) 7.5 (m, 1H). ES-LCMS m/z 444.24 (M+H).

Preparation 43: (1S,2R)-2{[(3-endo)-3-(2-methyl-1H-benzimidazol-1-yl)-8-azabicyclo[3.2.1]oct-8-yl]methyl}-1-phenylcyclopropanecarboxylic acid

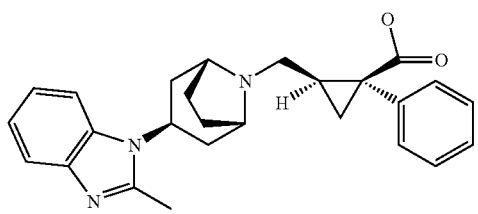

Ethyl (1S,2R)-2-{[(3-endo)-3-(2-methyl-1H-benzimidazol-1-yl)-8-azabicyclo[3.2.1]oct-8-yl]methyl}-1-phenylcyclopropanecarboxylate (574 mg, 1.29 mmol, 1 eq.) was dissolved in 1.9 mL ethyl alcohol and treated with 1.9 mL 1N LiOH (1.9 mmol, 1.5 eq.) 16 h at ambient temperature. The reaction mixture was concentrated to dryness, chased three times with toluene and pumped on under high vacuum to dryness. The crude product was triturated with DCM which was decanted off leaving the title compound (526 mg, 1.27 mmol, 99%) as a white solid residue. 1H NMR (400 MHz, DMSO-D6, 85° C.) δ ppm 1.3 (dd, J=8.9, 4.4 Hz, 1H) 1.5 (dd, J=7.0, 4.4 Hz, 1H) 1.7 (m, 3H) 1.9 (m, 2H) 2.2 (m, 2H) 2.5 (m, 2H) 2.5 (s, 3H) 2.7 (dd, J=12.8, 5.4 Hz, 1H) 3.4 (m, 1H) 3.7 (m, 1H) 4.9 (m, 1H) 7.1 (m, 2H) 7.2 (m, 1H) 7.3 (m, 2H) 7.4 (m, 2H) 7.4 (m, 1H) 7.5 (m, 1H). ES-LCMS m/z 416.19 (M+H).

Preparation 44: ((1S,2S)₂-{[(3-endo)-3-(2-methyl-1H-benzimidazol-1-yl)-8-azabicyclo[3.2.1]oct-8-yl]methyl}-1-phenylcyclopropyl)amine

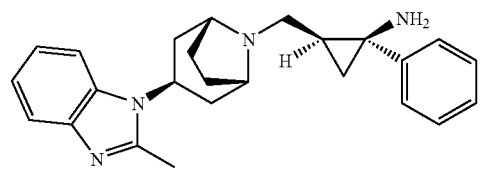

(1S,2R)-2-{[(3-endo)-3-(2-methyl-1H-benzimidazol-1-yl)-8-azabicyclo[3.2.1]oct-8-yl]methyl}-1-phenylcyclopropanecarboxylic acid (174 mg, 0.42 mmol, 1 eq.) was treated with 10 mL thionyl chloride for 16 h at ambient temperature. The reaction mixture was concentrated to dryness, chased two times with toluene and pumped dry to give the acid chloride as a yellow foam. The acid chloride thus obtained was suspended in 5 mL acetone and treated with sodium azide (73 mg, 1.12 mmol, 2.7 eq.) dissolved in 2 mL water at ambient temperature. The reaction mixture was stirred 1 h at ambient temperature and then diluted with saturated NaHCO₃ and extracted with toluene. The toluene layer was isolated, dried over MgSO₄, filtered, and the filtrate heated at 90° C. for 2 h. After cooling, water was added to the reaction mixture and the pH adjusted to 2 with 1N HCl. The aqueous phase was isolated, the pH adjusted to 10 with 1N NaOH, extracted two times EtOAc, the organic phases combined, dried over MgSO₄, filtered and concentrated to give the title compound (61 mg, 0.16 mmol, 38%) as a yellow film. 1H NMR (400 MHz, DMSO-D6, 85° C.) δ ppm 0.7 (m, 1H) 1.2 (m, 2H) 1.7 (m, J=7.6 Hz, 2H) 1.9 (m, 2H) 2.2 (m, 2H) 2.4 (m, J=8.6 Hz, 2H) 2.5 (m, 3H) 2.6 (m, 2H) 3.5 (m, 1H) 3.6 (m, 1H) 4.7 (m, 1H) 7.1 (m, 3H) 7.3 (t, J=7.8 Hz, 2H) 7.4 (m, 2H) 7.4 (d, J=7.4 Hz, 1H) 7.5 (d, J=8.3 Hz, 1H). ES-LCMS m/z 387.28 (M+H).

Preparation 46, Example 13: N-((1S,2S)-2-{[(3-endo)-3-(2-methyl-1H-benzimidazol-1-yl)-8-azabicyclo[3.2.1]oct-8-yl]methyl}-1-phenylcyclopropyl)benzenesulfonamide

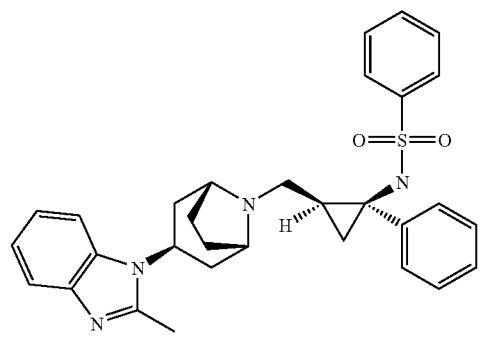

((1S,2S)-2-([[(3-endo)-3-(2-methyl-1H-benzimidazol-1-yl)-8-azabicyclo[3.2.1]oct-8-yl]methyl}-1-phenylcyclopropyl)amine (40 mg, 0.103 mmol, 1 eq.) was dissolved in 2 mL DCM/DCE (1:1) and treated with benzenesulfonyl chloride (40 uL, 0.310 mmol, 3 eq.) in the presence of PS-DIEA (40 mg, 0.155 mmol, 1.5 eq) at ambient temperature for 3 h. The resin was filtered off and the filtrate concentrated to dryness. The crude product was purified by HPLC on a C-18 column eluted with 0→100% $CH_3CN$ in water buffered with 0.1% TEA. The appropriate fraction was isolated and concentrated to give the title compound (20 mg, 0.038 mmol, 37%) as a white solid. 1H NMR (400 MHz, DMSO-D6, 85° C.) δ ppm 1.2 (m, 2H) 1.5 (m, 1H) 1.7 (m, 2H) 1.9 (m, 2H) 2.0 (m, 2H) 2.2 (dd, J=12.9, 6.5 Hz, 1H) 2.4 (m, 2H) 2.5 (s, 3H) 2.6 (dd, J=12.5, 5.0 Hz, 1H) 3.4 (m, 1H) 3.5 (m, 1H) 4.7 (m, 1H) 7.1 (m, 5H) 7.2 (m, 2H) 7.4 (m, 3H) 7.5 (m, 2H) 7.6 (m, 2H) 8.4 (s, 1H). ES-LCMS m/z 527.27 (M+H).

Example 14

N-((1R,2R)-2-{[(3-endo)-3-(2-methyl-1H-benzimidazol-1-yl)-8-azabicyclo[3.2.1]oct-8-yl]methyl}-1-phenylcyclopropyl)benzenesulfonamide

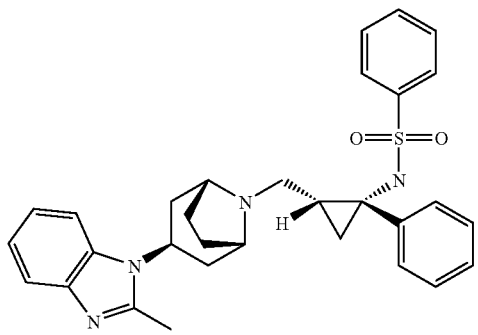

Starting from ethyl (1R,2S)-2-(bromomethyl)-1-phenylcyclopropanecarboxylate (J. Med. Chem. 1987, 30(2), 318-325) and using the methods of Preparations 42, 43, 44 and 46 sequentially, the title product can be obtained in comparable yields and analytical characterization to those obtained in those preparations.

List of abbreviations:

| List of abbreviations: |
|---|
| LAH = lithium aluminum hydride |
| DCE = dichloroethane |
| TFA = trifluoroacetic acid |
| LDA = lithium diisopropylamide |
| TEA = triethylamine |
| THF = tetrahydrofuran |
| DCM = dichloromethane |
| TLC = thin layer chromatography |
| LHMDS = lithium bis(trimethylsilyl)amide |
| NaHMDS = sodium bis(trimethylsilyl)amide |
| PS-DIEA = polystyrene supported diisopropylethylamine |
| PS-Trisamine = polystyrene supported trisamine |
| HATU = O-(7-azabenzotriazol-1-yl)-N,N,N',N'-tetramethyluronium hexafluorophosphate |
| DMF = N,N-Dimethylformamide |
| DMSO = Dimethyl sulfoxide |
| DIEA = N,N-Diisopropylethylamine |

| List of abbreviations: |
|---|
| THF = Tetrahydrofuran |
| $NaBH(OAc)_3$ = sodium triacetoxyborohydride |
| EtOAc = ethyl acetate |
| DMAP = dimethylaminopyridine |
| h = hours |
| HPLC = high performance liquid chromatography |
| $SiO_2$ = silica gel |

As will be appreciated by those skilled in the art, additional compounds of the present invention may be similarly prepared according to the schemes provided herein.

Biological Data

The following definitions apply:

| | |
|---|---|
| $IC_{50}$ | Concentration of compound that displaces 50% of radioligand |
| $pIC_{50}$ | The determined $IC_{50}$ value expressed as $-log10(IC_{50})$ |

CC-Chemokine Receptor-5 Binding by Scintillation Proximity Assay (CCR5 SPA) Scintillation Proximity Assay for the Human CC-Chemokine Receptor, CCR-5

This protocol describes a high-throughput screen using SPA binding to identify compounds that inhibit binding of $^{125}$I-MIP1α to the human CCR5 chemokine receptor.

CCR5 is a G protein-coupled receptor that binds the natural chemokine ligands, MIP1α, MIP1β and RANTES. CCR5 acts as a co-receptor with CD4 for entry of HIV-1 into human T-cells and monocytes. Chemokines also play a role in acute and chronic inflammatory processes. Chemokines are soluble proteins produced and released by a wide variety of cell types during the initial phase of a host response to a forgein substance entering the body.

Human CCR5 receptors were expressed in Chinese Hamster Ovary (CHO) cells, registration # 12025. Cells were grown in suspension and a 50 to 80 ml CCR5 cell pellet was prepared. Membrane preparation: 1) Weigh pellet; 2) Prepare an ice-cold 50 mM HEPES buffer, containing 0.0025 mg/ml Pefabloc, 0.0001 mg/ml Pepstatin A, 0.0001 mg/ml Leupeptin, 0.0001 mg/ml Aprotinin (protease inhibitor cocktail), pH 7.4; 3) Homogenize pellet in 5 volumes of HEPES buffer; 4) Homogenize again with a glass homogenizer 10 to 20 strokes; 5) Centrifuge homogenate at 18,000 rpm in a F28/36 rotor using a Sorvall RC26 PIUS refrigerated Centrifuge for 30 minutes; 6) Discard supernatant and resuspend pellet in 3 volumes of HEPES buffer; 7) Homogenize and centrifuge again using steps 4-6, 2 more times; 8) Reweigh pellet and homogenize in 3x weight-to-volume of HEPES buffer; 9) Aliquot 0.5 to 1.5 ml of the membrane preparation into small vials and store at −80 degrees Centigrade; 10) Determine the protein concentration of the membrane preparation using the Bio-Rad or BCA method; 11) The membrane homogenate will need to be characterized for the assay conditions a.) Protein concentration; b.) Optimal protein-to-bead ratio in SPA; and c.) Saturation curve to determine Kd and Bmax in SPA The saturation curve binding experiment is performed by adding varying amounts of [$^{125}$I]MIP1α (0-8.5 nM to membranes and beads in concentrations chosen from the optimal protein/bead ratio. The data is analyzed using a non-linear curve-fitting program. The $K_d$ and Bmax are derived from the curve.

Bacitracin 50 mg/ml is dissolved in deionized water, brought to a boil for 5 minutes (to destroy protease activity) and cooled. Prepared 1 ml aliquots and store at −80° C.

Protease inhibitor cocktail is prepared by dissolving 25 mg/ml of Pefabloc, 1 mg/ml of Leupeptin, 1 mg/ml of Aprotinin and 1 mg/ml of Pepstatin A in 100% DMSO. The cocktail can be aliquoted and stored frozen at −20° C. until needed.

Sigmacote: Any reagent bottles and reservoirs that come in contact with the radioligand are treated with Sigmacote to reduce sticking. Rinse containers with undiluted Sigmacote; rinse with deionized water several times, and allow to air dry before using.

Color Quench Assay-[$^{125}$I] SPA PVT color quench kit, Cat. No. RPAQ 4030, Amersham Ltd. A color quench curve is generated for each Packard TopCount and is stored in each counting protocol specific for the assay. This is done to prevent colored compounds from quenching the scintillation counts.

Compounds Preparation:

Compounds for a single concentration determination (One Shots) are delivered in 96 well Packard Optiplates containing 1 µl of compound in 100% DMSO in columns A1-H10 (80 compounds/plate). Column A11 to H11 is used for total binding (Bo) (vehicle-5 µl of the appropriate DMSO concentration) and column A12 to D12 is used for determination of nonspecific binding. No further preparation is required.

Compounds for concentration-response curves (10 points) are delivered in 96-Packard Optiplates containing 1 µl of compound in 100% DMSO in columns A1-H10. A 10-point concentration-response curve is desired for each compound with a starting high concentration of 30 µM (in the assauy final). Column A11 to $H_{11}$ is used for total binding (Bo) (vehicle-5 µl of the appropriate DMSO concentration) and column A12 to D12 is used for determination of nonspecific binding. No further preparation is required Materials:
1 M HEPES, pH 7.4, Gibco, Cat. No. 15360-080
Bacitracin, Sigma Catalog. Number. B-0125
Bovine Serum Albumin, Sigma, Cat. No. A-7888
$MgCl_2$, J. T. Baker 2444-01
$CaCl_2$, Sigma, Cat. No. C5080
MIP1α, Peprotech, Cat. No. 300-08
Sigmacote, Sigma, Cat. No. SL2
Scintillation Proximity Beads, Wheat Germ Agglutinin, Amersham, Cat No. RPNQ 0001
[$^{125}$I]MIP1α, NEN (#NEX298)
Packard 96 well flat-bottom Optiplate, Cat. No. 6005190
Falcon 96 well round-bottom plate, Cat. No. 3077
TOPSEAL-S, Packard, Cat. No. 6005161
Dimethyl Sulfoxide, EM Science, Cat. No. MX1458-6
Siliconized Pipette tips, Accutip, volume 200-1300 uL, Cat. No. P5048-85
Siliconized Pipette Ups, Blo Plas, Inc., volume 1-200 uL, Cat. No. 60828-908
Reagent Reservoir, Elkay, Cat. No. 175-RBAS-000

Assay Buffer Preparation:

50 mM HEPES buffer pH 7.4, 1 mM $CaCl_2$, 5 mM MgCl2 (this can be made ahead as a 100× stock), 1% BSA, 0.5 mg/ml Bacitracin, Protease inhibitor Cocktail (see preparation above) 100 uL/100 ml, DMSO is added to equal a final concentration of 2% per well (includes compound % DMSO) if needed.

Experimental Details:

[$^{125}$I]MIP1α Preparation:
Prepared radioligand dilutions in container treated with Sigmacote
Reconstitute each 50 µCi vial with 0.5 ml of deionized water and store at 4° C.
Specific Activity=2,000 Ci/mmol
Add ~60,000 cpm (0.17 nM) to each assay well in 50 uL Bo:
Make a 20% DMSO solution and add 5 uls of this to each well in col A11-H11. This gives a final 2% DMSO concentration for the well when added to the 1% in the assay buffer.

NSB:
Make a stock dilution of MIP1α at 100 uM using deionized water; aliquot and freeze. Dilute the MIP-1α stock solution to a concentration of 2 µM in the same 20% DMSO solution used above and add 5 µl to the wells in column A12 to D12 to give a final assay concentration of 100 nM. Prepare this in a Sigmacote-treated container Membrane and SPA Bead Preparation—

The final assay concentration for the membrane is 15 µg per well. SPA beads are prepared by adding 5 ml of assay buffer to a 500 mg vial. The final concentration of SPA beads in the assay is 0.25 mg/well. Membranes and beads are premixed as a 1:1 (membrane:bead) mixture and maintained at mixture at 4° C. with constant stirring. 50 µl of the mixture is added to each assay well. After all reagents have been added to the plates (total assay volume 100 µl), shake plates for 4 hours at room temperature. After 4 hours, place the plates on the TopCount in a count the plates on the TopCount for 30 sec per well using an appropriate program (i.e., one with a quench curve established for the conditions of the assay.

Data Reduction:

Data reduction is performed using the Microsoft Excel Addins Robofit or Robosage.

For single concentration assays (One Shots), the result of each test well is expressed as % inhibition using the following formula: $100*(1-(U1-C2)/(C1-C2))$. Where U1 is the unknown sample in cpm observed in a particular well, C1 is the average of column 12 cpm observed in the absence of any added inhibitor, and C2 is the average of column 11 cpm observed in the presence of 1 µM of MIP1α.

For concentration-response assays, the result of each test well is expressed as % B/Bo (% total specific binding) using the following formula: $100*(U1-C2)/C1-C2)$. Curves were generated by plotting the % B/Bo versus the concentration and the $IC_{50}$ is derived using the equation $y=Vmax*(1-(x\hat{\ }n/(k\hat{\ }n+x\hat{\ }n)))$.

Controls and Standards:

Each plate contains 12 wells of total binding (column A11-H11). The cpm/well are averaged and are used in data reduction as value C1. Each plate also contains 4 wells of nonspecific binding (wells A12-D12). The counts of these wells are averaged and used in data reduction as value C2.

A standards plate is included in each experiment. This plate contains a 14-point concentration-response curve (in triplicate) for the standard compound MIP1α at a starting concentration of 1 µM. The average historical $pK_i$ obtained with MIP1α is 7.6.

The relevant biological response field for a single concentration (One Shots) is % inhibition. Inhibition values of >40 or >50% were considered positive responses.

HOS Assay (Also Referred to as HOS-LTR-Luciferase Assay)

Materials
DMEM (GibcoBRL # 10564-011)
Trpsin-EDTA (GibcoBRL #25300-054)
Heat inactivated Fetal Bovine Serum (FBS) (Hyclone # SH30070.03)
96-well, black-walled, clear-bottom, tissue culture-treated plates (Costar # 3904)
96-well, clear-walled, clear-bottom tissue culture-treated plates (Costar # 3598)
Phosphate Buffered Saline (PBS) (GibcoBRL #14190-144)
Dimethyl Sulfoxide (DMSO) (Sigma # D2650)
Luclite Luciferase Reporter assay (Packard #6016911)
HOS-CD4.CCR5-LTR-Luciferase (Bioresource Registration # 21164): Human Osteosarcoma cell line engineered to overexpress human CD4 and human CCR5 (AIDS Repository cat# 3318) stably transfected with HIV-1-LTR-Luciferase reporter.

Advanced Preparation
Growth and Maintenance of the HOS-CD4.CCR5-LTR-Luciferase Cell Line:
The cells were propagated in DMEM containing 2% FBS. Cells were split by standard trypsinization when confluency reached 80% (roughly every 2 to 3 days).

Titering of Virus Stocks:
HIV-1 virus stocks were titered in the assay system in order to obtain an estimate of the number of infectious particles per unit volume (described as RLU/ml). Virus stocks were diluted into DMEM containing 2% FBS and assayed as described in the "procedure" section below.

Procedure
Black-walled 96-well tissue culture plates were seeded with HOS-CD4.CCR5-LTR-Luciferase @ 0.6 to $1.2 \times 10^3$ cells per well in 50 ul DMEM containing 2% FBS and placed in a humidified incubator @ 37° C., 5% $CO_2$ overnight. The following day, test compounds were titrated 4-fold at 2× the final concentration in DMEM+2% FBS+0.2% DMSO. 50 µl of titrated compound was transferred to the HOS cells and the plates were placed in a humidified incubator at 37° C., 5% $CO_2$ for 1 hr. An additional 60 ul of 2× titrated compound was transferred to a clear-walled 96-well tissue culture plate and 60 ul of HIV (diluted to appropriate m.o.i.) was added to each well and thoroughly mixed. 100 ul of the HIV/compound mixture was transferred to the black-walled plates containing 100 ul of cells/compound. The plates were placed in a humidified incubator at 37° C., 5% $CO_2$ for 72 hr. Following the 72 hour incubation, 150 ul of supernatant was removed and 50 ul of reconstituted LUCLITE (kit reagent) was added to each well. Each plate was sealed and read in a Topcount (Packard) luminometer at 1 s/well.

Data Reduction
Relative Light Units (RLU) were expressed as % control
(RLU at drug [ ]/RLU no drug)*100=% Control
$IC_{50}$ values were determined by any one of the following four nonlinear regression models:
y=Vmax*(1−(x^n/(K^n+x^n)))+Y2
y=Vmax*(1−(x^n/(K^n+x^n)))
y=Vmax*(1−(x/(K+x)))+Y2
y=Vmax*(1−(x/(K+x)))

Where: K is $IC_{50}$, Y2 is baseline, and N is Hill Coefficient
Each of the compounds of the present invention provides a $pIC_{50}$ value of at least 5 when tested in each of the above-described assays.

Test compounds are employed in free or salt form.
All research complied with the principles of laboratory animal care (NIH publication No. 85-23, revised 1985) and pharmaceutical industry policy on animal use.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:
1. A compound selected from the group consisting of

135
-continued
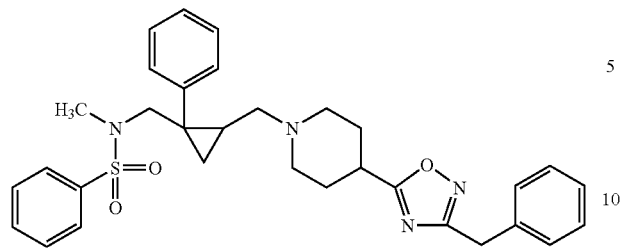
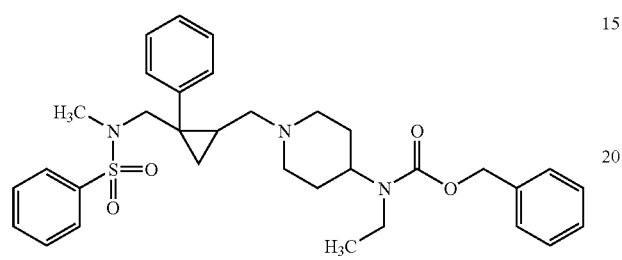
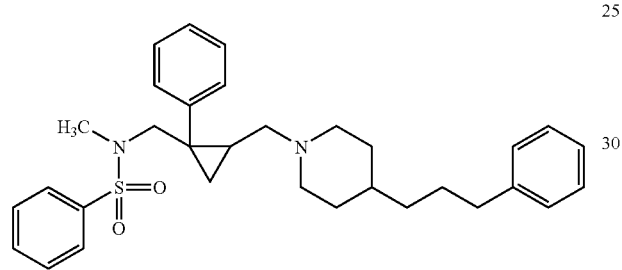
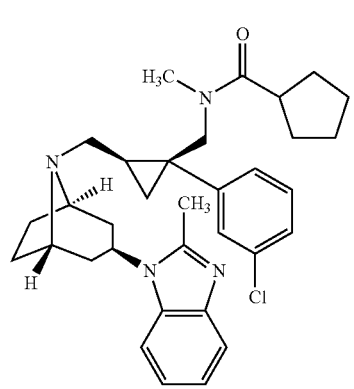
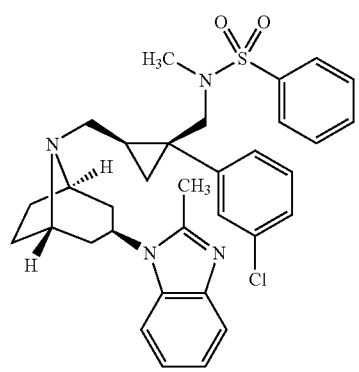
136
-continued
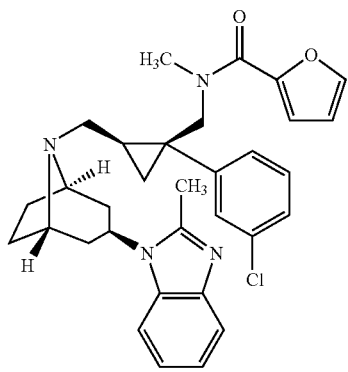
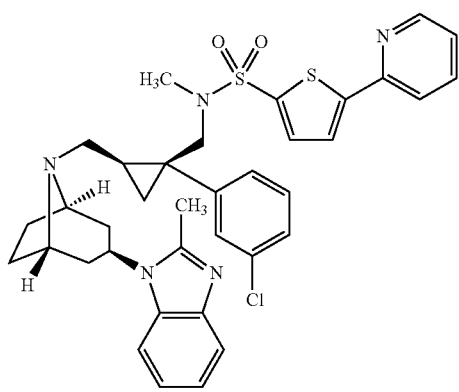
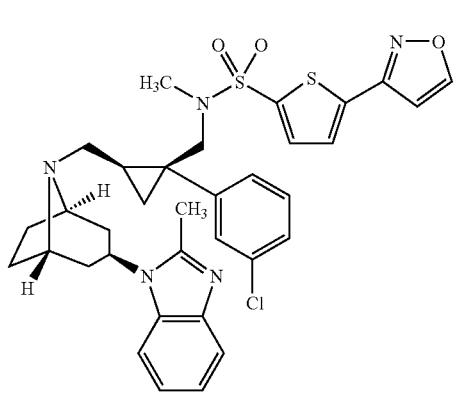
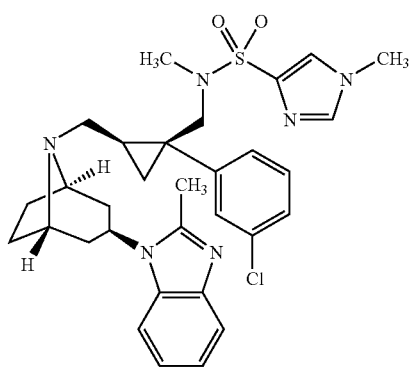

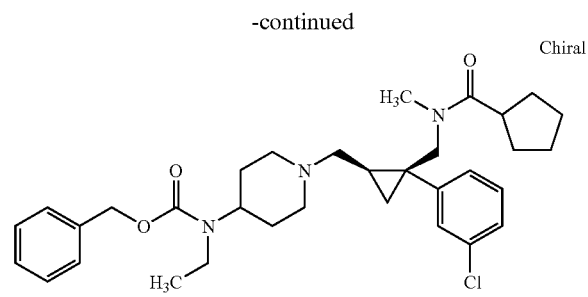
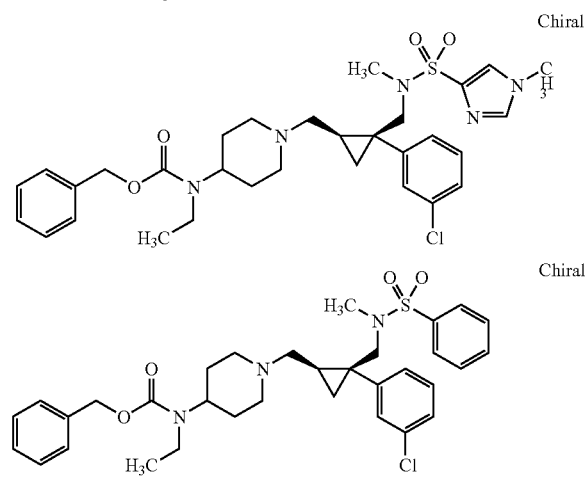
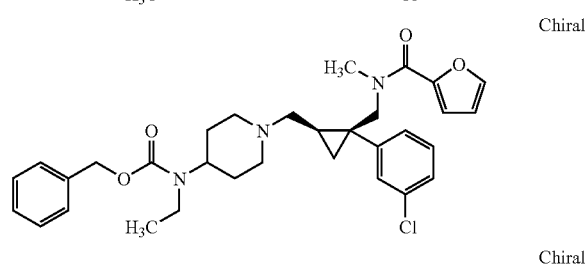
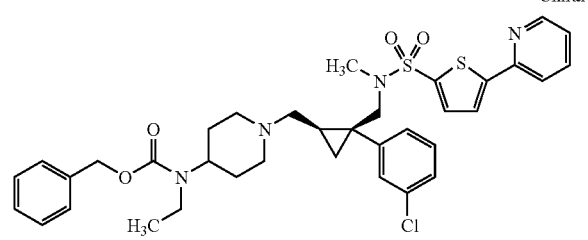
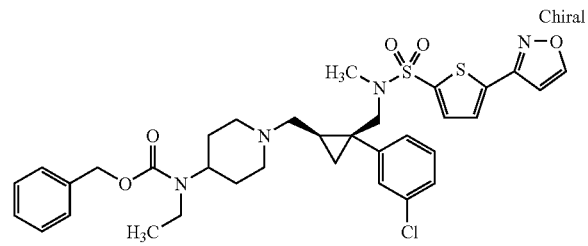
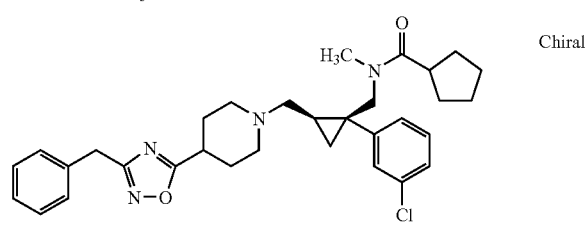
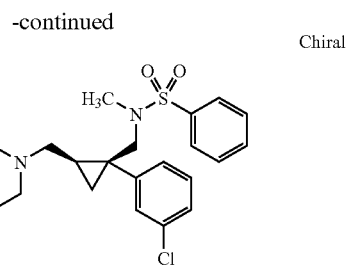
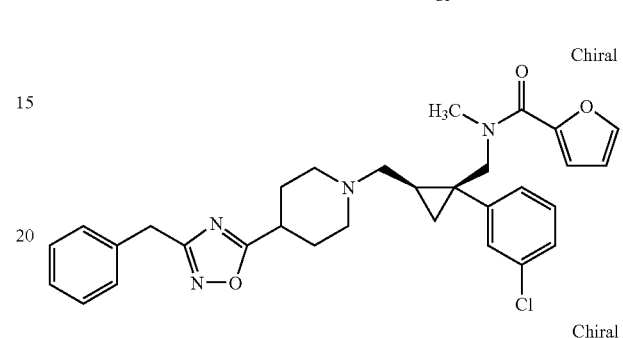
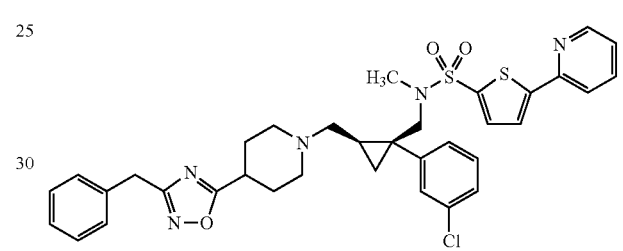
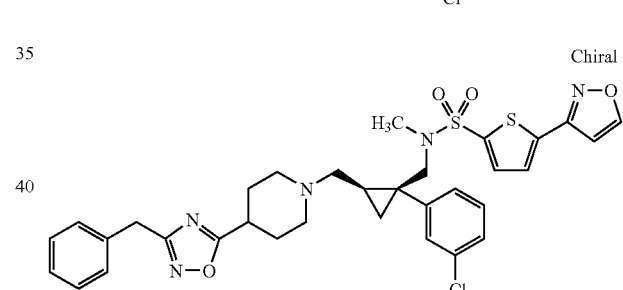
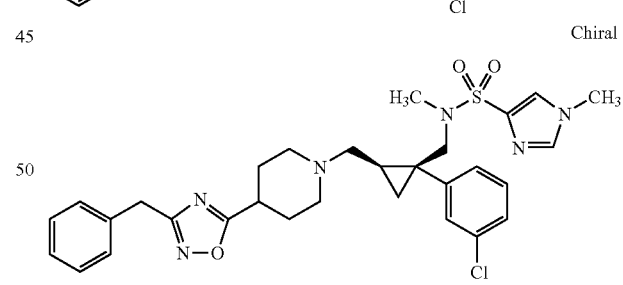
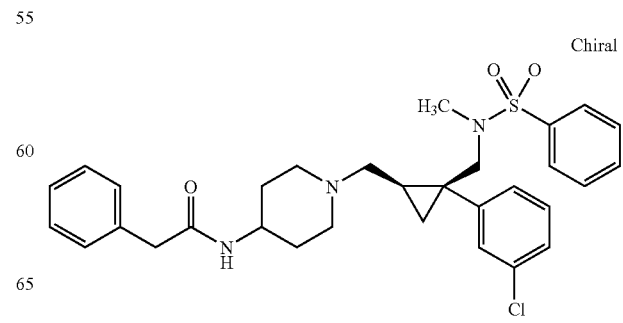

-continued
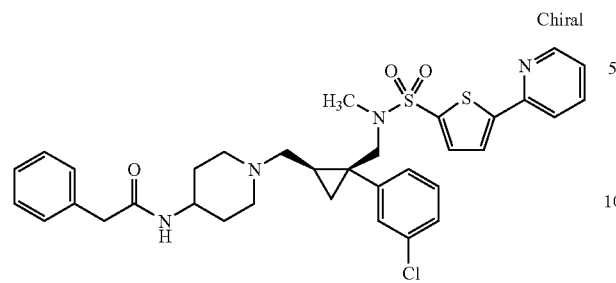
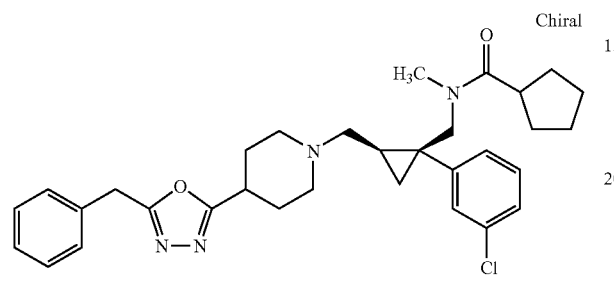
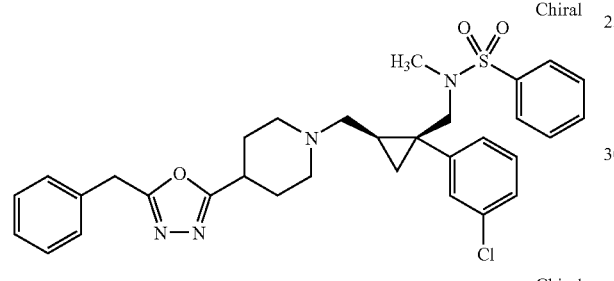
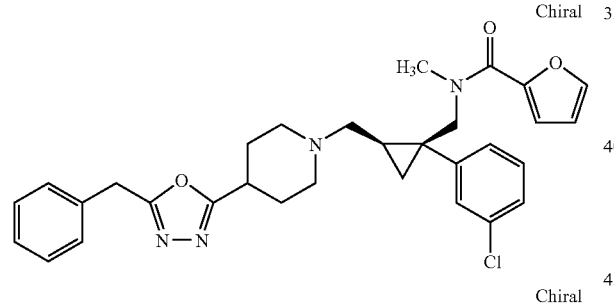
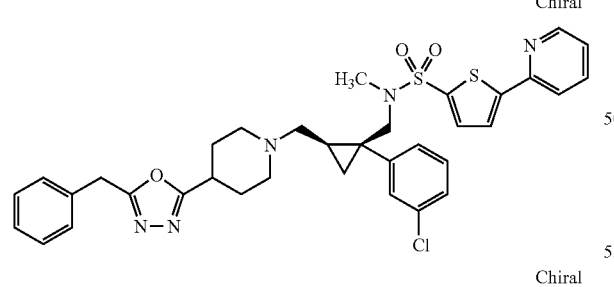
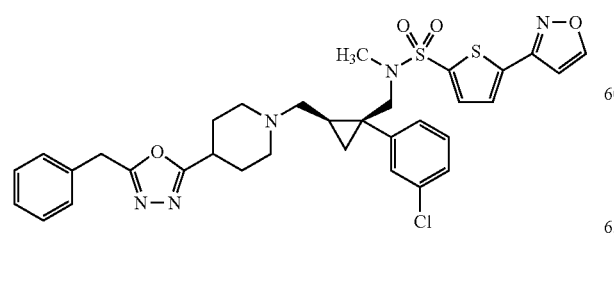
-continued
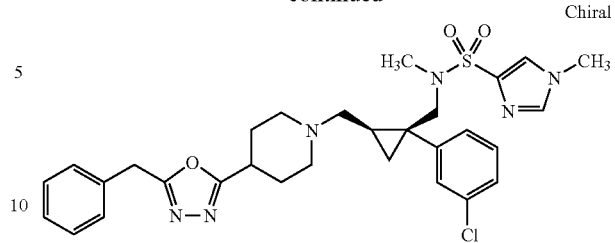
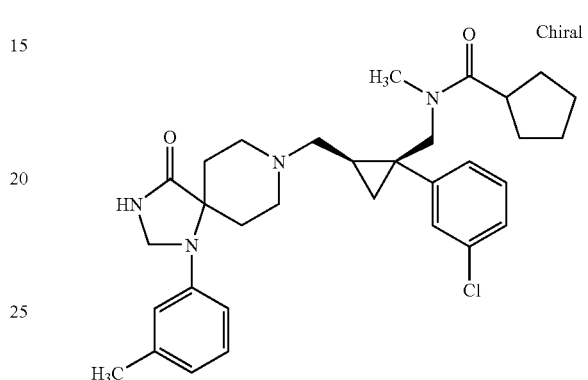
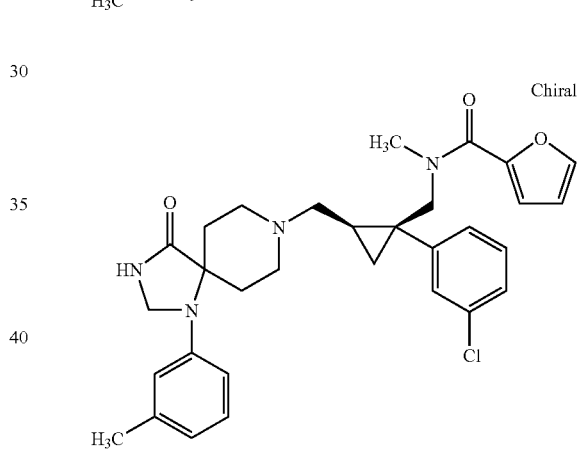
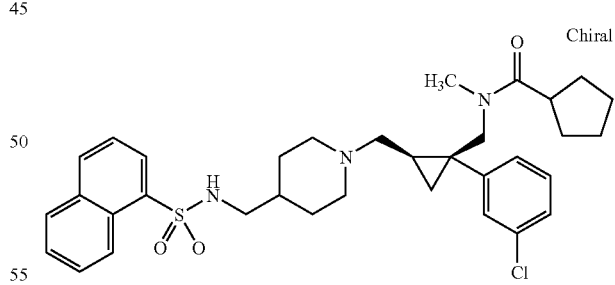
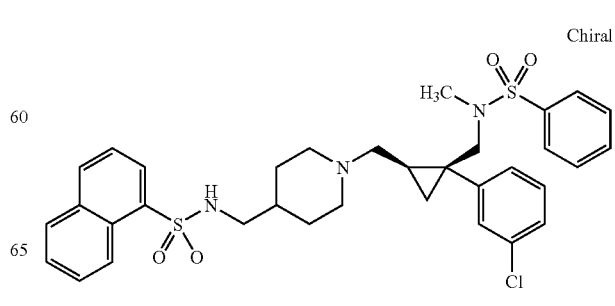

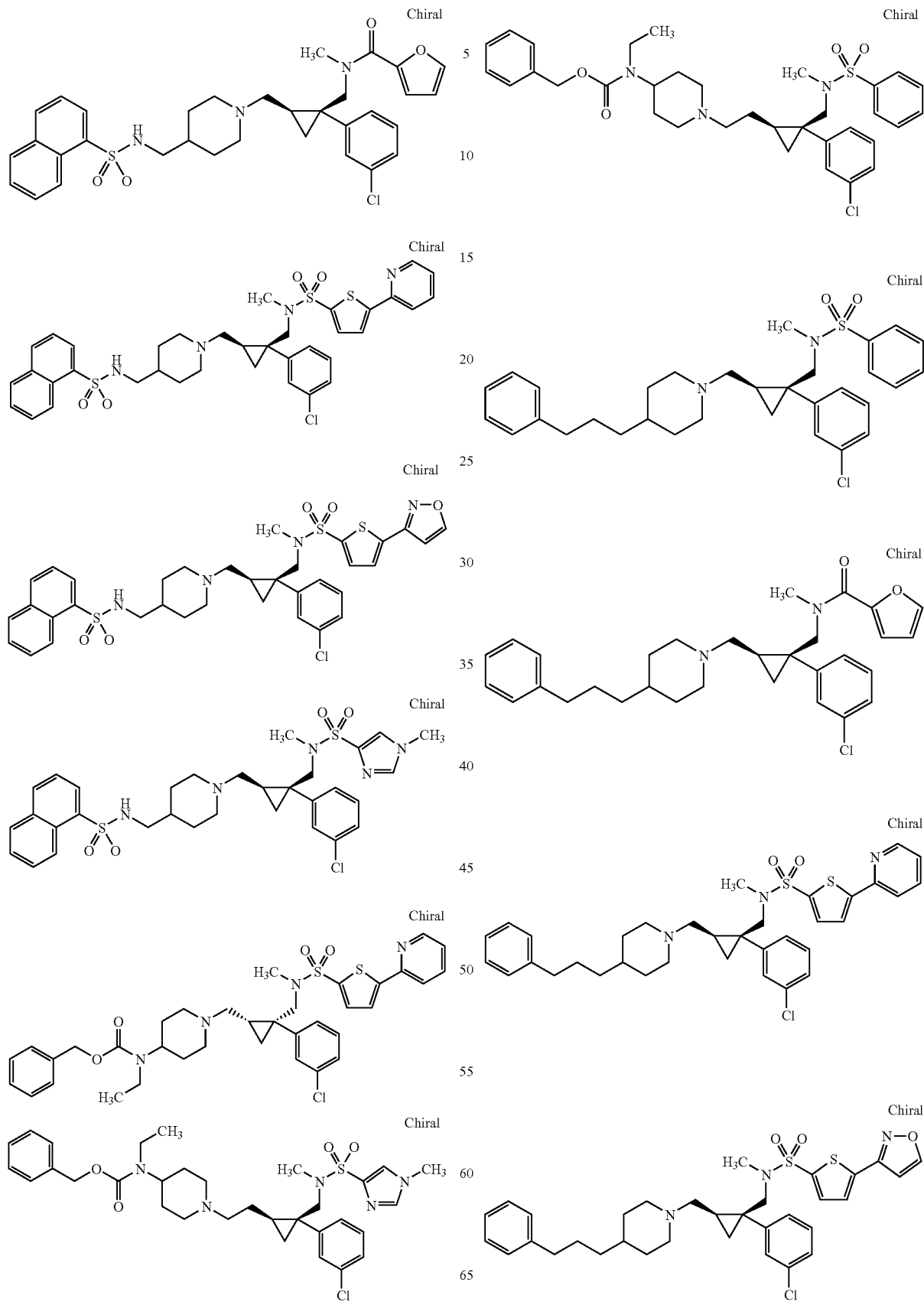

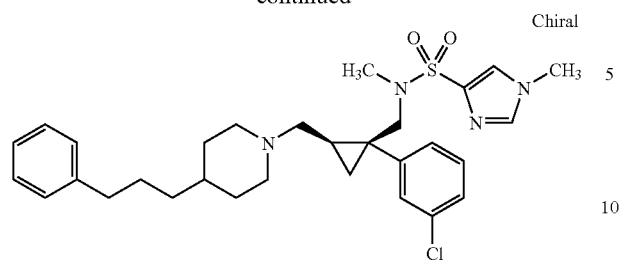
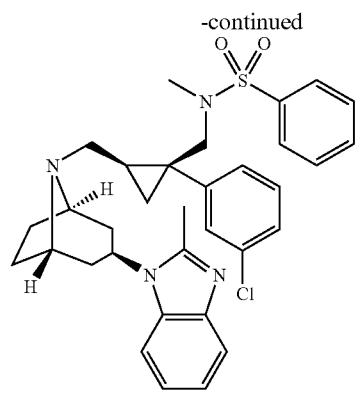
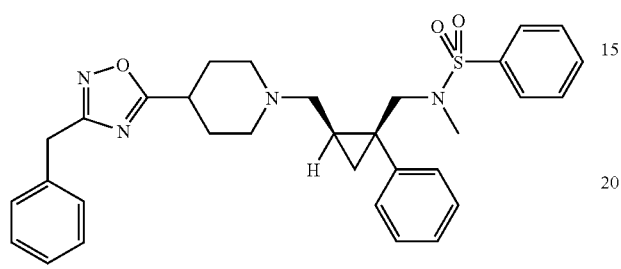
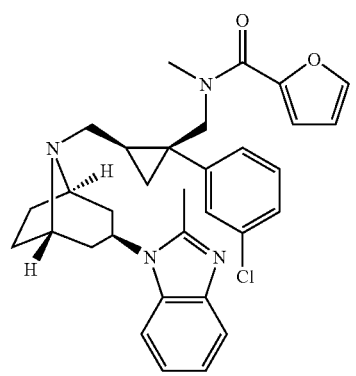
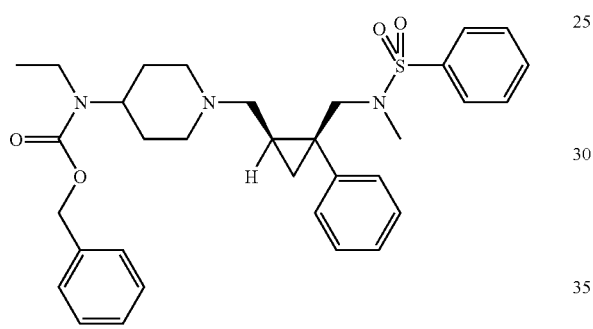
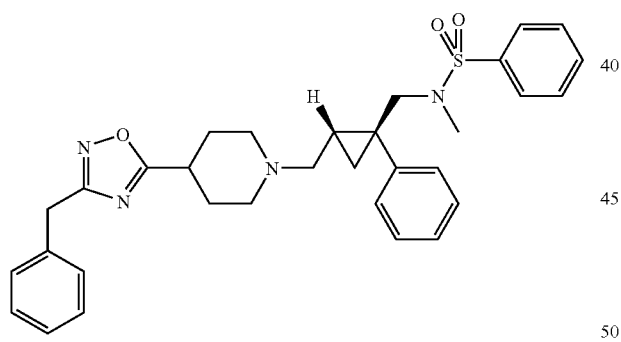
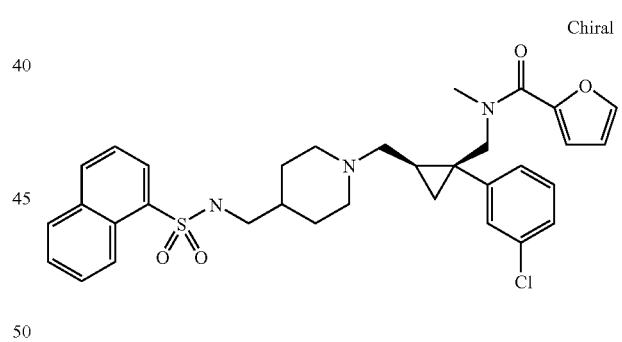
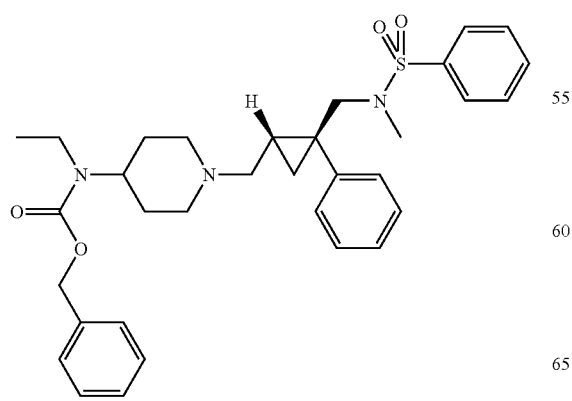
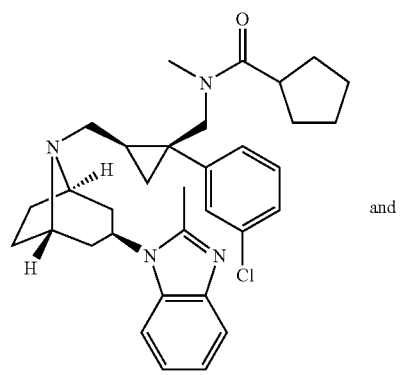
and -continued
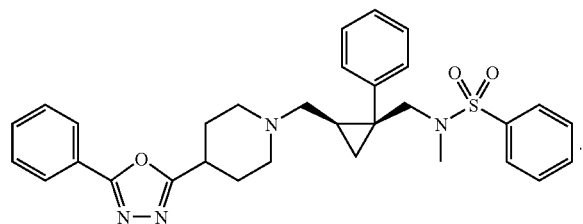
2. A pharmaceutical composition comprising a pharmaceutically effective amount of a compound according to claim 1 together with a pharmaceutically acceptable carrier.
3. The pharmaceutical composition according to claim 2 in the form of a tablet or capsule.
4. The pharmaceutical composition according to claim 2 in the form of a liquid.
* * * * *